US012680086B2

(12) United States Patent
Walter et al.

(10) Patent No.: US 12,680,086 B2
(45) Date of Patent: Jul. 14, 2026

(54) MODIFIED BETA-1,3-N-ACETYLGLUCOSAMINYLTRANSFERASE POLYPEPTIDES

(71) Applicant: Amyris, Inc., Emeryville, CA (US)

(72) Inventors: Jessica Walter, Emeryville, CA (US); Wenzong Li, Emeryville, CA (US); Christopher F. Mugler, Emeryville, CA (US); Victoria Hsiao, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 417 days.

(21) Appl. No.: 18/267,928

(22) PCT Filed: Dec. 16, 2021

(86) PCT No.: PCT/US2021/063818
§ 371 (c)(1),
(2) Date: Jun. 16, 2023

(87) PCT Pub. No.: WO2022/133093
PCT Pub. Date: Jun. 23, 2022

(65) Prior Publication Data
US 2024/0060056 A1 Feb. 22, 2024

Related U.S. Application Data

(60) Provisional application No. 63/127,059, filed on Dec. 17, 2020.

(51) Int. Cl.
| | |
|---|---|
| *C12N 9/10* | (2006.01) |
| *C12N 1/165* | (2026.01) |
| *C12P 19/18* | (2006.01) |
| *C12R 1/85* | (2006.01) |

(52) U.S. Cl.
CPC ........... *C12N 9/1051* (2013.01); *C12N 1/165* (2021.05); *C12P 19/18* (2013.01); *C12R 2001/85* (2021.05); *C12Y 204/01146* (2013.01)

(58) Field of Classification Search
CPC ...... C12N 9/1051; C12N 1/165; C12N 15/67; C12N 15/81; C12P 19/18; C12P 19/00; C12P 19/04; C12R 2001/85; C12Y 204/01146
See application file for complete search history.

(56) References Cited

U.S. PATENT DOCUMENTS

| | | | | |
|---|---|---|---|---|
| 5,705,367 | A * | 1/1998 | Gotschlich | .............. A61P 31/04 |
| | | | | 435/97 |
| 6,127,153 | A | 10/2000 | Johnson et al. | |
| 7,862,827 | B2 * | 1/2011 | Giuliani | ................. C07K 14/22 |
| | | | | 424/234.1 |
| 11,046,985 | B2 * | 6/2021 | Jennewein | ............. C12N 15/70 |
| 2012/0070457 | A1 | 3/2012 | Daugherty et al. | |
| 2018/0305724 | A1 | 10/2018 | Jennewein et al. | |
| 2024/0384315 | A1 * | 11/2024 | Pinel | ..................... C12N 9/1241 |
| 2025/0297294 | A1 * | 9/2025 | Pinel | ....................... C12P 19/12 |

FOREIGN PATENT DOCUMENTS

| | | |
|---|---|---|
| CN | 111548979 A | 8/2020 |
| WO | WO-2005/089775 A1 | 9/2005 |
| WO | WO-2020/058493 A1 | 3/2020 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
International Search Report and Written Opinion for PCT/US2021/063818, dated May 3, 2022 (12 pages).
Priem et al., "A new fermentation process allows large-scale production of human milk oligosaccharides by metabolically engineered bacteria," Glycobiology. 12(4):235-40 (Apr. 2002).

* cited by examiner

*Primary Examiner* — Ganapathirama Raghu
(74) *Attorney, Agent, or Firm* — Clark & Elbing LLP

(57) ABSTRACT

Provided herein are variant β-1,3-N-acetylglucosaminyl-transferase polypeptides capable of producing lacto-n-neotetraose, yeast cells capable of producing one or more human milk oligosaccharides, and methods of making such cells. Also, provided are fermentation compositions including the disclosed genetically modified yeast cells, and related methods of producing and recovering HMOs generated by the yeast cells.

20 Claims, 23 Drawing Sheets

Specification includes a Sequence Listing.

SEQ ID NO: 14    - LgtA(E170L,G179R)

SEQ ID NO: 5    *parent enzyme, LgtA(G179R)*

→ On-pathway product peak area increase (LNnT, LNTriose II)

--▶ Off-pathway product peak area reduction (LNnH, other unidentified analytes)

MODIFIED BETA-1,3-N-ACETYLGLUCOSAMINYLTRANSFERASE POLYPEPTIDES

SEQUENCE LISTING

The instant application contains a Sequence Listing which has been submitted electronically in ASCII format and is hereby incorporated by reference in its entirety. Said ASCII copy, created on Dec. 9, 2021, is named 51494_007WO2_Sequence_Listing_12_02_2021_ST25 and is 77,385 bytes in size.

BACKGROUND OF THE INVENTION

Human milk oligosaccharides (HMOs) are the third most abundant component of human milk, with only lactose and lipids present in higher concentrations. More than 200 different species of HMOs have been identified to date in human milk, including the naturally occurring tetra-saccharide lacto-n-neotetraose (LNnT) belonging to the group of non-fucosylated neutral HMOs. There is growing evidence attributing various health benefits to these milk compounds. Exemplary benefits include the promotion of the growth of protective intestinal microbes such as bifidobacteria, an increase in protection from gastrointestinal infections, a strengthening of the immune system, and an improvement in cognitive development. Because HMOs are not found in other milk sources, such as cow or goat, the only source of HMOs has traditionally been mother's milk. In efforts to improve the nutritional value of infant formula and expand the use of HMOs, for child and adult nutrition, there has been an increased interest in the synthetic production of these compounds.

The enzyme β-1,3-N-acetylglucosaminyltransferase (LgtA) carries out the transfer of N-acetylglucosamine (GlcNAc) onto lactose as an acceptor substrate as part of the biosynthetic pathway of a wide variety of HMOs. However, the enzyme LgtA may also be responsible for generating unwanted byproducts, including conversion of a desired HMO into longer-chain oligosaccharides, which both decreases product purity and reduces overall yield. Therefore, there remains a need for improved LgtA enzymes that result in enhanced HMO production and fewer unwanted byproducts.

BRIEF SUMMARY OF SOME ASPECTS OF THE INVENTION

The present disclosure provides variant β-1,3-N-acetylglucosaminyltransferase (LgtA) polypeptides, nucleic acids encoding the same, host cells expressing such polypeptides, and methods for producing a human milk oligosaccharide (HMO) in a host cell, such as a yeast cell. The variant LgtA polypeptides described herein exhibit a series of advantageous enzymatic properties, as these polypeptides contain modifications, such as amino acid substitutions and/or deletions relative to a wild-type LgtA polypeptide, that have presently been discovered to confer the enzyme with heightened specificity for binding to, and catalyzing the glycosidation of, its intended substrate relative to longer-chain oligosaccharides. This elevated substrate specificity provides a series of important methodological benefits for the production of HMOs. Particularly, it has been discovered that expression of a variant LgtA of the disclosure in a yeast cell genetically modified to biosynthesize one or more HMOs (e.g., a yeast strain expressing a β-1,4-galactosyltransferase (LgtB) and a lactose permease) not only augments the overall purity of the desired HMO, but may also improve the total yield of the HMO relative to a counterpart yeast strain modified to biosynthesize the HMO but that expresses the wild-type LgtA. The sections that follow describe, in further detail, the types of modifications that variant LgtA polypeptides of the disclosure exhibit and how these polypeptides can be used to produce a desired HMO.

In a first aspect, the disclosure provides a variant LgtA polypeptide including one or more (e.g., two, three, four, five, six, seven, eight, nine, ten, or more) amino acid substitutions or deletions relative to the amino acid sequence of SEQ ID NO: 1. In some embodiments, the one or more amino acid substitutions include an amino acid substitution at a residue selected from A27, P89, E170, G179, N180, I182, H183, N185, T186, M187, W206, A207, Q211, W213, V216, L229, V230, R233, H235, S240, K242, Y243, S244, Q247, I250, I254, Q255, A258, S265, S284, L288, K290, and E294 of SEQ ID NO: 1.

In some embodiments, the one or more amino acid substitutions include an amino acid substitution at residue G179 of SEQ ID NO: 1. In some embodiments, the amino acid substitution at residue G179 of SEQ ID NO: 1 substitutes G179 with an amino acid including a cationic side chain at physiological pH. In some embodiments, the amino acid substitution at residue G179 of SEQ ID NO: 1 is a G179R substitution.

In some embodiments, the one or more amino acid substitutions include an amino acid substitution at residue A27 of SEQ ID NO: 1. In some embodiments, the amino acid substitution at residue A27 of SEQ ID NO: 1 substitutes A27 with an amino acid including a hydrophobic, uncharged side chain at physiological pH. In some embodiments, the amino acid substitution at residue A27 of SEQ ID NO: 1 is an A27G substitution.

In some embodiments, the one or more amino acid substitutions include an amino acid substitution at residue P89 of SEQ ID NO: 1. In some embodiments, the amino acid substitution at residue P89 of SEQ ID NO: 1 substitutes P89 with an amino acid including a polar, uncharged chain at physiological pH. In some embodiments, the amino acid substitution at residue P89 of SEQ ID NO: 1 is a P89T substitution.

In some embodiments, the one or more amino acid substitutions include an amino acid substitution at residue E170 of SEQ ID NO: 1. In some embodiments, the amino acid substitution at residue E170 of SEQ ID NO: 1 substitutes E170 with an amino acid including a hydrophobic, uncharged side chain at physiological pH. In some embodiments, the amino acid substitution at residue E170 of SEQ ID NO: 1 is an E170L substitution.

In some embodiments, the one or more amino acid substitutions include an amino acid substitution at residue N180 of SEQ ID NO: 1. In some embodiments, the amino acid substitution at residue N180 of SEQ ID NO: 1 substitutes N180 with an amino acid including an anionic side chain at physiological pH. In some embodiments, the amino acid substitution at residue N180 of SEQ ID NO: 1 is an N180D substitution. In some embodiments, the amino acid substitution at residue N180 of SEQ ID NO: 1 substitutes N180 with an amino acid including a hydrophobic, uncharged side chain at physiological pH. In some embodiments, the amino acid substitution at residue N180 of SEQ ID NO: 1 is an N180A substitution.

In some embodiments, the one or more amino acid substitutions include an amino acid substitution at residue I182 of SEQ ID NO: 1. In some embodiments, the amino acid substitution at residue I182 of SEQ ID NO: 1 substitutes I182 with an amino acid including a hydrophobic, uncharged side chain at physiological pH. In some embodiments, the amino acid substitution at residue I182 of SEQ ID NO: 1 is an I182Y substitution. In some embodiments, the amino acid substitution at residue I182 of SEQ ID NO: 1 is an I182V substitution.

In some embodiments, the one or more amino acid substitutions include an amino acid substitution at residue H183 of SEQ ID NO: 1. In some embodiments, the amino acid substitution at residue H183 of SEQ ID NO: 1 is an H183P substitution. In some embodiments, the amino acid substitution at residue H183 of SEQ ID NO: 1 substitutes H183 with an amino acid including a polar, uncharged side chain at physiological pH. In some embodiments, the amino acid substitution at residue H183 of SEQ ID NO: 1 is an H183S substitution.

In some embodiments, the one or more amino acid substitutions include an amino acid substitution at residue N185 of SEQ ID NO: 1. In some embodiments, the amino acid substitution at residue N185 of SEQ ID NO: 1 is an N185G substitution.

In some embodiments, the one or more amino acid substitutions include an amino acid substitution at residue T186 of SEQ ID NO: 1. In some embodiments, the amino acid substitution at residue T186 of SEQ ID NO: 1 substitutes T186 with an amino acid including an anionic side chain at physiological pH. In some embodiments, the amino acid substitution at residue T186 of SEQ ID NO: 1 is a T186D substitution. In some embodiments, the amino acid substitution at residue T186 of SEQ ID NO: 1 is a T186G substitution.

In some embodiments, the one or more amino acid substitutions include an amino acid substitution at residue M187 of SEQ ID NO: 1. In some embodiments, the amino acid substitution at residue M187 of SEQ ID NO: 1 is an M187P substitution.

In some embodiments, the one or more amino acid substitutions include an amino acid substitution at residue W206 of SEQ ID NO: 1. In some embodiments, the amino acid substitution at residue W206 of SEQ ID NO: 1 substitutes W206 with an amino acid including a polar, uncharged side chain at physiological pH. In some embodiments, the amino acid substitution at residue W206 of SEQ ID NO: 1 is a W206N substitution.

In some embodiments, the one or more amino acid substitutions include an amino acid substitution at residue A207 of SEQ ID NO: 1. In some embodiments, the amino acid substitution at residue A207 of SEQ ID NO: 1 substitutes A207 with an amino acid including a hydrophobic, uncharged side chain at physiological pH. In some embodiments, the amino acid substitution at residue A207 of SEQ ID NO: 1 is an A207V substitution.

In some embodiments, the one or more amino acid substitutions include an amino acid substitution at residue Q211 of SEQ ID NO: 1. In some embodiments, the amino acid substitution at residue Q211 of SEQ ID NO: 1 substitutes Q211 with an amino acid including a hydrophobic, uncharged side chain at physiological pH. In some embodiments, the amino acid substitution at residue Q211 of SEQ ID NO: 1 is a Q211V substitution, a Q211I substitution, or a Q211L substitution. In some embodiments, the amino acid substitution at residue Q211 of SEQ ID NO: 1 is a Q211C substitution.

In some embodiments, the one or more amino acid substitutions include an amino acid substitution at residue W213 of SEQ ID NO: 1. In some embodiments, the amino acid substitution at residue W213 of SEQ ID NO: 1 substitutes W213 with an amino acid including a polar, uncharged side chain at physiological pH. In some embodiments, the amino acid substitution at residue W213 of SEQ ID NO: 1 is a W213S substitution or a W213N substitution.

In some embodiments, the one or more amino acid substitutions include an amino acid substitution at residue V216 of SEQ ID NO: 1. In some embodiments, the amino acid substitution at residue V216 of SEQ ID NO: 1 substitutes V216 with an amino acid including a hydrophobic, uncharged side chain at physiological pH. In some embodiments, the amino acid substitution at residue V216 of SEQ ID NO: 1 is a V216L substitution.

In some embodiments, the one or more amino acid substitutions include an amino acid substitution at residue L229 of SEQ ID NO: 1. In some embodiments, the amino acid substitution at residue L229 of SEQ ID NO: 1 substitutes L229 with an amino acid including a hydrophobic, uncharged side chain at physiological pH. In some embodiments, the amino acid substitution at residue L229 of SEQ ID NO: 1 is an L229A substitution. In some embodiments, the amino acid substitution at residue L229 of SEQ ID NO: 1 is an L229P substitution.

In some embodiments, the one or more amino acid substitutions include an amino acid substitution at residue V230 of SEQ ID NO: 1. In some embodiments, the amino acid substitution at residue V230 of SEQ ID NO: 1 substitutes V230 with an amino acid including an anionic side chain at physiological pH. In some embodiments, the amino acid substitution at residue V230 of SEQ ID NO: 1 is a V230D substitution. In some embodiments, the amino acid substitution at residue V230 of SEQ ID NO: 1 substitutes V230 with an amino acid including a hydrophobic, uncharged side chain at physiological pH. In some embodiments, the amino acid substitution at residue V230 of SEQ ID NO: 1 is a V230A substitution.

In some embodiments, the one or more amino acid substitutions include an amino acid substitution at residue R233 of SEQ ID NO: 1. In some embodiments, the amino acid substitution at residue R233 of SEQ ID NO: 1 substitutes R233 with an amino acid including a hydrophobic, uncharged side chain at physiological pH. In some embodiments, the amino acid substitution at residue R233 of SEQ ID NO: 1 is an R233I substitution.

In some embodiments, the one or more amino acid substitutions include an amino acid substitution at residue H235 of SEQ ID NO: 1. In some embodiments, the amino acid substitution at residue H235 of SEQ ID NO: 1 substitutes H235 with an amino acid including a cationic side chain at physiological pH. In some embodiments, the amino acid substitution at residue H235 of SEQ ID NO: 1 is an H235R substitution.

In some embodiments, the one or more amino acid substitutions include an amino acid substitution at residue S240 of SEQ ID NO: 1. In some embodiments, the amino acid substitution at residue S240 of SEQ ID NO: 1 substitutes S240 with an amino acid including a polar, uncharged side chain at physiological pH. In some embodiments, the amino acid substitution at residue S240 of SEQ ID NO: 1 is an S240N substitution. In some embodiments, the amino acid substitution at residue S240 of SEQ ID NO: 1 substitutes S240 with an amino acid including a hydrophobic, uncharged side chain at physiological pH. In some embodiments, the amino acid substitution at residue S240 of SEQ ID NO: 1 is an S240Y substitution.

In some embodiments, the one or more amino acid substitutions include an amino acid substitution at residue K242 of SEQ ID NO: 1. In some embodiments, the amino acid substitution at residue K242 of SEQ ID NO: 1 substitutes K242 with an amino acid including an anionic side chain at physiological pH. In some embodiments, the amino acid substitution at residue K242 of SEQ ID NO: 1 is a K242D substitution.

In some embodiments, the one or more amino acid substitutions include an amino acid substitution at residue Y243 of SEQ ID NO: 1. In some embodiments, the amino acid substitution at residue Y243 of SEQ ID NO: 1 substitutes Y243 with an amino acid including a polar, uncharged side chain at physiological pH. In some embodiments, the amino acid substitution at residue Y243 of SEQ ID NO: 1 is a Y243S substitution. In some embodiments, the amino acid substitution at residue Y243 of SEQ ID NO: 1 substitutes Y243 with an amino acid including a hydrophobic, uncharged side chain at physiological pH. In some embodiments, the amino acid substitution at residue Y243 of SEQ ID NO: 1 is a Y243A substitution or a Y243L substitution. In some embodiments, the amino acid substitution at residue Y243 of SEQ ID NO: 1 substitutes Y243 with an amino acid including a cationic side chain at physiological pH. In some embodiments, the amino acid substitution at residue Y243 of SEQ ID NO: 1 is a Y243R substitution.

In some embodiments, the one or more amino acid substitutions include an amino acid substitution at residue S244 of SEQ ID NO: 1. In some embodiments, the amino acid substitution at residue S244 of SEQ ID NO: 1 substitutes S244 with an amino acid including a polar, uncharged side chain at physiological pH. In some embodiments, the amino acid substitution at residue S244 of SEQ ID NO: 1 is an S244T substitution.

In some embodiments, the one or more amino acid substitutions include an amino acid substitution at residue Q247 of SEQ ID NO: 1. In some embodiments, the amino acid substitution at residue Q247 of SEQ ID NO: 1 is a Q247C substitution.

In some embodiments, the one or more amino acid substitutions include an amino acid substitution at residue L288 of SEQ ID NO: 1. In some embodiments, the amino acid substitution at residue L288 of SEQ ID NO: 1 substitutes L288 with an amino acid including a polar, uncharged side chain at physiological pH. In some embodiments, the amino acid substitution at residue L288 of SEQ ID NO: 1 is an L288S substitution.

In some embodiments, the one or more amino acid substitutions include an amino acid substitution at residue I250 of SEQ ID NO: 1. In some embodiments, the amino acid substitution at residue I250 of SEQ ID NO: 1 substitutes I250 with an amino acid including a hydrophobic, uncharged side chain at physiological pH. In some embodiments, the amino acid substitution at residue I250 of SEQ ID NO: 1 is an I250F substitution.

In some embodiments, the one or more amino acid substitutions include an amino acid substitution at residue I254 of SEQ ID NO: 1. In some embodiments, the amino acid substitution at residue I254 of SEQ ID NO: 1 substitutes I254 with an amino acid including a hydrophobic, uncharged side chain at physiological pH. In some embodiments, wherein the amino acid substitution at residue I254 of SEQ ID NO: 1 is an I254A substitution.

In some embodiments, the one or more amino acid substitutions include an amino acid substitution at residue Q255 of SEQ ID NO: 1. In some embodiments, the amino acid substitution at residue Q255 of SEQ ID NO: 1 substitutes Q255 with an amino acid including an anionic side chain at physiological pH. In some embodiments, the amino acid substitution at residue Q255 of SEQ ID NO: 1 is a Q255D substitution.

In some embodiments, the one or more amino acid substitutions include an amino acid substitution at residue A258 of SEQ ID NO: 1. In some embodiments, the amino acid substitution at residue A258 of SEQ ID NO: 1 substitutes A258 with an amino acid including an anionic side chain at physiological pH. In some embodiments, the amino acid substitution at residue A258 of SEQ ID NO: 1 is an A258D substitution. In some embodiments, the amino acid substitution at residue A258 of SEQ ID NO: 1 substitutes A258 with an amino acid including a cationic side chain at physiological pH. In some embodiments, the amino acid substitution at residue A258 of SEQ ID NO: 1 is an A258R substitution.

In some embodiments, the one or more amino acid substitutions include an amino acid substitution at residue S265 of SEQ ID NO: 1. In some embodiments, the amino acid substitution at residue S265 of SEQ ID NO: 1 substitutes S265 with an amino acid including a cationic side chain at physiological pH. In some embodiments, the amino acid substitution at residue S265 of SEQ ID NO: 1 is an S265H substitution.

In some embodiments, the one or more amino acid substitutions include an amino acid substitution at residue S284 of SEQ ID NO: 1. In some embodiments, the amino acid substitution at residue S284 of SEQ ID NO: 1 substitutes S284 with an amino acid including a polar, uncharged side chain at physiological pH. In some embodiments, the amino acid substitution at residue S284 of SEQ ID NO: 1 is an S284Y substitution.

In some embodiments, the one or more amino acid substitutions include an amino acid substitution at residue K290 of SEQ ID NO: 1. In some embodiments, the amino acid substitution at residue K290 of SEQ ID NO: 1 substitutes K290 with an amino acid including a polar, uncharged side chain at physiological pH. In some embodiments, the amino acid substitution at residue K290 of SEQ ID NO: 1 is an K290Q substitution.

In some embodiments, the one or more amino acid substitutions include an amino acid substitution at residue E294 of SEQ ID NO: 1. In some embodiments, the amino acid substitution at residue E294 of SEQ ID NO: 1 substitutes E294 with an amino acid including a polar, uncharged side chain at physiological pH. In some embodiments, the amino acid substitution at residue E294 of SEQ ID NO: 1 is an E294N substitution.

In some embodiments, the amino acid substitutions include G179R and E170L relative to SEQ ID NO: 1. In some embodiments, the amino acid substitutions include G179R and I182V relative to SEQ ID NO: 1. In some embodiments, the amino acid substitutions include G179R and V216L relative to SEQ ID NO: 1. In some embodiments, the amino acid substitutions include G179R and K290Q relative to SEQ ID NO: 1. In some embodiments, the amino acid substitutions include G179R and V230A relative to SEQ ID NO: 1. In some embodiments, the amino acid substitutions include G179R and S244T relative to SEQ ID NO: 1. In some embodiments, the amino acid substitutions include G179R and S265H relative to SEQ ID NO: 1. In some embodiments, the amino acid substitutions include G179R and S284Y relative to SEQ ID NO: 1. In some embodiments, the amino acid substitutions include G179R and A27G relative to SEQ ID NO: 1.

In some embodiments, wherein the one or more amino acid substitutions include a deletion of residues 301-348 of SEQ ID NO: 1.

In some embodiments, the polypeptide has an amino acid sequence that is from about 85% to about 99.7% (e.g., 85.5%, 86%, 86.5%, 87%, 87.5%, 88%, 88.5%, 89%, 89.5%, 90%, 90.5%, 91%, 91.2%, 92%, 92.5%, 93%, 93.5%, 94%, 94.5%, 95%, 95.5%, 96%, 96.5%, 97%, 97.5%, 98%, 98.5%, 99%, and 99.5%) identical to the amino acid sequence of SEQ ID NO: 1. In some embodiments, the polypeptide has an amino acid sequence that is from about 90% to about 99.7% (e.g., 90.5%, 91%, 91.2%, 92%, 92.5%, 93%, 93.5%, 94%, 94.5%, 95%, 95.5%, 96%, 96.5%, 97%, 97.5%, 98%, 98.5%, 99%, and 99.5%) identical to the amino acid sequence of SEQ ID NO: 1. In some embodiments, the polypeptide has an amino acid sequence that is from about 95% to about 99.7% (e.g., 95.5%, 96%, 96.5%, 97%, 97.5%, 98%, 98.5%, 99%, and 99.5%) identical to the amino acid sequence of SEQ ID NO: 1.

In some embodiments, the polypeptide has an amino acid sequence that differs from the amino acid sequence of SEQ ID NO: 1 only by way of (i) the one or more amino acid substitutions or deletions and, optionally, (ii) one or more (e.g., two, three, four, five, six, seven, eight, nine, ten, or more) additional, conservative amino acid substitutions. In some embodiments, the polypeptide has an amino acid sequence that differs from the amino acid sequence of SEQ ID NO: 1 only by way of the one or more amino acid substitutions or deletions.

In some embodiments, the polypeptide has an amino acid sequence that is at least 85% (e.g., at least 86%, 87%, 88%, 89%, 90%, 91%, 92%, 93%, 94%, 95%, 96%, 97%, 98%, and 99%) identical to the amino acid sequence of any one of SEQ ID NO: 2-22. In some embodiments, the polypeptide has an amino acid sequence that is at least 85% (e.g., at least 86%, 87%, 88%, 89%, 90%, 91%, 92%, 93%, 94%, 95%, 96%, 97%, 98%, and 99%) identical to the amino acid sequence of any one of SEQ ID NO: 14-17. In some embodiments, the polypeptide has an amino acid sequence that is at least 90% (e.g., at least 91%, 92%, 93%, 94%, 95%, 96%, 97%, 98%, and 99%) identical to the amino acid sequence of any one of SEQ ID NO: 2-22. In some embodiments, the polypeptide has an amino acid sequence that is at least 90% (e.g., at least 91%, 92%, 93%, 94%, 95%, 96%, 97%, 98%, and 99%) identical to the amino acid sequence of any one of SEQ ID NO: 14-17. In some embodiments, the polypeptide has an amino acid sequence that is at least 95% (e.g., at least 96%, 97%, 98%, and 99%) identical to the amino acid sequence of any one of SEQ ID NO: 2-22. In some embodiments, the polypeptide has an amino acid sequence that is at least 95% (e.g., at least 96%, 97%, 98%, and 99%) identical to the amino acid sequence of any one of SEQ ID NO: 14-17. In some embodiments, the polypeptide has the amino acid sequence of any one of SEQ ID NO: 2-22. In some embodiments, the polypeptide has the amino acid sequence of any one of SEQ ID NO: 14-17. In some embodiments, the polypeptide exhibits increased substrate specificity for lactose over a longer chain oligosaccharide as compared to a polypeptide having the amino acid sequence of SEQ ID NO: 1.

In some embodiments, the longer chain oligosaccharide is para-lacto-N-neohexaose (p-LNnH), lacto-N-neotetraose (LNnT), lacto-N-tetraose (LNT), lacto-N-fucopentaose (LNFP) I, LNFP II, LNFP III, LNFP V, LNFP VI, lacto-N-difucohexaose (LNDFH) I, LNDFH II, lacto-N-hexaose (LNH), lacto-N-neohexaose (LNnH), fucosyllacto-N-hexaose (F-LNH) I, F-LNH II, difucosyllacto-N-hexaose (DF-LNH) I, DF-LNH II, difucosyllacto-N-neohexaose (DF-LNnH), difucosyl-para-lacto-N-hexaose (DF-para-LNH), difucosyl-para-lacto-N-neohexaose (DF-para-LNnH), trifucosyllacto-N-hexaose (TF-LNH), sialyllacto-N-tetraose (LST) a, LST b, LST c, disialyllacto-N-tetraose (DS-LNT), fucosyl-sialyllacto-N-tetraose (F-LST) a, F-LST b, fucosyl-sialyllacto-N-hexaose (FS-LNH), fucosyl-sialyl-lacto-N-neohexaose (FS-LNnH) I, or fucosyl-disialyllacto-N-hexaose (FDS-LNH) II. In some embodiments, the longer chain oligosaccharide is LNnT.

In another aspect, the disclosure provides a nucleic acid encoding any one of the variant polypeptides described herein. In another aspect, the disclosure provides any one of the variant polypeptides described herein or any one of the nucleic acids described herein. In some embodiments, the nucleic acid encoding the variant polypeptide is integrated into the genome of the cell. In some embodiments, the nucleic acid encoding the variant polypeptide is present within a plasmid. In some embodiments, the cell is capable of producing a human milk oligosaccharide. In some embodiments, the cell includes one or more heterologous nucleic acids that each, independently, encode one or more additional enzymes of the biosynthetic pathway of the human milk oligosaccharide. In some embodiments, the one or more heterologous nucleic acids encoding one or more additional enzymes of the biosynthetic pathway of the human milk oligosaccharide are integrated into the genome of the cell. In some embodiments, the one or more heterologous nucleic acids encoding one or more additional enzymes of the biosynthetic pathway of the human milk oligosaccharide are present within one or more plasmids. In some embodiments, the human milk oligosaccharide is LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II. In some embodiments, the human milk oligosaccharide is LNnT.

In some embodiments, the one or more additional enzymes include one or both of a LgtB and a UDP-N-acetylglucosamine diphosphorylase. In some embodiments, the one or more additional enzymes include an LgtB. In some embodiments, the LgtB has an amino acid sequence that is at least 85% (e.g., at least 86%, 87%, 88%, 89%, 90%, 91%, 92%, 93%, 94%, 95%, 96%, 97%, 98%, and 99%) identical to the amino acid sequence of SEQ ID NO: 24. In some embodiments, the LgtB has an amino acid sequence that is at least 90% (e.g., at least 91%, 92%, 93%, 94%, 95%, 96%, 97%, 98%, and 99%) identical to the amino acid sequence of SEQ ID NO: 24. In some embodiments, the LgtB has an amino acid sequence that is at least 95% (e.g., at least 96%, 97%, 98%, and 99%) identical to the amino acid sequence of SEQ ID NO: 24. In some embodiments, the LgtB has the amino acid sequence SEQ ID NO: 24. In some embodiments, the LgtB has an amino acid sequence that is at least 85% (e.g., at least 86%, 87%, 88%, 89%, 90%, 91%, 92%, 93%, 94%, 95%, 96%, 97%, 98%, and 99%) identical to the amino acid sequence of SEQ ID NO: 25. In some embodiments, the LgtB has an amino acid sequence that is at least 90% (e.g., at least 91%, 92%, 93%, 94%, 95%, 96%, 97%, 98%, and 99%) identical to the amino acid sequence of SEQ ID NO: 25. In some embodiments, the LgtB has an amino acid sequence that is at least 95% (e.g., at least 96%, 97%, 98%, and 99%) identical to the amino acid sequence of SEQ ID NO: 25. In some embodiments, the LgtB has the amino acid sequence SEQ ID NO: 25.

In some embodiments, wherein the one or more heterologous nucleic acids encode a protein that transports lactose into the cell. In some embodiments, the protein that transports lactose into the cell is a lactose permease. In some embodiments, the lactose permease has an amino acid sequence that is at least 85% (e.g., at least 86%, 87%, 88%, 89%, 90%, 91%, 92%, 93%, 94%, 95%, 96%, 97%, 98%, and 99%) identical to the amino acid sequence of SEQ ID NO: 23. In some embodiments, the lactose permease has an amino acid sequence that is at least 90% (e.g., at least 91%, 92%, 93%, 94%, 95%, 96%, 97%, 98%, and 99%) identical to the amino acid sequence of SEQ ID NO: 23. In some embodiments, the lactose permease has an amino acid sequence that is at least 95% (e.g., 96%, 97%, 98%, and 99%) identical to the amino acid sequence of SEQ ID NO: 23. In some embodiments, the lactose permease has the amino acid sequence SEQ ID NO: 23.

In some embodiments, the protein that transports lactose into the cell is a lactose transporter. In some embodiments, expression of the nucleic acid encoding the variant polypeptide and/or the one or more heterologous nucleic acids is driven by an inducible promoter or is negatively regulated by the activity of a promoter that is responsive to a small molecule.

In some embodiments, the host cell is a yeast cell. In some embodiments, the yeast cell is a *Saccharomyces* sp. cell or a *Kluveromyces* sp. cell. In some embodiments, the yeast cell is a *Saccharomyces cerevisiae* cell. In some embodiments, the yeast cell is a *Kluveromyces marxianus* cell.

In another aspect, the disclosure provides a method of producing a human milk oligosaccharide including culturing a population of any one of the host cells described herein in a culture medium under conditions suitable for the host cells to produce the human milk oligosaccharide. In some embodiments, the human milk oligosaccharide is LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II. In some embodiments, the human milk oligosaccharide is LNnT.

In some embodiments, the culture medium includes sucrose and lactose, optionally wherein the mass ratio of the sucrose to the lactose is less than 40. In some embodiments, prior to the culturing, the method includes growing the population of host cells in a growth medium including a small molecule, wherein expression of the nucleic acid encoding the variant polypeptide and/or the one or more heterologous nucleic acids is negatively regulated by the activity of a promoter responsive to the small molecule, and wherein the concentration of the small molecule in the culture medium during the culturing is sufficiently low that the promoter is no longer active.

In another aspect, the disclosure provides a fermentation composition including a population of host cells including any one of the host cells described herein and (ii) a culture medium including a human milk oligosaccharide produced from the host cells. In some embodiments, the human milk oligosaccharide is LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II. In some embodiments, the human milk oligosaccharide is LNnT.

In another aspect, the disclosure provides a method of recovering a human milk oligosaccharide from any one of the fermentation compositions described herein including separating at least a portion of the population of host cells from the culture medium; contacting the separated host cells with a heated aqueous wash liquid; and removing the wash liquid from the separated host cells. In some embodiments, one or both of the separating and removing includes centrifugation.

In another aspect, the disclosure provides a method of genetically modifying a yeast cell to produce a human milk oligosaccharide including introducing a heterologous nucleic acid encoding any one of the variant polypeptides described herein into the yeast cell and introducing one or more heterologous nucleic acids that each, independently, encode one or more additional enzymes of the biosynthetic pathway of the human milk oligosaccharide into the yeast cell; or introducing a heterologous nucleic acid encoding any one of the variant polypeptides described herein into the yeast cell, wherein the yeast cell includes one or more heterologous nucleic acids that each, independently, encode one or more additional enzymes of the biosynthetic pathway of the human milk oligosaccharide. In some embodiments, the nucleic acid encoding the variant polypeptide is integrated into the genome of the cell. In some embodiments, the nucleic acid encoding the variant polypeptide is present within a plasmid. In some embodiments, the one or more heterologous nucleic acids encoding one or more additional enzymes of the biosynthetic pathway of the human milk oligosaccharide are integrated into the genome of the cell. In some embodiments, the one or more heterologous nucleic acids encoding one or more additional enzymes of the biosynthetic pathway of the human milk oligosaccharide are present within one or more plasmids. In some embodiments, the human milk oligosaccharide is LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II. In some embodiments, the human milk oligosaccharide is LNnT.

In some embodiments, the one or more additional enzymes include one or both of an LgtB and a UDP-N-acetylglucosamine diphosphorylase. In some embodiments, the one or more additional enzymes include an LgtB. In some embodiments, the LgtB has an amino acid sequence that is at least 85% (e.g., at least 86%, 87%, 88%, 89%, 90%, 91%, 92%, 93%, 94%, 95, 96%, 97%, 98%, and 99%) identical to the amino acid sequence of SEQ ID NO: 24. In some embodiments, the LgtB has an amino acid sequence that is at least 90% (e.g., 91%, 92%, 93%, 94%, 95, 96%, 97%, 98%, and 99%) at least identical to the amino acid sequence of SEQ ID NO: 24. In some embodiments, the LgtB has an amino acid sequence that is at least 95% (e.g., at least 96%, 97%, 98%, and 99%) identical to the amino acid sequence of SEQ ID NO: 24. In some embodiments, the LgtB has the amino acid sequence SEQ ID NO: 24. In some embodiments, the LgtB has an amino acid sequence that is at least 85% (e.g., at least 86%, 87%, 88%, 89%, 90%, 91%, 92%, 93%, 94%, 95, 96%, 97%, 98%, and 99%) identical to the amino acid sequence of SEQ ID NO: 25. In some embodiments, the LgtB has an amino acid sequence that is at least 90% (e.g., 91%, 92%, 93%, 94%, 95, 96%, 97%, 98%, and 99%) at least identical to the amino acid sequence of SEQ ID NO: 25. In some embodiments, the LgtB has an amino acid sequence that is at least 95% (e.g., at least 96%, 97%, 98%, and 99%) identical to the amino acid sequence of SEQ ID NO: 25. In some embodiments, the LgtB has the amino acid sequence SEQ ID NO: 25.

In some embodiments, the one or more heterologous nucleic acids encode a protein that transports lactose into the cell. In some embodiments, the protein that transports lactose into the cell is a lactose permease. In some embodiments, the lactose permease has an amino acid sequence that is at least 85% (e.g., 86%, 87%, 88%, 89%, 90%, 91%, 92%, 93%, 94%, 95, 96%, 97%, 98%, and 99%) identical to the amino acid sequence of SEQ ID NO: 23. In some embodiments, the lactose permease has an amino acid sequence that is at least 90% (e.g., 91%, 92%, 93%, 94%, 95, 96%, 97%, 98%, and 99%) identical to the amino acid sequence of SEQ ID NO: 23. In some embodiments, the lactose permease has an amino acid sequence that is at least 95% (e.g., at least 96%, 97%, 98%, and 99%) identical to the amino acid sequence of SEQ ID NO: 23. In some embodiments, the lactose permease has the amino acid sequence of SEQ ID NO: 23.

In some embodiments, expression of the nucleic acid encoding the variant polypeptide and/or the one or more heterologous nucleic acids is driven by an inducible promoter or is negatively regulated by the activity of a promoter that is responsive to a small molecule. In some embodiments, the yeast cell is a *Saccharomyces* sp. cell or a *Kluveromyces* sp. cell. In some embodiments, the yeast cell is a *Saccharomyces cerevisiae* cell. In some embodiments, the yeast cell is a *Kluveromyces marxianus* cell.

In some embodiments, the method results in increased titer of the human milk oligosaccharide relative to a corresponding method in which a polypeptide having the amino acid sequence of SEQ ID NO: 1 is used in place of the variant polypeptide. In some embodiments, the human milk oligosaccharide is LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II. In some embodiments, the human milk oligosaccharide is LNnT.

In some embodiments, the method results in from about a 2-fold increase to about a 6-fold increase in LNnT titer relative to a corresponding method in which a polypeptide having the amino acid sequence of SEQ ID NO: 1 is used in place of the variant polypeptide. In some embodiments, the method results in increased production of LNnT relative to para-lacto-N-neopentaose (p-LNnP) or p-LNnH. In some embodiments, the method results in from about a 4-fold increase to about a 20-fold increase, by mass, in production of LNnT relative to p-LNnH.

In some embodiments, the method results in an increase in the ratio of LNnT produced to p-LNnH produced, by mass, relative to a corresponding method in which a polypeptide having the amino acid sequence of SEQ ID NO: 1 is used in place of the variant polypeptide. In some embodiments, the method results in from about a 2-fold increase to about a 20-fold increase in the ratio of LNnT produced to p-LNnH produced, by mass, relative to a corresponding method in which a polypeptide having the amino acid sequence of SEQ ID NO: 1 is used in place of the variant polypeptide. In some embodiments, the method results in at least a 5-fold increase in the ratio of LNnT produced to p-LNnH produced, by mass, relative to a corresponding method in which a polypeptide having the amino acid sequence of SEQ ID NO: 1 is used in place of the variant polypeptide. In some embodiments, in at least a 6-fold increase in the ratio of LNnT produced to p-LNnH produced, by mass, relative to a corresponding method in which a polypeptide having the amino acid sequence of SEQ ID NO: 1 is used in place of the variant polypeptide. In some embodiments, the method results in at least a 7-fold increase in the ratio of LNnT produced to p-LNnH produced, by mass, relative to a corresponding method in which a polypeptide having the amino acid sequence of SEQ ID NO: 1 is used in place of the variant polypeptide. In some embodiments, the method results in at least an 8-fold increase in the ratio of LNnT produced to p-LNnH produced, by mass, relative to a corresponding method in which a polypeptide having the amino acid sequence of SEQ ID NO: 1 is used in place of the variant polypeptide.

Definitions

The terms "human milk oligosaccharide" and "HMO" are used interchangeably herein to refer to a group of nearly 200 identified sugar molecules that are found as the third most abundant component in human breast milk. HMOs in human breast milk are a complex mixture of free, indigestible carbohydrates with many different biological roles, including promoting the development of a functional infant immune system. HMOs include, without limitation, lacto-N-neotetraose (LNnT), 2'-fucosyllactose (2'-FL), 3-fucosyllactose (3-FL), difucosyllactose (DFL), lacto-N-tetraose (LNT), lacto-N-fucopentaose (LNFP) I, LNFP II, LNFP III, LNFP V, LNFP VI, lacto-N-difucohexaose (LNDFH) I, LNDFH II, lacto-N-hexaose (LNH), lacto-N-neohexaose (LNnH), fucosyllacto-N-hexaose (F-LNH) I, F-LNH II, difucosyllacto-N-hexaose (DFLNH) I, DFLNH II, difucosyllacto-N-neohexaose (DFLNnH), difucosyl-para-lacto-N-hexaose (DF-para-LNH), difucosyl-para-lacto-N-neohexaose (DF-para-LNnH), trifucosyllacto-N-hexaose (TF-LNH), 3'-siallylactose (3'-SL), 6'-siallylactose (6'-SL), sialyllacto-N-tetraose (LST) a, LST b, LST c, disialyllacto-N-tetraose (DS-LNT), fucosyl-sialyllacto-N-tetraose (F-LST) a, F-LST b, fucosyl-sialyllacto-N-hexaose (FS-LNH), fucosyl-sialyllacto-N-neohexaose (FS-LNnH) I, and fucosyl-disialyllacto-N-hexaose (FDS-LNH II), among others.

The terms "variant LgtA" and "variant β-1,3-N-acetyl-glucosaminyltransferase" refer to a polypeptide having at least one (e.g., two, three, four, five, six, seven, eight, nine, ten, or more) amino acids substitutions or deletions relative to a wild-type LgtA polypeptide (e.g., a wild-type LgtA polypeptide from *N. meningitidis*, the amino acid sequence of which is set forth in SEQ ID NO: 1. The LgtA polypeptide may be modified (e.g., by way of one or more of the amino acid substitutions or deletions described herein) to enhance its specificity for binding to, and catalyzing the glycosidation of, the enzyme's intended substrate in the biosynthetic pathway of an HMO relative to a longer-chain oligosaccharide.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus, the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA, or a hybrid, in which the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. Nucleic acid sequences are presented in the 5' to 3' direction unless otherwise specified.

As used herein, the terms "polypeptide," "peptide," and "protein" are used interchangeably to refer to a polymer of amino acid residues. The terms encompass amino acid chains of any length, including full-length proteins, wherein the amino acid residues are linked by covalent peptide bonds.

"Percent (%) sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An exemplary algorithm that may be used to determine whether a polypeptide has sequence identity to a polypeptide disclosed herein is the BLAST algorithm, which is described in Altschul et al., 1990, J. Mol. Biol. 215:403-410, which is incorporated herein by reference. Software for performing BLAST analyses is publicly available through the National Center for Biotechnology Information (on the worldwide web at ncbi.nlm.nih.gov/). For amino acid sequences, the BLASTP program uses as defaults a word size (W) of 3, an expectation (E) of 10, and the BLOSUM62 scoring matrix (see Henikoff & Henikoff, 1989, Proc. Natl. Acad. Sci. USA 89:10915). Other programs that may be used include the Needleman-Wunsch procedure, J. Mol. Biol. 48:443-453 (1970), using BLOSUM62, a Gap start penalty of 7 and gap extend penalty of 1; and gapped BLAST 2.0 (see Altschul, et al. 1997, Nucleic Acids Res. 25:3389-3402). Although various algorithms can be employed to determine percent identity, for purposes herein, % amino acid sequence identity values are generated using the sequence comparison computer program BLASTP (protein-protein BLAST algorithm) using default parameters.

Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following a sequence comparison algorithm or by manual alignment and visual inspection as described above. Optionally, the identity exists over a region that is at least about 50 nucleotides (or 20 amino acids) in length, or more preferably over a region that is 100 to 500 or 1000 or more nucleotides (or 50, 100, or 200 or more amino acids) in length.

Nucleic acid or protein sequences that are substantially identical to a reference sequence include "conservatively modified variants." With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, at pH 7, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, Proteins: Structures and Molecular Principles. 1984, New York: W. H. Freeman).

Accordingly, the terms "conservative mutation," "conservative substitution," or "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume† |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Glr | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in $A^3$: 50-100 is small, 100-150 is intermediate, 150-200 is large, and >200 is bulky A "genetic pathway" or "biosynthetic pathway" as used herein refers to a set of at least two different coding sequences, where the coding sequences encode enzymes that catalyze different parts of a synthetic pathway to form a desired product (e.g., a HMO). In a genetic pathway, a first encoded enzyme uses a substrate to make a first product which in turn is used as a substrate for a second encoded enzyme to make a second product. In some embodiments, the genetic pathway includes 3 or more members (e.g., 3, 4, 5, 6, 7, 8, 9, etc.), wherein the product of one encoded enzyme is the substrate for the next enzyme in the synthetic pathway.

As used herein, the term "hydrophobic side-chain" refers to an amino acid side-chain that exhibits low solubility in water relative due to, e.g., the steric or electronic properties of the chemical moieties present within the side-chain. Examples of amino acids containing hydrophobic side-chains include those containing unsaturated aliphatic hydrocarbons, such as alanine, valine, leucine, isoleucine, proline, and methionine, as well as amino acids containing aromatic ring systems that are electrostatically neutral at physiological pH, such as tryptophan, phenylalanine, and tyrosine.

As used herein, the term "heterologous" refers to what is not normally found in nature. The term "heterologous nucleic acid" refers to a nucleic acid not normally found in a given cell in nature. A heterologous nucleic acid can be: (a) foreign to its host cell, i.e., exogenous to the host cell such that a host cell does not naturally contain the nucleic acid; (b) naturally found in the host cell, i.e., endogenous or native to the host cell, but present at an unnatural quantity in the cell (i.e., greater or lesser quantity than naturally found in the host cell); (c) be naturally found in the host cell but positioned outside of its natural locus. A "heterologous" polypeptide refers to a polypeptide that is encoded by a "heterologous nucleic acid". Thus, for example, a "heterologous" polypeptide may be naturally produced by a host cell but is encoded by a heterologous nucleic acid that has been introduced into the host cell by genetic engineering. For example, a "heterologous" polypeptide can include embodiments in which an endogenous polypeptide is produced by an expression construct and is overexpressed in the host cell compared to native levels of the polypeptide produced by the host cell.

As used herein, the term "introducing" in the context of introducing a nucleic acid or protein into a host cell refers to any process that results in the presence of a heterologous nucleic acid or polypeptide inside the host cell. For example, the term encompasses introducing a nucleic acid molecule (e.g., a plasmid or a linear nucleic acid) that encodes the nucleic acid of interest (e.g., an RNA molecule) or polypeptide of interest and results in the transcription of the RNA molecules and translation of the polypeptides. The term also encompasses integrating the nucleic acid encoding the RNA molecules or polypeptides into the genome of a progenitor cell. The nucleic acid is then passed through subsequent generations to the host cell, so that, for example, a nucleic acid encoding an RNA-guided endonuclease is "pre-integrated" into the host cell genome. In some cases, introducing refers to translocation of a nucleic acid or polypeptide from outside the host cell to inside the host cell. Various methods of introducing nucleic acids, polypeptides and other biomolecules into host cells are contemplated, including but not limited to, electroporation, contact with nanowires or nanotubes, spheroplasting, PEG 1000-mediated transformation, biolistics, lithium acetate transformation, lithium chloride transformation, and the like.

As used herein, the term "transformation" refers to a genetic alteration of a host cell resulting from the introduction of exogenous genetic material, e.g., nucleic acids, into the host cell.

As used herein, the term "gene" refers to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, gRNA, or micro RNA.

The term "expression cassette" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical but may be only substantially identical to a sequence of the gene from which it was derived. As explained herein, these substantially identical variants are specifically covered by reference to a specific nucleic acid sequence. One example of an expression cassette is a polynucleotide construct that includes a polynucleotide sequence encoding a polypeptide for use in the invention operably linked to a promoter, e.g., its native promoter, where the expression cassette is introduced into a heterologous microorganism. In some embodiments, an expression cassette includes a polynucleotide sequence encoding a polypeptide of the invention where the polynucleotide that is targeted to a position in the genome of a microorganism such that expression of the polynucleotide sequence is driven by a promoter that is present in the microorganism.

The term "host cell" as used in the context of this invention refers to a microorganism, such as yeast, and includes an individual cell or cell culture including a heterologous vector or heterologous polynucleotide as described herein. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a heterologous polynucleotide of the invention has been introduced, including by transformation, transfection, and the like.

As used herein, the term "promoter" refers to a nucleic acid control sequences that can direct transcription of a nucleic acid. A promoter includes necessary nucleic acid sequences near the start site of transcription. A promoter also optionally includes distal enhancer or repressor elements, which can be located as much as several thousand base pairs from the start site of transcription.

As used herein, the term "operably linked" refers to a functional linkage between nucleic acid sequences such that the sequences encode a desired function. For example, a coding sequence for a gene of interest, e.g., modified LgtA polypeptide, is in operable linkage with its promoter and/or regulatory sequences when the linked promoter and/or regulatory region functionally controls expression of the coding sequence. It also refers to the linkage between coding sequences such that they may be controlled by the same linked promoter and/or regulatory region; such linkage between coding sequences may also be referred to as being linked in frame or in the same coding frame. "Operably linked" also refers to a linkage of functional but non-coding sequences, such as an autonomous propagation sequence or origin of replication. Such sequences are in operable linkage when they are able to perform their normal function, e.g., enabling the replication, propagation, and/or segregation of a vector bearing the sequence in a host cell.

As used in this specification and the appended claims, the singular forms "a," "an," and "the" include plural reference unless the context clearly dictates otherwise.

As used herein, the term "about" is used herein to mean a value that is ±10% of the recited value.

BRIEF DESCRIPTION OF DRAWINGS

FIG. 2 is a schematic showing the lacto-n-neotetraose (LNnT) biosynthesis pathway in S. cerevisiae. The grey portions of the pathway indicate biosynthesis of native activated sugar donors, UDP-Galactose (UDP-Gal) and UDP-N-acetylglucosamine (UDP-GlcNAc). The green arrows indicate the desired steps to convert fed lactose to LNnT. LgtA, β-1,4-galactosyltransferase (LgtB), and K. lactis LAC12 permease are three heterologous enzymes required for LNnT biosynthesis. The red arrows indicate the steps for undesired longer polymer generation due to promiscuity of LgtA and LgtB. As is described in Example 1, below, K. lactis LAC12 permease is used to transport fed lactose in the media into the cytosol for LNnT biosynthesis.

FIG. 14 is a graph showing LNnT titer, as measured using mass spectrometry, among the 28×96-well plates of the Tier 1 assay described in Example 1, below.

DETAILED DESCRIPTION

Figure 1:
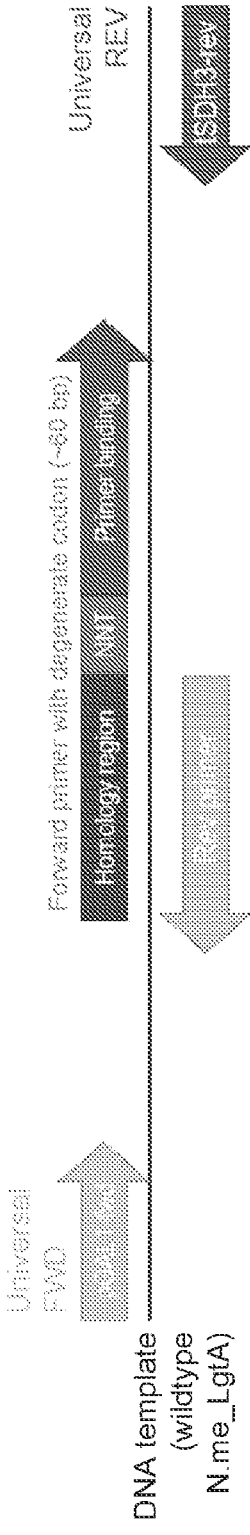
FIG. 1 is a schematic outlining the construction of the β-1,3-N-acetylglucosaminyltransferase (LgtA) single site mutation library described in Example 1, below. The library was constructed using polymerase chain reaction (PCR) techniques and NNT degenerate codons.

The present disclosure features variant β-1,3-N-acetylglucosaminyltransferase (LgtA) polypeptides, nucleic acids encoding the same, host cells capable of producing one or more HMOs, and methods for producing a human milk oligosaccharide (HMO) in a host cell, such as a yeast cell. The variant LgtA polypeptides described herein contain modifications, such as amino acid substitutions and/or deletions, which have presently been discovered to impart the polypeptide with enhanced specificity for its intended substrate in the biosynthetic pathway of a desired HMO relative to longer-chain oligosaccharides. This elevated substrate specificity gives rise to the ability to produce a target HMO with greater purity and overall yield relative to methods using a wild-type LgtA enzyme.

For example, expression of a variant LgtA polypeptide of the disclosure in a yeast strain capable of producing a desired HMO (e.g., a yeast strain that also expresses a β-1,4-galactosyltransferase (LgtB) and a lactose permease) may result not only in enhanced purity of the target HMO in comparison to a counterpart yeast strain that expresses a wild-type LgtA, but also improved HMO titer, as the variant LgtA polypeptides of the disclosure may reduce the expenditure of metabolic resources on the production of undesired longer-chain oligosaccharide byproducts.

The following sections provide a detailed description of the amino acid modifications (e.g., substitutions and deletions) that have been discovered to engender the enhanced substrate specificity described above, as well as how these variant LgtA polypeptides can be utilized to generate a desired HMO.

β-1,3-N-acetylglucosaminyltransferase Polypeptides

The variant LgtA polypeptides of the disclosure can be used to produce one or more of a variety of HMOs, including, without limitation, lacto-N-neotetraose (LNnT), lacto-N-tetraose (LNT), lacto-N-fucopentaose (LNFP) I, LNFP II, LNFP III, LNFP V, LNFP VI, lacto-N-difuco-hexaose (LNDFH) I, LNDFH II, lacto-N-hexaose (LNH), lacto-N-neohexaose (LNnH), fucosyllacto-N-hexaose (F-LNH) I, F-LNH II, difucosyllacto-N-hexaose (DF-LNH) I, DF-LNH II, difucosyllacto-N-neohexaose (DF-LNnH) I, difucosyl-para-lacto-N-hexaose (DF-para-LNH), difucosyl-para-lacto-N-neohexaose (DF-para-LNnH), trifucosyllacto- N-hexaose (TF-LNH), sialyllacto-N-tetraose (LST) a, LST b, LST c, disialyllacto-N-tetraose (DS-LNT), fucosyl-sialyl-lacto-N-tetraose (F-LST) a, F-LST b, fucosyl-sialyllacto-N-hexaose (FS-LNH), fucosyl-sialyllacto-N-neohexaose (FS-LNnH) I, and FDS-LNH II. LgtA enzymes catalyze the transfer of N-acetylglucosamine (GlcNAc) onto lactose as an acceptor substrate as part of the biosynthetic pathway of the HMO, LNnT. However, LgtA may also be responsible for formation of various byproducts, including long-chain derivatives built on LNnT, such as para-lacto-n-neohexaose (para-LNnH). Modification of the LgtA enzyme, specifically by mutating amino acids proximal to the enzyme's substrate binding pocket, is shown herein to improve production of one or more HMOs, including increasing overall HMO titer and reducing the production of undesired byproducts. The LgtA modifications described herein thus give rise to beneficial biosynthetic properties, as these modifications not only promote heightened yield of a target HMO, but also improve product purity.

In some embodiments, a variant polypeptide of the disclosure contains one or more amino acid substitutions relative to the wild-type LgtA amino acid sequence set forth in SEQ ID NO: 1. The amino acid substitution may occur, for example, at a residue selected from A27, P89, E170, G179, N180, I182, H183, N185, T186, M187, W206, A207, Q211, W213, V216, L229, V230, R233, H235, S240, K242, Y243, S244, Q247, I250, I254, Q255, A258, S265, S284, L288, K290, and E294 of SEQ ID NO: 1.

In some embodiments, the variant polypeptide includes an amino acid substitution at residue G179 of SEQ ID NO: 1. For example, the amino acid substitution at residue G179 of SEQ ID NO: 1 may substitute G179 with an amino acid including a cationic side chain at physiological pH. In some embodiments, the amino acid substitution at residue G179 of SEQ ID NO: 1 is a G179R substitution.

In some embodiments, the variant polypeptide includes an amino acid substitution at residue A27 of SEQ ID NO: 1. For example, the amino acid substitution at residue A27 of SEQ ID NO: 1 may substitute A27 with an amino acid including a hydrophobic, uncharged side chain at physiological pH. In some embodiments, the amino acid substitution at residue A27 of SEQ ID NO: 1 is an A27G substitution In some embodiments, the variant polypeptide includes an amino acid substitution at residue P89 of SEQ ID NO: 1. For example, the amino acid substitution at residue P89 of SEQ ID NO: 1 may substitute P89 with an amino acid including a polar, uncharged chain at physiological pH. In some embodiments, the amino acid substitution at residue P89 of SEQ ID NO: 1 is a P89T substitution.

In some embodiments, the variant polypeptide includes an amino acid substitution at residue E170 of SEQ ID NO: 1. For example, the amino acid substitution at residue E170 of SEQ ID NO: 1 may substitute E170 with an amino acid including a hydrophobic, uncharged side chain at physiological pH. In some embodiments, the amino acid substitution at residue E170 of SEQ ID NO: 1 is an E170L substitution.

In some embodiments, the variant polypeptide includes an amino acid substitution at residue N180 of SEQ ID NO: 1. For example, the amino acid substitution at residue N180 of SEQ ID NO: 1 may substitute N180 with an amino acid including an anionic side chain at physiological pH. In some embodiments, the amino acid substitution at residue N180 of SEQ ID NO: 1 is an N180D substitution. In some embodiments, the amino acid substitution at residue N180 of SEQ ID NO: 1 substitutes N180 with an amino acid including a hydrophobic, uncharged side chain at physiological pH. For example, the amino acid substitution at residue N180 of SEQ ID NO: 1 may be an N180A substitution.

In some embodiments, the variant polypeptide includes an amino acid substitution at residue I182 of SEQ ID NO: 1. In some embodiments, the amino acid substitution at residue I182 of SEQ ID NO: 1 substitutes I182 with an amino acid including a hydrophobic, uncharged side chain at physiological pH. For example, the amino acid substitution at residue I182 of SEQ ID NO: 1 may be an I182Y substitution or an I182V substitution.

In some embodiments, the variant polypeptide includes an amino acid substitution at residue H183 of SEQ ID NO: 1. For example, the amino acid substitution at residue H183 of SEQ ID NO: 1 may be an H183P substitution. In some embodiments, the amino acid substitution at residue H183 of SEQ ID NO: 1 substitutes H183 with an amino acid including a polar, uncharged side chain at physiological pH. For example, the amino acid substitution at residue H183 of SEQ ID NO: 1 may be an H183S substitution.

In some embodiments, the variant polypeptide includes an amino acid substitution at residue N185 of SEQ ID NO: 1. For example, the amino acid substitution at residue N185 of SEQ ID NO: 1 may be an N185G substitution.

In some embodiments, the variant polypeptide includes an amino acid substitution at residue T186 of SEQ ID NO: 1. In some embodiments, the amino acid substitution at residue T186 of SEQ ID NO: 1 substitutes T186 with an amino acid including an anionic side chain at physiological pH. For example, the amino acid substitution at residue T186 of SEQ ID NO: 1 may be a T186D substitution. In another example, the amino acid substitution at residue T186 of SEQ ID NO: 1 may be a T186G substitution.

In some embodiments, the variant polypeptide includes an amino acid substitution at residue M187 of SEQ ID NO: 1. For example, the amino acid substitution at residue M187 of SEQ ID NO: 1 may be an M187P substitution.

In some embodiments, the variant polypeptide includes an amino acid substitution at residue W206 of SEQ ID NO: 1. The amino acid substitution at residue W206 of SEQ ID NO: 1 may substitute W206 with an amino acid including a polar, uncharged side chain at physiological pH. For example, the amino acid substitution at residue W206 of SEQ ID NO: 1 may be a W206N substitution.

In some embodiments, the variant polypeptide includes an amino acid substitution at residue A207 of SEQ ID NO: 1. In some embodiments, the amino acid substitution at residue A207 of SEQ ID NO: 1 substitutes A207 with an amino acid including a hydrophobic, uncharged side chain at physiological pH. For example, the amino acid substitution at residue A207 of SEQ ID NO: 1 may be an A207V substitution.

In some embodiments, the variant polypeptide includes an amino acid substitution at residue Q211 of SEQ ID NO: 1. The amino acid substitution at residue Q211 of SEQ ID NO: 1 may substitute Q211 with an amino acid including a hydrophobic, uncharged side chain at physiological pH. For example, the amino acid substitution at residue Q211 of SEQ ID NO: 1 may be a Q211V substitution, a Q211I substitution, or a Q211L substitution. In some embodiments, the amino acid substitution at residue Q211 of SEQ ID NO: 1 is a Q211C substitution.

In some embodiments, the variant polypeptide includes an amino acid substitution at residue W213 of SEQ ID NO: 1. In some embodiments, the amino acid substitution at residue W213 of SEQ ID NO: 1 substitutes W213 with an amino acid including a polar, uncharged side chain at physiological pH. For example, the amino acid substitution at residue W213 of SEQ ID NO: 1 is a W213S substitution or a W213N substitution.

In some embodiments, the variant polypeptide includes an amino acid substitution at residue V216 of SEQ ID NO: 1. In some embodiments, the amino acid substitution at residue V216 of SEQ ID NO: 1 substitutes V216 with an amino acid including a hydrophobic, uncharged side chain at physiological pH. For example, the amino acid substitution at residue V216 of SEQ ID NO: 1 is a V216L substitution.

In some embodiments, the variant polypeptide includes an amino acid substitution at residue L229 of SEQ ID NO: 1. In some embodiments, the amino acid substitution at residue L229 of SEQ ID NO: 1 substitutes L229 with an amino acid including a hydrophobic, uncharged side chain at physiological pH. For example, the amino acid substitution at residue L229 of SEQ ID NO: 1 may be an L229A substitution. In some embodiments, the amino acid substitution at residue L229 of SEQ ID NO: 1 is an L229P substitution.

In some embodiments, the variant polypeptide includes an amino acid substitution at residue V230 of SEQ ID NO: 1. The amino acid substitution at residue V230 of SEQ ID NO: 1 may substitute V230 with an amino acid including an anionic side chain at physiological pH. For example, the amino acid substitution at residue V230 of SEQ ID NO: 1 is a V230D substitution. In some embodiments, the amino acid substitution at residue V230 of SEQ ID NO: 1 substitutes V230 with an amino acid including a hydrophobic, uncharged side chain at physiological pH. In some embodiments, the amino acid substitution at residue V230 of SEQ ID NO: 1 is a V230A substitution.

In some embodiments, the variant polypeptide includes an amino acid substitution at residue R233 of SEQ ID NO: 1. The amino acid substitution at residue R233 of SEQ ID NO: 1 may substitute R233 with an amino acid including a hydrophobic, uncharged side chain at physiological pH. For example, the amino acid substitution at residue R233 of SEQ ID NO: 1 may be an R233I substitution.

In some embodiments, the variant polypeptide includes an amino acid substitution at residue H235 of SEQ ID NO: 1. In some embodiments, the amino acid substitution at residue H235 of SEQ ID NO: 1 substitutes H235 with an amino acid including a cationic side chain at physiological pH. For example, the amino acid substitution at residue H235 of SEQ ID NO: 1 may be an H235R substitution.

In some embodiments, the variant polypeptide includes an amino acid substitution at residue S240 of SEQ ID NO: 1. The amino acid substitution at residue S240 of SEQ ID NO: 1 may substitute S240 with an amino acid including a polar, uncharged side chain at physiological pH. For example, the amino acid substitution at residue S240 of SEQ ID NO: 1 may be an S240N substitution. Furthermore, the amino acid substitution at residue S240 of SEQ ID NO: 1 may be an S240Y substitution.

In some embodiments, the variant polypeptide includes an amino acid substitution at residue K242 of SEQ ID NO: 1. In some embodiments, the amino acid substitution at residue K242 of SEQ ID NO: 1 substitutes K242 with an amino acid including an anionic side chain at physiological pH. For example, the amino acid substitution at residue K242 of SEQ ID NO: 1 may be a K242D substitution.

In some embodiments, the variant polypeptide includes an amino acid substitution at residue Y243 of SEQ ID NO: 1. The amino acid substitution at residue Y243 of SEQ ID NO: 1 may substitute Y243 with an amino acid including a polar, uncharged side chain at physiological pH. For example, the amino acid substitution at residue Y243 of SEQ ID NO: 1 may be a Y243S substitution. Furthermore, the amino acid substitution at residue Y243 of SEQ ID NO: 1 may be a Y243A substitution or a Y243L substitution. In some embodiments, the amino acid substitution at residue Y243 of SEQ ID NO: 1 substitutes Y243 with an amino acid including a cationic side chain at physiological pH. For example, the amino acid substitution at residue Y243 of SEQ ID NO: 1 may be a Y243R substitution.

In some embodiments, the variant polypeptide includes an amino acid substitution at residue S244 of SEQ ID NO: 1. In some embodiments, the amino acid substitution at residue S244 of SEQ ID NO: 1 substitutes S244 with an amino acid including a polar, uncharged side chain at physiological pH. In some embodiments, the amino acid substitution at residue S244 of SEQ ID NO: 1 is an S244T substitution.

In some embodiments, the variant polypeptide includes an amino acid substitution at residue Q247 of SEQ ID NO: 1. For example, the amino acid substitution at residue Q247 of SEQ ID NO: 1 may be a Q247C substitution.

In some embodiments, the variant polypeptide includes an amino acid substitution at residue I250 of SEQ ID NO: 1. In some embodiments, the amino acid substitution at residue I250 of SEQ ID NO: 1 substitutes I250 with an amino acid including a hydrophobic, uncharged side chain at physiological pH. For example, the amino acid substitution at residue I250 of SEQ ID NO: 1 may be an I250F substitution.

In some embodiments, the variant polypeptide includes an amino acid substitution at residue I254 of SEQ ID NO: 1. In some embodiments, the amino acid substitution at residue I254 of SEQ ID NO: 1 substitutes I254 with an amino acid including a hydrophobic, uncharged side chain at physiological pH. For example, the amino acid substitution at residue I254 of SEQ ID NO: 1 may be an I254A substitution.

In some embodiments, the variant polypeptide includes an amino acid substitution at residue Q255 of SEQ ID NO: 1. The amino acid substitution at residue Q255 of SEQ ID NO: 1 may substitute Q255 with an amino acid including an anionic side chain at physiological pH. For example, the amino acid substitution at residue Q255 of SEQ ID NO: 1 may be a Q255D substitution.

In some embodiments, the variant polypeptide includes an amino acid substitution at residue A258 of SEQ ID NO: 1. In some embodiments, the amino acid substitution at residue A258 of SEQ ID NO: 1 substitutes A258 with an amino acid including an anionic side chain at physiological pH. For example, in some embodiments, the amino acid substitution at residue A258 of SEQ ID NO: 1 is an A258D substitution. Furthermore, in some embodiments, the amino acid substitution at residue A258 of SEQ ID NO: 1 is an A258R substitution.

In some embodiments, the variant polypeptide includes an amino acid substitution at residue S265 of SEQ ID NO: 1. In some embodiments, the amino acid substitution at residue S265 of SEQ ID NO: 1 substitutes S265 with an amino acid including a cationic side chain at physiological pH. In some embodiments, the amino acid substitution at residue S265 of SEQ ID NO: 1 is an S265H substitution.

In some embodiments, the variant polypeptide includes an amino acid substitution at residue S284 of SEQ ID NO: 1. In some embodiments, the amino acid substitution at residue S284 of SEQ ID NO: 1 substitutes S284 with an amino acid including a polar, uncharged side chain at physiological pH. In some embodiments, the amino acid substitution at residue S284 of SEQ ID NO: 1 is an S284Y substitution.

In some embodiments, the variant polypeptide includes an amino acid substitution at residue L288 of SEQ ID NO: 1. In some embodiments, the amino acid substitution at residue L288 of SEQ ID NO: 1 substitutes L288 with an amino acid including a polar, uncharged side chain at physiological pH. For example, the amino acid substitution at residue L288 of SEQ ID NO: 1 may be a L288S substitution.

In some embodiments, the variant polypeptide includes an amino acid substitution at residue K290 of SEQ ID NO: 1. In some embodiments, the amino acid substitution at residue K290 of SEQ ID NO: 1 substitutes K290 with an amino acid including a polar, uncharged side chain at physiological pH. In some embodiments, the amino acid substitution at residue K290 of SEQ ID NO: 1 is an K290Q substitution.

In some embodiments, the variant polypeptide includes an amino acid substitution at residue E294 of SEQ ID NO: 1. In some embodiments, the amino acid substitution at residue E294 of SEQ ID NO: 1 substitutes E294 with an amino acid including a polar, uncharged side chain at physiological pH. In some embodiments, the amino acid substitution at residue E294 of SEQ ID NO: 1 is an E294N substitution.

In some embodiments, the one or more amino acid substitutions include a deletion of residues 301-348 of SEQ ID NO: 1.

Illustrative variant LgtA polypeptide sequences that may be used in conjunction with the compositions and methods described herein include, without limitation, SEQ ID NO: 2-22, as well as functional variants thereof.

In some embodiments, the polypeptide has an amino acid sequence that is from about 85% to about 99.7% (e.g., 86%, 87%, 88%, 89%, 90%, 91%, 92%, 93%, 94%, 95%, 96%, 97%, 98%, 99%, and 99.5%) identical to the amino acid sequence of SEQ ID NO: 1. In some embodiments, the polypeptide has an amino acid sequence that is from about 90% to about 99.7% (e.g., 91%, 92%, 93%, 94%, 95%, 96%, 97%, 98%, 99%, and 99.5%) identical to the amino acid sequence of SEQ ID NO: 1. In some embodiments, the polypeptide has an amino acid sequence that is from about 95% to about 99.7% (e.g., 96%, 97%, 98%, 99%, and 99.5%) identical to the amino acid sequence of SEQ ID NO: 1.

In some embodiments, the variant LgtA polypeptide has an amino acid sequence that is at least 85% (e.g., at least 86%, 87%, 88%, 89%, 90%, 91%, 92%, 93%, 94%, 95%, 96%, 97%, 98%, or 99%) identical to the amino acid sequence of any one of SEQ ID NO: 2-22. In some embodiments, the variant LgtA polypeptide has an amino acid sequence that is at least 90% (e.g., at least 91%, 92%, 93%, 94%, 95%, 96%, 97%, 98%, or 99%) identical to the amino acid sequence of any one of SEQ ID NO: 2-22. In some embodiments, the variant LgtA polypeptide has an amino acid sequence that is at least 95% (e.g., at least 95%, 96%, 97%, 98%, or 99%) identical to the amino acid sequence of any one of SEQ ID NO: 2-22. In some embodiments, the variant LgtA polypeptide has an amino acid sequence of any one of SEQ ID NO: 2-22.

Yeast Genetically Modified to Produce Human Milk Oligo-saccharides

Provided herein are genetically modified yeast cells capable of producing one or more HMOs, including LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II, which express a variant LgtA polypeptide, e.g., any one of SEQ ID NO: 2-22 or another LgtA polypeptide having an amino acid substitution and/or deletion described herein.

In some embodiments, a yeast host cell is genetically variant in accordance with the invention to express variant LgtA polypeptide having an amino acid sequence of any one of SEQ ID NO: 2-22, or a biologically active variant that shares substantial identity with any one of SEQ ID NO: 2-22. In some embodiments, the variant has at least 70%, or at least 75%, 80%, or 85% identity to any one of SEQ ID NO: 2-22. In some embodiments, the variant has at least 90%, or at least 91%, 92%, 93%, or 94% identity to the amino acid sequence of any one of SEQ ID NO: 2-22. In some embodiments, the variant has at least 95% identity to any one of SEQ ID NO: 2-22.

LgtA activity can be assessed using any number of assays, including assays that evaluate the overall production of at least one HMO (e.g., LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II) by a yeast cell strain. For example, production yields may be calculated by quantifying sugar input into fermentation tanks and measuring residual levels of input sugars through ion exchange chromatography. Additional methods that may be used to assess HMO production include mass spectrometry, as is described in detail in Example 1, below.

In some embodiments, a variant LgtA polypeptide increases HMO production, e.g., LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II production, by at least 10%, at least 20%, at least 30%, at least 40%, at least 45%, at least 50%, or greater, when expressed in a host cell (e.g., a yeast strain described herein) as compared to a counterpart host cell of the same strain that expresses a wild-type LgtA polypeptide.

In some embodiments, a variant LgtA polypeptide increases the purity of the HMO produced, e.g., LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II), by at least 10%, at least 20%, at least 30%, at least 40%, at least 45%, at least 50%, or greater, when expressed in a host cell compared to a counterpart host cell of the same strain that expresses a wild-type LgtA polypeptide.

In some embodiments, a variant LgtA polypeptide decreases undesired byproduct (e.g., para-LNnH) production by at least 10%, at least 20%, at least 30%, at least 40%, at least 45%, at least 50%, or greater, when expressed in a host cell compared to a counterpart host cell of the same strain that expresses a wild-type LgtA polypeptide.

Yeast Cells Capable of Synthesizing HMO Precursors

In some embodiments, the provided genetically modified yeast cells are capable of producing the UDP-glucose HMO precursor. The activated sugar UDP-glucose is composed of a pyrophosphate group, the pentose sugar ribose, glucose, and the nucleobase uracil. UDP-glucose is natively produced by yeast cells, and its production levels can be increased with overexpression of, for example, phosphoglucomutase-2 (PGM2) or UTP glucose-1-phosphate uridylyltransferase (UGP1).

In some embodiments, the provided genetically modified yeast cells are capable of producing the UDP-galactose HMO precursor. The activated sugar UDP-galactose is composed of a pyrophosphate group, the pentose sugar ribose, galactose, and the nucleobase uracil. UDP-galactose is natively produced by yeast cells, and its production levels can be increased with overexpression of, for example, UDP-glucose-4-epimerase (GAL10).

In some embodiments, the provided genetically modified yeast cells are capable of producing the UDP-N-acetylglucosamine HMO precursor. The activated sugar UDP-N-acetylglucosamine consists of a pyrophosphate group, the pentose sugar ribose, N-acetylglucosamine, and the nucleobase uracil. UDP-N-acetylglucosamine is natively produced by yeast cells, and its production levels can be increased with expression of, for example, UDP-N-acetyl-glucosamine-diphosphorylase, or overexpression of, for example, glucosamine 6-phosphate N-acetyltransferase (GNA1) or phosphoacetylglucosamine mutase (PCM1).

In some embodiments, the provided genetically modified yeast cells are capable of producing the GDP-fucose HMO precursor. The activated sugar GDP-fucose consists of a pyrophosphate group, the pentose sugar ribose, fucose, and the nucleobase guanine. GDP-fucose is not natively produced by yeast cells, and its production can be enabled with the introduction of, for example, GDP-mannose 4,6-dehydratase, e.g., from *Escherichia coli*, and GDP-L-fucose synthase, e.g., from *Arabidopsis thaliana*.

In some embodiments, the provided genetically modified yeast cells are capable of producing the CMP-sialic acid HMO precursor. The activated sugar CMP-sialic acid consists of a pyrophosphate group, the pentose sugar ribose, sialic acid, and the nucleobase cytosine. CMP-sialic acid is not natively produced by yeast cells, and its production can be enabled with the introduction of, for example, CMP-Neu5Ac synthetase, e.g., from *Campylobacter jejuni*, sialic acid synthase, e.g., from *C. jejuni*, and UDP-N-acetylglucosamine 2-epimerase, e.g., from *C. jejuni*.

In some embodiments, the genetically modified yeast cells are capable of producing 2'-fucosyllactose. In addition to one or more heterologous nucleic acids encoding one or more of the aforementioned enzymes, the yeast can further include one or more heterologous nucleic acids encoding one or more of GDP-mannose 4,6-dehydratase, e.g., from *Escherichia coli*, GDP-L-fucose synthase, e.g., from *Arabidopsis thaliana*, α-1,2-fucosyltransferase, e.g., from *Helicobacter pylori*, and a fucosidase, e.g., an α-1,3-fucosidase. In some embodiments, the fucosyltransferase is from *Candidata moranbacterium* or *Pseudoalteromonas haloplanktis*.
Exemplary Yeast Strains In some embodiments, the genetically modified yeast cell is *Saccharomyces cerevisiae*. *Saccharomyces cerevisiae* strains suitable for genetic modification and cultivation to produce HMOs as disclosed herein include, but are not limited to, Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, CEN.PK, CEN.PK2, and AL-1. In some embodiments, the host cell is a strain of *Saccharomyces cerevisiae* selected from the group consisting of PE-2, CAT-1, VR-1, BG-1, CR-1, and SA-1. In certain aspects, the strain of *Saccharomyces cerevisiae* is PE-2. In certain embodiments, the strain of *Saccharomyces cerevisiae* is CAT-1. In some aspects, the strain of *Saccharomyces cerevisiae* is BG-1.

In some embodiments, the genetically modified yeast cell is *Saccharomyces cerevisiae*, and in addition to heterologous nucleic acids encoding one or more of the aforementioned enzymes, the yeast can further include a heterologous nucleic acid encoding a lactose transporter. In some embodiments, the lactose transporter is a lactose permease, e.g., LAC12 from *Kluyveromyces lactis* (SEQ ID NO: 23). In some embodiments, the lactose permease is from *Neurospora crassa*, e.g., Cdt2. In some embodiments, the lactose permease is from *Neofusicoccum parvum*, e.g., *Neofusicoccum parvum* UCRNP2 (1287680). Other suitable lactose permease sources include, for example and without limitation, *Scheffersomyces stipitis*, *Aspergillus lentulus*, *Emericella nidulans*, *Dacryopinax primogenitus*, *Microdochium bolleyi*, *Beauveria bassiana*, *Metarhizium robertsii*, *Phialocephala*, *Botryosphaeria parva*, *Moniliophthora roreri*, *Cordyceps fumosorosea*, *Diplodia seriata*, *Hypocrea jecorina*, and *Kluyveromyces marxianus*.

In some embodiments, in addition to heterologous nucleic acids encoding one or more of the aforementioned enzymes, the yeast may further include a LgtB polypeptide. In some embodiments, the LgtB polypeptide is from *Pasteurella multocida* (SEQ ID NO: 24).

In some embodiments, in addition to heterologous nucleic acids encoding one or more of the aforementioned enzymes, the yeast may further include a LgtB polypeptide. In some embodiments, the LgtB polypeptide is from *Neisseria gonorrhoeae* (SEQ ID NO: 25).

In some embodiments, the genetically modified yeast cell is *Kluyveromyces marxianus*. *Kluyveromyces marxianus* can provide several advantages for industrial production, including high temperature tolerance, acid tolerance, native uptake of lactose, and rapid growth rate. Beneficially, this yeast is genetically similar enough to *Saccharomyces cerevisiae* that similar or identical promoters and codon optimized genes can be used among the two yeast species. Furthermore, because *Kluyveromyces marxianus* has a native lactose permease, it is not necessary to introduce a heterologous nucleic acid to introduce this functionality. In some embodiments, at least a portion of the β-galactosidase gene (LAC4) required for metabolizing lactose is deleted in the genetically modified yeast. Thus, the modified *Kluyveromyces marxianus* strain is capable of importing lactose without consuming it. In some embodiments, the expression of the β-galactosidase gene in the genetically modified yeast is decreased relative to the expression in wild-type *Kluyveromyces marxianus*. Thus, the modified *Kluyveromyces marxianus* strain has reduced consumption of imported lactose.
Gene Expression Regulatory Elements In some embodiments, the genetically modified yeast cell includes a promoter that regulates the expression and/or stability of at least one of the one or more heterologous nucleic acids. In certain aspects, the promoter negatively regulates the expression and/or stability of the at least one heterologous nucleic acid. The promoter can be responsive to a small molecule that can be present in the culture medium of a fermentation of the modified yeast. In some embodiments, the small molecule is maltose or an analog or derivative thereof. In some embodiments, the small molecule is lysine or an analog or derivative thereof. Maltose and lysine can be attractive selections for the small molecule as they are relatively inexpensive, non-toxic, and stable.

In some embodiments, the promoter that regulates expression of the variant LgtA polypeptide, e.g., the polypeptide of any one of SEQ ID NO: 2-22, is a relatively weak promoter, or an inducible promoter. Illustrative promoters include, for example, lower-strength GAL pathway promoters, such as GAL10, GAL2, and GAL3 promoters. Additional illustrative promoters for expressing a LgtA polypeptide include constitutive promoters from *S. cerevisiae* native promoters, such as the promoter from the native TDH3 gene. In some embodiments, a lower strength promoter provides a decrease in expression of at least 25%, or at least 30%, 40%, or 50%, or greater, when compared to a GAL1 promoter.

Expression of a variant LgtA polypeptide, e.g., the polypeptide of any one of SEQ ID NO: 2-22 can be accomplished by introducing into the host cells a nucleic acid including a nucleotide sequence encoding the variant LgtA polypeptide under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell. Expression of a polypeptide of any one of SEQ ID NO: 2-22, or a variant thereof as described herein can be achieved by using parallel methodology.

Heterologous Nucleic Acids

In some embodiments, the one or more heterologous nucleic acids are introduced into the genetically modified yeast cells by using a gap repair molecular biology technique. In these methods, if the yeast has non-homologous end joining (NHEJ) activity, as is the case for *Kluyveromyces marxianus*, then the NHEJ activity in the yeast can be first disrupted in any of a number of ways. Further details related to genetic modification of yeast cells through gap repair can be found in U.S. Pat. No. 9,476,065, the full disclosure of which is incorporated by reference herein in its entirety for all purposes.

In some embodiments, the one or more heterologous nucleic acids are introduced into the genetically modified yeast cells by using one or more site-specific nucleases capable of causing breaks at designated regions within selected nucleic acid target sites. Examples of such nucleases include, but are not limited to, endonucleases, site-specific recombinases, transposases, topoisomerases, zinc finger nucleases, TAL-effector DNA binding domain-nuclease fusion proteins (TALENs), CRISPR/Cas-associated RNA-guided endonucleases, and meganucleases. Further details related to genetic modification of yeast cells through site specific nuclease activity can be found in U.S. Pat. No. 9,476,065, the full disclosure of which is incorporated by reference herein in its entirety for all purposes.

Nucleic Acid and Amino Acid Sequence Optimization

Described herein are specific genes and proteins useful in the methods, compositions, and organisms of the disclosure; however, it will be recognized that absolute identity to such genes is not necessary. For example, changes in a particular gene or polynucleotide including a sequence encoding a polypeptide or enzyme can be performed and screened for activity. Typically, such changes include conservative mutations and silent mutations. Such modified or mutated polynucleotides and polypeptides can be screened for expression of a functional enzyme using methods known in the art. Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989, Nucl Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, Nucl Acids Res. 24:216-8).

Those of skill in the art will recognize that, due to the degenerate nature of the genetic code, a variety of DNA molecules differing in their nucleotide sequences can be used to encode a given heterologous polypeptide of the disclosure. A native DNA sequence encoding the biosynthetic enzymes described above is referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties, e.g., charge or hydrophobicity. In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, Methods in Mol. Biol. 25:365-89).

Furthermore, any of the genes encoding the foregoing enzymes (or any others mentioned herein (or any of the regulatory elements that control or modulate expression thereof) can be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y.* spp.

*stipitis, Torulaspora pretoriensis, Issatchenkia orientalis, Schizosaccharomyces* spp., including *S. pombe, Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., *Salmonella* spp., or *X. dendrorhous.*

Techniques known to those skilled in the art may be suitable to identify additional homologous genes and homologous enzymes. Generally, analogous genes and/or analogous enzymes can be identified by functional analysis and will have functional similarities. Techniques known to those skilled in the art can be suitable to identify analogous genes and analogous enzymes. Techniques include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, e.g., as described herein or in Kiritani, K., Branched-Chain Amino Acids Methods Enzymology, 1970; then isolating the enzyme with said activity through purification; determining the protein sequence of the enzyme through techniques such as Edman degradation; design of PCR primers to the likely nucleic acid sequence; amplification of said DNA sequence through PCR; and cloning of said nucleic acid sequence. To identify homologous or similar genes and/or homologous or similar enzymes, suitable techniques also include comparison of data concerning a candidate gene or enzyme with databases such as BRENDA, KEGG, or MetaCYC. The candidate gene or enzyme can be identified within the above mentioned databases in accordance with the teachings herein.

Methods of Producing Human Milk Oligosaccharides

Also provided herein are methods of producing one or more HMOs (e.g., one or more of LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II). For example, provided herein are methods for producing LNnT. The methods may include, for example, providing a population of genetically modified yeast cells capable of producing one or more HMOs (e.g., LNnT, LNT, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, or FDS-LNH II), which genetically modified yeast cells are also genetically modified to express a variant LgtA polypeptide, e.g., a polypeptide having the amino acid sequence of any one of SEQ ID NO: 2-22 herein. Each yeast cell of the population may include a heterologous nucleic acid that encodes a variant LgtA polypeptide. In some embodiments, the population includes any of the yeast cells as disclosed herein and discussed above. The methods further include providing a culture medium and culturing the yeast cells in the culture medium under conditions suitable for the yeast cells to produce one or more HMOs.

The culturing can be performed in a suitable culture medium in a suitable container, including but not limited to a cell culture plate, a flask, or a fermentor. Any suitable fermentor may be used, including, but not limited to, a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric et al., in Ullmann's Encyclopedia of Industrial Chemistry, Sixth Edition, Volume 12, pages 398-473, Wiley-VCH Verlag GmbH & Co. KDaA, Weinheim, Germany. Further, the methods can be performed at any scale of fermentation known in the art to support industrial production of microbial products. Materials and methods for the maintenance and growth of cell cultures are well known to those skilled in the art of microbiology or fermentation science (see, for example, Bailey et al., Biochemical Engineering Fundamentals, second edition, McGraw Hill, New York, 1986). Consideration should be given to appropriate culture medium, pH, temperature, and requirements for aerobic, microaerobic, or anaerobic conditions, depending on the specific requirements of the host cell, the fermentation, and the process.

In some embodiments, the culturing is carried out for a period of time sufficient for the transformed population to undergo a plurality of doublings until a desired cell density is reached. In some embodiments, the culturing is carried out for a period of time sufficient for the host cell population to reach a cell density (OD600) of between 0.01 and 400 in the fermentation vessel or container in which the culturing is being carried out. The culturing can be carried out until the cell density is, for example, between 0.1 and 14, between 0.22 and 33, between 0.53 and 76, between 1.2 and 170, or between 2.8 and 400. In terms of upper limits, the culturing can be carried until the cell density is no more than 400, e.g., no more than 170, no more than 76, no more than 33, no more than 14, no more than 6.3, no more than 2.8, no more than 1.2, no more than 0.53, or no more than 0.23. In terms of lower limits, the culturing can be carried out until the cell density is greater than 0.1, e.g., greater than 0.23, greater than 0.53, greater than 1.2, greater than 2.8, greater than 6.3, greater than 14, greater than 33, greater than 76, or greater than 170. Higher cell densities, e.g., greater than 400, and lower cell densities, e.g., less than 0.1, are also contemplated.

In other embodiments, the culturing is carried for a period of time, for example, between 12 hours and 92 hours, e.g., between 12 hours and 60 hours, between 20 hours and 68 hours, between 28 hours and 76 hours, between 36 hours and 84 hours, or between 44 hours and 92 hours. In some embodiments, the culturing is carried out for a period of time, for example, between 5 days and 20 days, e.g., between 5 days and 14 days, between 6.5 days and 15.5 days, between 8 days and 17 days, between 9.5 days and 18.5 days, or between 11 days and 20 days. In terms of upper limits, the culturing can be carried out for less than 20 days, e.g., less than 18.5 days, less than 17 days, less than 15.5 days, less than 14 days, less than 12.5 day, less than 11 days, less than 9.5 days, less than 8 days, less than 6.5 days, less than 5 day, less than 92 hours, less than 84 hours, less than 76 hours, less than 68 hours, less than 60 hours, less than 52 hours, less than 44 hours, less than 36 hours, less than 28 hours, or less than 20 hours. In terms of lower limits, the culturing can be carries out for greater than 12 hours, e.g., greater than 20 hours, greater than 28 hours, greater than 36 hours, greater than 44 hours, greater than 52 hours, greater than 60 hours, greater than 68 hours, greater than 76 hours, greater than 84 hours, greater than 92 hours, greater than 5 days, greater than 6.5 days, greater than 8 days, greater than 9.5 days, greater than 11 days, greater than 12.5 days, greater than 14 days, greater than 15.5 days, greater than 17 days, or greater than 18.5 days. Longer culturing times, e.g., greater than 20 days, and shorter culturing times, e.g., less than 5 hours, are also contemplated.

In certain embodiments, the production of the one or more HMOs by the population of genetically modified yeast is inducible by an inducing compound. Such yeast can be manipulated with ease in the absence of the inducing compound. The inducing compound is then added to induce the production of one or more HMOs by the yeast. In other embodiments, production of the one or more HMOs by the yeast is inducible by changing culture conditions, such as, for example, the growth temperature, media constituents, and the like.

In certain embodiments, an inducing agent is added during a production stage to activate a promoter or to relieve repression of a transcriptional regulator associated with a biosynthetic pathway to promote production of one or more HMOs. In certain embodiments, an inducing agent is added during a build stage to repress a promoter or to activate a transcriptional regulator associated with a biosynthetic pathway to repress the production of one or more HMOs, and an inducing agent is removed during the production stage to activate a promoter to relieve repression of a transcriptional regulator to promote the production of one or more HMOs.

As discussed above, in some embodiments, the provided genetically modified yeast cell includes a promoter that regulates the expression and/or stability of the heterologous nucleic acid. Thus, in certain embodiments, the promoter can be used to control the timing of gene expression and/or stability of proteins, for example, an LgtA polypeptide, e.g., the polypeptide of any one of SEQ ID NO: 2-22 described herein.

In some embodiments, when fermentation of a genetically modified yeast cell is carried out in the presence of a small molecule, e.g., at least about 0.1% maltose or lysine, HMO production is substantially reduced or turned off. When the amount of the small molecule in the fermentation culture medium is reduced or eliminated, HMO production is turned on or increased. Such a system enables the use of the presence or concentration of a selected small molecule in a fermentation medium as a switch for the production of non-catabolic, e.g., LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II, compounds. Controlling the timing of non-catabolic compound production to occur only when production is desired redirects the carbon flux during the non-production phase into cell maintenance and biomass. This more efficient use of carbon can greatly reduce the metabolic burden on the host cells, improve cell growth, increase the stability of the heterologous genes, reduce strain degeneration, and/or contribute to better overall health and viability of the cells.

In some embodiments, the fermentation method includes a two-step process that utilizes a small molecule as a switch to affect the "off" and "on" stages. In the first step, i.e., the "build" stage, step (a) wherein production of the compound is not desired, the genetically modified yeast are grown in a growth or "build" medium including the small molecule in an amount sufficient to induce the expression of genes under the control of a responsive promoter, and the induced gene products act to negatively regulate production of the non-catabolic compound. After transcription of the fusion DNA construct under the control of a maltose-responsive or lysine-responsive promoter, the stability of the fusion proteins is post-translationally controlled. In the second step, i.e., the "production" stage, step (b), the fermentation is carried out in a culture medium including a carbon source wherein the small molecule is absent or in sufficiently low amounts such that the activity of a responsive promoter is reduced or inactive and the fusion proteins are destabilized. As a result, the production of the heterologous non-catabolic compound by the host cells is turned on or increased.

In some embodiments, the culture medium is any culture medium in which a genetically modified yeast capable of producing an HMO (e.g., LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II) can subsist, i.e., maintain growth and viability. In some embodiments, the culture medium is an aqueous medium including assimilable carbon, nitrogen, and phosphate sources. Such a medium can also include appropriate salts, minerals, metals, and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

In another embodiment, the method of producing one or more HMOs includes culturing host cells in separate build and production culture media. For example, the method can include culturing the genetically modified host cell in a build stage wherein the cell is cultured under non-producing conditions, e.g., non-inducing conditions, to produce an inoculum, then transferring the inoculum into a second fermentation medium under conditions suitable to induce production of one or more HMOs, e.g., inducing conditions, and maintaining steady state conditions in the second fermentation stage to produce a cell culture containing HMOs (e.g., LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II).

In some embodiments, the culture medium includes sucrose and lactose. In some embodiments, the carbon sources in the culture medium consist essentially of sucrose and lactose. In some embodiments, the carbon sources in the culture medium consist of sucrose and lactose. In some embodiments, the mass ratio of the sucrose to the lactose is selected to influence, adjust, or control the relative production rates of HMOs produced by the yeast cells. Controlling the composition of the produced HMOs in this way can advantageously permit the increasing of desired products, the decreasing of undesired products, the targeting of a desired product ratio, and the simplification of downstream product separation processes.

The mass ratio of the sucrose to the lactose in the culture medium can be, for example, between 3 and 40, e.g., between 3 and 25.6, between 7.6 and 29.2, between 11.2 and 32.8, between 14.8 and 36.4, or between 18.4 and 40. In terms of upper limits, the mass ratio of the sucrose to the lactose can be less than 40, e.g., less than 36.4, less than 32.8, less than 29.2, less than 25.6, less than 22, less than 18.4, less than 14.8, less than 11.2, or less than 7.6. In terms of lower limits, the mass ratio of the sucrose to the lactose can be greater than 3, e.g., greater than 7.6, greater than 11.2, greater than 14.8, greater than 18.4, greater than 22, greater than 25.6, greater than 29.2, greater than 32.8, or greater than 36.4. Higher ratios, e.g., greater than 40, and lower ratios, e.g., less than 3, are also contemplated.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. In some embodiments, the addition of a nitrogen source to the culture medium beyond a certain concentration is not advantageous for the growth of the yeast. As a result, the concentration of the nitrogen sources, in the culture medium can be less than about 20 g/L, e.g., less than about 10 g/L or less than about 5 g/L. Further, in some instances it may be desirable to allow the culture medium to become depleted of the nitrogen sources during culturing.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, e.g., greater than about 2.0 g/L or greater than about 5.0 g/L. In some embodiments, the addition of phosphate to the culture medium beyond certain concentrations is not advantageous for the growth of the yeast. Accordingly, the concentration of phosphate in the culture medium can be less than about 20 g/L, e.g., less than about 15 g/L or less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, e.g., greater than about 1.0 g/L or greater than about 2.0 g/L. In some embodiments, the addition of magnesium to the culture medium beyond certain concetrations is not advantageous for the growth of the yeast. Accordingly, the concentration of magnesium in the culture medium can be less than about 10 g/L, e.g, less than about 5 g/L or less than about 3 g/L. Further, in some instances it may be desirable to allow the culture medium to become depleted of a magnesium source during culturing.

In some embodiments, the culture medium can also include a biologically acceptable chelating agent, such as the dihydrate of trisodium citrate. In such instance, the concentration of a chelating agent in the culture medium can be greater than about 0.2 g/L, e.g., greater than about 0.5 g/L or greater than about 1 g/L. In some embodiments, the addition of a chelating agent to the culture medium beyond certain concentrations is not advantageous for the growth of the yeast. Accordingly, the concentration of a chelating agent in the culture medium can be less than about 10 g/L, e.g., less than about 5 g/L or less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, e.g., within the range of from about 20 mg/L to about 1000 mg/L or in the range of from about 50 mg/L to about 500 mg/L.

The culture medium can also include sodium chloride. Typically, the concentration of sodium chloride in the culture medium is within the range of from about 0.1 g/L to about 5 g/L, e.g., within the range of from about 1 g/L to about 4 g/L or in the range of from about 2 g/L to about 4 g/L.

In some embodiments, the culture medium can also include trace metals. Such trace metals can be added to the culture medium as a stock solution that, for convenience, can be prepared separately from the rest of the culture medium Typically, the amount of such a trace metals solution added to the culture medium is greater than about 1 ml/L, e.g., greater than about 5 mL/L, and more preferably greater than about 10 mL/L. In some embodiments, the addition of a trace metals to the culture medium beyond certain concentrations is not advantageous for the growth of the yeast. Accordingly, the amount of such a trace metals solution added to the culture medium can be less than about 100 mL/L, e.g., less than about 50 mL/L or less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, inositol, pyridoxine-HCl, thiamine-HCl, and combinations thereof. Such vitamins can be added to the culture medium as a stock solution that, for convenience, can be prepared separately from the rest of the culture medium In some embodiments, the addition of vitamins to the culture medium beyond certain concentrations is not advantageous for the growth of the yeast.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, e.g., during the production stage of the fermentation. In some embodiments, the culture may be supplemented with relatively high concentrations of such components at the outset, for example, of the production stage, so that growth and/or HMO production (e.g., HMO production) is supported for a period of time before additions are required. The preferred ranges of these components can be maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those of ordinary skill in the art, the rate of consumption of nutrient increases during culture as the cell density of the medium increases. Moreover, to avoid introduction of foreign microorganisms into the culture medium, addition can be performed using aseptic addition methods, as are known in the art. In addition, a small amount of anti-foaming agent may be added during the culture.

The temperature of the culture medium can be any temperature suitable for growth of the genetically modified yeast population and/or production of the one or more HMOs (e.g., one or more of LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II). For example, prior to inoculation of the culture medium with an inoculum, the culture medium can be brought to and maintained at a temperature in the range of from about 20° C. to about 45° C., e.g., to a temperature in the range of from about 25° C. to about 40° C. or of from about 28° C. to about 32° C. For example, the culture medium can be brought to and maintained at a temperature of 25° C., 25.5° C., 26° C., 26.5° C., 27° C., 27.5° C., 28° C., 28.5° C., 29° C., 29.5° C., 30° C., 30.5° C., 31° C., 31.5° C., 32° C., 32.5° C., 33° C., 33.5° C., 34° C., 34.5° C., 35° C., 35.5° C., 36° C., 36.5° C., 37° C., 37.5° C., 38° C., 38.5° C., 39° C., 39.5° C., or 40° C.

The pH of the culture medium can be controlled by the addition of acid or base to the culture medium In such cases when ammonia is used to control pH, it also conveniently serves as a nitrogen source in the culture medium. In some embodiments, the pH is maintained from about 3.0 to about 8.0, e.g., from about 3.5 to about 7.0 or from about 4.0 to about 6.5.

In some embodiments, the genetically modified yeast cells produce LNnT. The concentration of produced LNnT in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNnT in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNnT concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNnT can be 40 g/l or greater, e.g., 50 g/l, 60 g/l 70 g/l 80 g/l, 90 g/l e.g., or greater. For example, in some embodiments, concentrations of produced LNnT in the culture medium can be 100 g/l or greater. In some embodiments, expression of a variant LgtA, e.g., the polypeptide of any one of SEQ ID NO: 2-22, enhances production of LNnT, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNnT on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNnT on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of LNnT, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of LNnT, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, it is desirable to minimize the amount of LNnH produced by the genetically modified yeast cells relative the amount of LNnT produced. The mass of LNnH produced by the yeast cells per g of LNnT produced by the yeast cells can be, for example, between 0.001 g and 5 g e.g., between 0.01 g and 5 g, between 0.1 g and 5 g, between 0.2 g and 4.2 g, between 0.2 g and 2.6 g, between 0.6 g and 3 g, between 1 g and 3.4 g, between 1.4 g and 3.8 g, or between 1.8 g and 4.2 g. In terms of upper limits, the mass of LNnH produced per g of LNnT can be less than 4.2 g, e.g., less than 3.8 g, less than 3.4 g, less than 3 g, less than 2.6 g, less than 2.2 g, less than 1.8 g, less than 1.4 g, less than 1 g, less than 0.6 g, or less than 0.2 g. In terms of lower limits, the mass of LNnH produced per g of LNnT can be greater than 0.2 g, e.g., greater than 0.5 g, greater than 0.75 g, greater than 1 g, greater than 1.4 g, greater than 1.8 g, greater than 2.2 g, greater than 2.6 g, greater than 3 g, greater than 3.4 g, or greater than 3.8 g. Higher mass ratios, e.g., greater than 4.2 g/g, and lower mass ratios, e.g., less than 0.2 g/g, are also contemplated.

In some embodiments, the genetically modified yeast cells produce LNT. The concentration of produced LNT in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNT in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNT concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNT can be 40 g/l or greater, e.g., 50 g/l, 60 g/l 70 g/l 80 g/l, 90 g/l e.g., or greater. For example, in some embodiments, concentrations of produced LNT in the culture medium can be 100 g/l or greater. In some embodiments, expression of a modified LgtA, e.g., the polypeptide of any one of SEQ ID NO: 2-22, enhances production of LNT, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNT on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNT on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNT, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNT, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNFP I. The concentration of produced LNFP I in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNFP I in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNFP I concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNFP I can be 40 g/l or greater, e.g., 50 g/l, 60 g/l 70 g/l 80 g/l, 90 g/l e.g., or greater. For example, in some embodiments, concentrations of produced LNFP I in the culture medium can be 100 g/l or greater. In some embodiments, expression of a modified LgtA, e.g., the polypeptide of any one of SEQ ID NO: 2-22, enhances production of LNFP I, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNFP I on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNFP I on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNFP I, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNFP I, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNFP II. The concentration of produced LNFP II in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNFP II in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNFP II concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNFP II can be 40 g/l or greater, e.g., 50 g/l, 60 g/l 70 g/l 80 g/l, 90 g/l e.g., or greater. For example, in some embodiments, concentrations of produced LNFP II in the culture medium can be 100 g/l or greater. In some embodiments, expression of a modified LgtA, e.g., the polypeptide of any one of SEQ ID NO: 2-22, enhances production of LNFP II, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNFP II on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNFP II on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNFP II, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNFP II, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNFP III. The concentration of produced LNFP III in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNFP III in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNFP III concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNFP III can be 40 g/l or greater, e.g., 50 g/l, 60 g/l 70 g/l 80 g/l, 90 g/l e.g., or greater. For example, in some embodiments, concentrations of produced LNFP III in the culture medium can be 100 g/l or greater. In some embodiments, expression of a modified LgtA, e.g., the polypeptide of any one of SEQ ID NO: 2-22, enhances production of LNFP III, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNFP III on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNFP III on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNFP III, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNFP III, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNFP V. The concentration of produced LNFP V in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNFP V in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNFP V concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNFP V can be 40 g/l or greater, e.g., 50 g/l, 60 g/l 70 g/l 80 g/l, 90 g/l e.g., or greater. For example, in some embodiments, concentrations of produced LNFP V in the culture medium can be 100 g/l or greater. In some embodiments, expression of a modified LgtA, e.g., the polypeptide of any one of SEQ ID NO: 2-22, enhances production of LNFP V, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNFP V on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNFP V on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNFP V, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNFP V, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNFP VI. The concentration of produced LNFP VI in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNFP VI in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNFP VI concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNFP VI can be 40 g/l or greater, e.g., 50 g/l, 60 g/l 70 g/l 80 g/l, 90 g/l e.g., or greater. For example, in some embodiments, concentrations of produced LNFP V in the culture medium can be 100 g/l or greater. In some embodiments, expression of a modified LgtA, e.g., the polypeptide of any one of SEQ ID NO: 2-22, enhances production of LNFP VI, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNFP VI on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNFP VI on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNFP VI, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNFP VI, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNDFH I. The concentration of produced LNDFH I in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNDFH I in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNDFH I concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNDFH I can be 40 g/l or greater, e.g., 50 g/l, 60 g/l 70 g/l 80 g/l, 90 g/l e.g., or greater. For example, in some embodiments, concentrations of produced LNDFH I in the culture medium can be 100 g/l or greater. In some embodiments, expression of a modified LgtA, e.g., the polypeptide of any one of SEQ ID NO: 2-22, enhances production of LNDFH I, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNDFH I on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNDFH I on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNDFH I, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNDFH I, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNDFH II. The concentration of produced LNDFH II in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNDFH II in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNDFH II concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNDFH II can be 40 g/l or greater, e.g., 50 g/l, 60 g/l 70 g/l 80 g/l, 90 g/l e.g., or greater. For example, in some embodiments, concentrations of produced LNDFH II in the culture medium can be 100 g/l or greater. In some embodiments, expression of a modified LgtA, e.g., the polypeptide of any one of SEQ ID NO: 2-22, enhances production of LNDFH II, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNDFH II on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNDFH II on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNDFH II, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNDFH II, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNH. The concentration of produced LNH in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNH in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNH concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNH can be 40 g/l or greater, e.g., 50 g/l, 60 g/l 70 g/l 80 g/l, 90 g/l e.g., or greater. For example, in some embodiments, concentrations of produced LNH in the culture medium can be 100 g/l or greater. In some embodiments, expression of a modified LgtA, e.g., the polypeptide of any one of SEQ ID NO: 2-22, enhances production of LNH, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNH on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNH on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNH, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNH, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce LNnH. The concentration of produced LNnH in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LNnH in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LNnH concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LNnH can be 40 g/l or greater, e.g., 50 g/l, 60 g/l 70 g/l 80 g/l, 90 g/l e.g., or greater. For example, in some embodiments, concentrations of produced LNnH in the culture medium can be 100 g/l or greater. In some embodiments, expression of a modified LgtA, e.g., the polypeptide of any one of SEQ ID NO: 2-22, enhances production of LNnH, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LNnH on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LNnH on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a modified LgtA polypeptide, e.g., the polypeptide of any one of SEQ ID NO: 2-22, enhances production of LNnH, compared to a counterpart control strain that is not modified to express the modified LgtA, by at least 5%, or at least 10%, 20%, 30%, 40%, 50%, 60%, 70%, 80%, 90%, 100%, or greater, compared to the control. In some embodiments, expression of a modified LgtA polypeptide, e.g., the polypeptide of any one of SEQ ID NO: 2-22, enhances production of LNnH, compared to a counterpart control strain that is not modified to express the modified LgtA, by at least 5%, or at least 10%, 20%, 30%, 40%, 50%, 60%, 70%, 80%, 90%, 100%, or greater, compared to the control.

In some embodiments, the genetically modified yeast cells produce F-LNH I. The concentration of produced F-LNH I in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced F-LNH I in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the F-LNH I concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced F-LNH I can be 40 g/l or greater, e.g., 50 g/l, 60 g/l 70 g/l 80 g/l, 90 g/l e.g., or greater. For example, in some embodiments, concentrations of produced F-LNH I in the culture medium can be 100 g/l or greater. In some embodiments, expression of a variant LgtA, e.g., the polypeptide of any one of SEQ ID NO: 2-22, enhances production of F-LNH I, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced F-LNH I on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of F-LNH I on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of F-LNH I, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of F-LNH I, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce F-LNH II. The concentration of produced F-LNH II in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced F-LNH II in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the F-LNH II concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced F-LNH II can be 40 g/l or greater, e.g., 50 g/l, 60 g/l 70 g/l 80 g/l, 90 g/l e.g., or greater. For example, in some embodiments, concentrations of produced F-LNH II in the culture medium can be 100 g/l or greater. In some embodiments, expression of a variant LgtA, e.g., the polypeptide of any one of SEQ ID NO: 2-22, enhances production of F-LNH II, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced F-LNH II on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of F-LNH II on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of F-LNH II, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of F-LNH II, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce DF-LNH I. The concentration of produced DF-LNH I in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced DF-LNH I in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the DF-LNH I concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced DF-LNH I can be 40 g/l or greater, e.g., 50 g/l, 60 g/l 70 g/l 80 g/l, 90 g/l e.g., or greater. For example, in some embodiments, concentrations of produced DF-LNH I in the culture medium can be 100 g/l or greater. In some embodiments, expression of a variant LgtA, e.g., the polypeptide of any one of SEQ ID NO: 2-22, enhances production of DF-LNH I, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced DF-LNH I on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of DF-LNH I on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of DF-LNH I, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of DF-LNH I, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce DF-LNH II. The concentration of produced DF-LNH II in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced DF-LNH II in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the DF-LNH II concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced DF-LNH II can be 40 g/l or greater, e.g., 50 g/l, 60 g/l 70 g/l 80 g/l, 90 g/l e.g., or greater. For example, in some embodiments, concentrations of produced DF-LNH II in the culture medium can be 100 g/l or greater. In some embodiments, expression of a variant LgtA, e.g., the polypeptide of any one of SEQ ID NO: 2-22, enhances production of DF-LNH II, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced DF-LNH II on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of DF-LNH II on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of DF-LNH II, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of DF-LNH II, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce DF-LNnH. The concentration of produced DF-LNnH in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced DF-LNnH in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the DF-LNnH concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced DF-LNnH can be 40 g/l or greater, e.g., 50 g/l, 60 g/l 70 g/l 80 g/l, 90 g/l e.g., or greater. For example, in some embodiments, concentrations of produced DF-LNnH in the culture medium can be 100 g/l or greater. In some embodiments, expression of a variant LgtA, e.g., the polypeptide of any one of SEQ ID NO: 2-22, enhances production of DF-LNnH, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced DF-LNnH on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of DF-LNnH on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of DF-LNnH, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of DF-LNnH, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce DF-para-LNH. The concentration of produced DF-para-LNH in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced DF-para-LNH in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the DF-para-LNH concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced DF-para-LNH can be 40 g/l or greater, e.g., 50 g/l, 60 g/l 70 g/l 80 g/l, 90 g/l e.g., or greater. For example, in some embodiments, concentrations of produced DF-para-LNH in the culture medium can be 100 g/l or greater. In some embodiments, expression of a variant LgtA, e.g., the polypeptide of any one of SEQ ID NO: 2-22, enhances production of DF-para-LNH, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced DF-para-LNH on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of DF-para-LNH on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of DF-para-LNH, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of DF-para-LNH, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce DF-para-LNnH. The concentration of produced DF-para-LNnH in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced DF-para-LNnH in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the DF-para-LNnH concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced DF-para-LNnH can be 40 g/l or greater, e.g., 50 g/l, 60 g/l 70 g/l 80 g/l, 90 g/l e.g., or greater. For example, in some embodiments, concentrations of produced DF-para-LNnH in the culture medium can be 100 g/l or greater. In some embodiments, expression of a variant LgtA, e.g., the polypeptide of any one of SEQ ID NO: 2-22, enhances production of DF-para-LNnH, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced DF-para-LNnH on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of DF-para-LNnH on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of DF-para- LNnH, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of DF-para-LNnH, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce TF-LNH. The concentration of produced TF-LNH in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced TF-LNH in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the TF-LNH concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced TF-LNH can be 40 g/l or greater, e.g., 50 g/l, 60 g/l 70 g/l 80 g/l, 90 g/l e.g., or greater. For example, in some embodiments, concentrations of produced TF-LNH in the culture medium can be 100 g/l or greater. In some embodiments, expression of a variant LgtA, e.g., the polypeptide of any one of SEQ ID NO: 2-22, enhances production of TF-LNH, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced TF-LNH on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of TF-LNH on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of TF-LNH, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of TF-LNH, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce LST a. The concentration of produced LST a in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LST a in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LST a concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LST a can be 40 g/l or greater, e.g., 50 g/l, 60 g/l 70 g/l 80 g/l, 90 g/l e.g., or greater. For example, in some embodiments, concentrations of produced LST a in the culture medium can be 100 g/l or greater. In some embodiments, expression of a variant LgtA, e.g., the polypeptide of any one of SEQ ID NO: 2-22, enhances production of LST a, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LST a on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LST a on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of LST a, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of LST a, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce LST b. The concentration of produced LST b in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, concentration of produced LST b in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LST b concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LST b can be 40 g/l or greater, e.g., 50 g/l, 60 g/l 70 g/l 80 g/l, 90 g/l e.g., or greater. For example, in some embodiments, concentrations of produced LST b in the culture medium can be 100 g/l or greater. In some embodiments, expression of a variant LgtA, e.g., the polypeptide of any one of SEQ ID NO: 2-22, enhances production of LST b, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LST b on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LST b on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of LST b, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of LST b, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce LST c. The concentration of produced LST c in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced LST c in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the LST c concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced LST c can be 40 g/l or greater, e.g., 50 g/l, 60 g/l 70 g/l 80 g/l, 90 g/l e.g., or greater. For example, in some embodiments, concentrations of produced LST c in the culture medium can be 100 g/l or greater. In some embodiments, expression of a variant LgtA, e.g., the polypeptide of any one of SEQ ID NO: 2-22, enhances production of LST c, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced LST c on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of LST c on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of LST c, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of LST c, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce DS-LNT. The concentration of produced DS-LNT in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced DS-LNT in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the DS-LNT concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced DS-LNT can be 40 g/l or greater, e.g., 50 g/l, 60 g/l 70 g/l 80 g/l, 90 g/l e.g., or greater. For example, in some embodiments, concentrations of produced DS-LNT in the culture medium can be 100 g/l or greater. In some embodiments, expression of a variant LgtA, e.g., the polypeptide of any one of SEQ ID NO: 2-22, enhances production of DS-LNT, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced DS-LNT on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of DS-LNT on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, or greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of DS-LNT, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of DS-LNT, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce F-LST a. The concentration of produced F-LST a in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced F-LST a in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the F-LST a concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced F-LST a can be 40 g/l or greater, e.g., 50 g/l, 60 g/l 70 g/l 80 g/l, 90 g/l e.g., or greater. For example, in some embodiments, concentrations of produced F-LST a in the culture medium can be 100 g/l or greater. In some embodiments, expression of a variant LgtA, e.g., the polypeptide of any one of SEQ ID NO: 2-22, enhances production of F-LST a, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced F-LST a on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of F-LST a on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of F-LST a, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of F-LST a, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce F-LST b. The concentration of produced F-LST b in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced F-LST b in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the F-LST b concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced F-LST b can be 40 g/l or greater, e.g., 50 g/l, 60 g/l 70 g/l 80 g/l, 90 g/l e.g., or greater. For example, in some embodiments, concentrations of produced F-LST b in the culture medium can be 100 g/l or greater. In some embodiments, expression of a variant LgtA, e.g., the polypeptide of any one of SEQ ID NO: 2-22, enhances production of F-LST b, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced F-LST b on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of F-LST b on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of F-LST b, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of F-LST b, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce FS-LNH. The concentration of produced FS-LNH in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced FS-LNH in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the FS-LNH concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced FS-LNH can be 40 g/l or greater, e.g., 50 g/l, 60 g/l 70 g/l 80 g/l, 90 g/l e.g., or greater. For example, in some embodiments, concentrations of produced FS-LNH in the culture medium can be 100 g/l or greater. In some embodiments, expression of a variant LgtA, e.g., the polypeptide of any one of SEQ ID NO: 2-22, enhances production of FS-LNH, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced FS-LNH on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of FS-LNH on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of FS-LNH, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of FS-LNH, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce FS-LNnH. The concentration of produced FS-LNnH in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced FS-LNnH in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the FS-LNnH concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced FS-LNnH can be 40 g/l or greater, e.g., 50 g/l, 60 g/l 70 g/l 80 g/l, 90 g/l e.g., or greater. For example, in some embodiments, concentrations of produced FS-LNnH in the culture medium can be 100 g/l or greater. In some embodiments, expression of a variant LgtA, e.g., the polypeptide of any one of SEQ ID NO: 2-22, enhances production of FS-LNnH, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced FS-LNnH on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of FS-LNnH on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of FS-LNnH, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of FS-LNnH, compared to a counterpart control strain that is not modified to express the variant LgtA, by at least 5%, or at least 10%, 20%, 30%, 40%, 50%, 60%, 70%, 80%, 90%, 100%, or greater, compared to the control.

In some embodiments, the genetically modified yeast cells produce FDS-LNH II. The concentration of produced FDS-LNH II in the culture medium can be, for example, between 1 g/l and 125 g/l, e.g., between 5 g/l and 115 g/l, between 10 g/l and 110 g/l, between 15 g/l and 100 g/l, between 20 g/l and 100 g/l, or between 25 g/l and 100 g/l. In some embodiments, the concentration of produced FDS-LNH II in the culture medium can be, for example, between 5 g/l and 100 g/l, e.g., between 5 g/l and 50 to 90 g/l, between 10 g/l and 80 g/l, between 10 g/l and 75 g/l, between 20 g/l and 80 g/l, or between 20 g/l and 80 g/l. In some embodiments, the FDS-LNH II concentration can be greater than 5 g/l, e.g., greater than 8.5 g/l, greater than 12 g/l, greater than 15.5 g/l, greater than 19 g/l, greater than 22.5 g/l, greater than 26 g/l, greater than 29.5 g/l, greater than 33 g/l, or greater than 36.5 g/l. In some embodiments, concentrations of produced FDS-LNH II can be 40 g/l or greater, e.g., 50 g/l, 60 g/l 70 g/l 80 g/l, 90 g/l e.g., or greater. For example, in some embodiments, concentrations of produced FDS-LNH II in the culture medium can be 100 g/l or greater. In some embodiments, expression of a variant LgtA, e.g., the polypeptide of any one of SEQ ID NO: 2-22, enhances production of FDS-LNH II, compared to a counterpart control strain that is not modified to express the LgtA polypeptide, is enhanced by at least 5%, or at least 10%, 20%, 30%, 40%, 50%, 60%, 70%, 80%, 90%, 100%, or greater, compared to the control.

The yield of produced FDS-LNH II on the sucrose in the culture medium can be, for example, between 0.01 g/g and 0.4 g/g, e.g., between 0.01 g/g and 0.3 g/g, between 0.01 g/g and 0.2 g/g, between 0.02 g/g and 0.2 g/g, between 0.03 g/g and 0.2 g/g, between 0.04 g/g and 0.2 g/g, or between 0.04 g/g and 0.2 g/g. In terms of lower limits, the yield of FDS-LNH II on sucrose can be greater than 0.01 g/g, e.g., greater than 0.02 g/g, greater than 0.03 g/g, greater than 0.04 g/g, greater than 0.05 g/g, greater than 0.06 g/g, greater than 0.07 g/g, greater than 0.08 g/g, or greater than 0.09 g/g. Higher yields, e.g., greater than 0.1 g/g, or greater than 0.15, or greater than 0.2 g/g, are also contemplated. For example, in some embodiments, yields are at least 0.25 g/g, e.g., 0.25 g/g or 0.26 g/g, or greater. In some embodiments, expression of a variant LgtA polypeptide, e.g., the polypeptide of any one of SEQ ID NO: 2-22, enhances production of FDS-LNH II, compared to a counterpart control strain that is not modified to express the variant LgtA, by at least 5%, or at least 10%, 20%, 30%, 40%, 50%, 60%, 70%, 80%, 90%, 100%, or greater, compared to the control. In some embodiments, expression of a variant LgtA polypeptide, e.g., the polypeptide of any one of SEQ ID NO: 2-22, enhances production of FDS-LNH II, compared to a counterpart control strain that is not modified to express the variant LgtA, by at least 5%, or at least 10%, 20%, 30%, 40%, 50%, 60%, 70%, 80%, 90%, 100%, or greater, compared to the control.

Fermentation Compositions

Also provided are fermentation compositions including a population of genetically modified yeast cells. The yeast cells can include any of the yeast cells disclosed herein and discussed above. In some embodiments, the fermentation composition further includes at least one HMO (e.g., LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II) produced from the yeast cells. The at least one HMO in the fermentation composition can include, for example, 2'-fucosyllactose, difucosyllactose, 3-fucosyllactose, LNT, LNnT, para-LNnH, LNFP I, LNFP II, LNFP III, LNFP V, LNFP VI, LNDFH I, LNDFH II, LNH, LNnH, F-LNH I, F-LNH II, DF-LNH I, DF-LNH II, DF-LNnH, DF-para-LNH, DF-para-LNnH, TF-LNH, LST a, LST b, LST c, DS-LNT, F-LST a, F-LST b, FS-LNH, FS-LNnH I, FDS-LNH II, 3'-sialyllactose, or 6'-sialyllactose. In some embodiments, the fermentation composition includes at least two HMOs. The at least two HMOs in the fermentation composition can include, for example, LNnT and para-LNnH, 2'-fucosyllactose and difucosyllactose, 2'-fucosyllactose and 3-fucosyllactose, 2'-fucosyllactose and lacto-N-tetraose, 2'-fucosyllactose and lacto-N-neotetraose, 2'-fucosyllactose and 3'-sialyllactose, 2'-fucosyllactose and 6'-sialyllactose, difucosyllactose and 3-fucosyllactose, difucosyllactose and lacto-N-tetraose, difucosyllactose and lacto-N-neotetraose, difucosyllactose and 3'-sialyllactose, difucosyllactose and 6'-sialyllactose, 3-fucosyllactose and lacto-N-tetraose, 3-fucosyllactose and lacto-N-neotetraose, 3-fucosyllactose and 3'-sialyllactose, 3-fucosyllactose and 6'-sialyllactose, lacto-N-tetraose and lacto-N-neotetraose, lacto-N-tetraose and 3'-sialyllactose, lacto-N-tetraose and 6'-sialyllactose, lacto-N-neotetraose and 3'-sialyllactose, lacto-N-neotetraose and 6'-sialyllactose, or 3'-sialyllactose and 6'-sialyllactose.

In some embodiments, the fermentation composition includes at least three HMOs produced from the yeast cells. In some embodiments, the fermentation composition includes at least four HMOs produced from the yeast cells. In some embodiments, the fermentation composition includes at least five HMOs produced from the yeast cells. In some embodiments, the fermentation composition includes at least six HMOs produced from the yeast cells. In some embodiments, the fermentation composition includes at least seven HMOs produced from the yeast cells.

The mass fraction of lacto-N-neotetraose within the one or more produced HMOs can be, for example, between 0 and 50%, e.g., between 0 and 30%, between 5% and 35%, between 10% and 40%, between 15% and 45%, or between 20% and 40%. In terms of upper limits, the mass fraction of difucosyllactose in the HMOs can be less than 50%, e.g., less than 45%, less than 40%, less than 35%, less than 30%, less than 25%, less than 20%, less than 15%, less than 10%, or less than 5%.

Methods of Recovering Human Milk Oligosaccharides

Also provided are methods of recovering one or more HMOs (e.g., one or more of LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II)) from a fermentation composition. In some embodiments, the fermentation composition is any of the fermentation composition disclosed herein and described above. The method may include separating at least a portion of a population of yeast cells from a culture medium. In some embodiments, the separating includes centrifugation. In some embodiments, the separating includes filtration.

While some portion of the one or more HMOs (e.g., one or more of LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II) produced by the cells during fermentation can be expected to partition with the culture medium during the separation of the yeast cells from the medium, some of the HMOs can be expected to remain associated with the yeast cells. One approach to capturing this cell-associated product and improving overall recovery yields is to rinse the separated cells with a wash solution that is then collected.

The provided recovery methods further include contacting the separated yeast cells with a heated wash liquid. In some embodiments, the heated wash liquid is a heated aqueous wash liquid. In some embodiments, the heated wash liquid consists of water. In some embodiments, the heated wash liquid includes one or more other liquid or dissolved solid components.

The temperature of the heated aqueous wash liquid can be, for example, between 30° C. and 90° C., e.g., between 30° C. and 66° C., between 36° C. and 72° C., between 42° C. and 78° C., between 48° C. and 84° C., or between 54° C. and 90° C. In terms of upper limits, the wash temperature can be less than 90° C., e.g., less than 84° C., less than 78° C., less than 72° C., less than 66° C., less than 60° C., less than 54° C., less than 48° C., less than 42° C., or less than 36° C. In terms of lower limits, the wash temperature can be greater than 30° C., e.g., greater than 36° C., greater than 42° C., greater than 48° C., greater than 54° C., greater than 60° C., greater than 66° C., greater than 72° C., greater than 78° C., or greater than 84° C. Higher temperatures, e.g., greater than 90° C., and lower temperatures, e.g., less than 30° C., are also contemplated.

The method may further include, subsequent to the contacting of the separated yeast cells with the heated wash liquid, removing the wash liquid from the yeast cells. In some embodiments, the removed wash liquid is combined with the separated culture medium and further processesed to isolate the produced one or more HMOs (e.g., one or more of LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II). In some embodiments, the removed wash liquid and the separated culture medium are further processed independently of one another. In some embodiments, the removal of the wash liquid from the yeast cells includes cetrifugation. In some embodiments, the removal of the wash liquid from the yeast cells includes filtration.

The recovery yield can be such that, for at least one of the one or HMOs (e.g., one or more of LNnT, 2'-FL, 3-FL, DFL, LNT, LNFP I, LNFP II, LNFP III, LNFP V, LNFP VI, LNDFH I, LNDFH II, LNH, LNnH, F-LNH I, F-LNH II, DFLNH I, DFLNH II, DFLNnH, DF-para-LNH, DF-para-LNnH, TF-LNH, 3'-SL, 6'-SL, LST a, LST b, LST c, DS-LNT, F-LST a, F-LST b, FS-LNH, FS-LNnH I, or FDS-LNH II) produced from the yeast cells, the mass fraction of the produced at least one HMO recovered in the combined culture medium and wash liquid is, for example, between 70% and 100%, e.g., between 70% and 88%, between 73% and 91%, between 76% and 94%, between 79% and 97%, or between 82% and 100%. In terms of lower limits, the recovery yield of at least one of the one or more HMOs can be greater than 70%, e.g., greater than 73%, greater than 76%, greater than 79%, greater than 82%, greater than 85%, greater than 88%, greater than 91%, greater than 94%, or greater than 97%. The recovery yield can be such that, for each of the one or more HMOs produced from the yeast cells, the mass fraction recovered in the combined culture medium and wash liquid is, for example, between 70% and 100%, e.g., between 70% and 88%, between 73% and 91%, between 76% and 94%, between 79% and 97%, or between 82% and 100%. In terms of lower limits, the recovery yield of each of the one or more HMOs can be greater than 70%, e.g., greater than 73%, greater than 76%, greater than 79%, greater than 82%, greater than 85%, greater than 88%, greater than 91%, greater than 94%, or greater than 97%.

While the compositions and methods provided herein have been described with respect to a limited number of embodiments, one or more features from any of the embodiments described herein or in the figures can be combined with one or more features of any other embodiment described herein in the figures without departing from the scope of the disclosure. No single embodiment is representative of all aspects of the methods or compositions. In certain embodiments, the methods can include numerous steps not mentioned herein. In certain embodiments, the methods do not include any steps not enumerated herein. Variations and modifications from the described embodiments exist.

EXAMPLES

The following examples are put forth to provide those of ordinary skill in the art with a description of how the compositions and methods described herein may be used, made, and evaluated, and are intended to be purely exemplary of the invention and are not intended to limit the scope of what the inventors regard as their invention.

Example 1. Development of Variant β-1,3-N-acetylglucosaminyltransferases

This example describes a series of experiments conducted to evaluate the effects of various amino acid substitutions and deletions on the substrate specificity of β-1,3-N-acetyl-glucosaminyltransferase (LgtA). The sections that follow describe the types of amino acid modifications that were assessed, how these substitutions and deletions were introduced into LgtA, and how variant LgtA polypeptides containing one of more of these modifications can be used to improve the production and purity of a desired human milk oligosaccharide (HMO).

Development of a Structural Homology Model of LgtA

The full length LgtA protein sequence was uploaded to the homology modeling software YASARA (Yet Another Scientific Artificial Reality Application) in order to calculate a predicted three-dimensional structure of LgtA. Possible templates were identified by running 3 PSI-BLAST iterations to extract a position-specific scoring matrix (PSSM) from UniRef 90 (The Uniprot Consortium). The Protein Data Bank (PDB) was then searched for a structure matching the results of the PSI-BLAST iterations. The top five PDB templates (shown in Table 2, below) were then used for structure prediction. The 'Total score' in the second column of Table 2 is the product of the BLAST alignment score, the WHAT_CHECK (Hooft et al., 1996, Nature. 381 (6580): 272) quality score in the PDBFinder2 database (Joosten et al., 2011 Nucleic Acids Res. 39: D411-D419), and the target coverage. Analyzing each of these metrics serves to ensure that the template structures used are appropriate, even if the alignment score is relatively low. The quality score ranges from 0.000 to 1.000 for a perfect structural match.

The target sequence profile and a secondary structure prediction were created by (i) performing a PSI-BLAST multiple sequence alignment from 1,688 related UniRef 90 sequences, and subsequently (ii) inputting the template sequence profile into the PSI-Pred secondary structure prediction program to facilitate both alignment correction and protein loop modeling. Five initial homology models were built for each of the five starting templates. Finally, a more accurate hybrid model was generated using YASARA by scanning the top 25 model predictions. During this process, regions with low Z scores in the top scoring model were iteratively replaced with corresponding fragments from other structural models.

TABLE 2

The top 5 homology modeling templates

| Template | Total score | BLAST E-value | Align score | Cover | ID | Resolution |
|---|---|---|---|---|---|---|
| 1 | 122.13 | 4.00E−59 | 172 | 77% | 5HEA-C | 2.00 A |
| 2 | 87.83 | 2.00E−46 | 184 | 75% | 2Z86-B | 2.40 A |
| 3 | 81.21 | 9.00E−48 | 180 | 75% | 2Z87-A | 3.00 A |
| 4 | 76.79 | 1.00E−38 | 157 | 54% | 6P61-C | 1.95 A |
| 5 | 23.83 | 4.00E−06 | 37 | 96% | 6IWR-D | 2.60 A |

To identify the substrate binding sites in the homology model, the final hybrid model was aligned with the published structure of TarP, a UDP-N-acetylglucosamine transferase (PDB id: 6HNQ) that contains the cofactor UDP-GlcNAc and its putative substrate. The substrate mimics were used as an anchor for selecting residues that are within 8 Å of the substrate binding site on the TarP structure. The selected residues on the TarP structure were then aligned with the LgtA amino acid sequence using the Needle alignment algorithm (Madeira et al., 2019, Nucleic Acids Res. 46, W636-W641). This resulted in the identification of 37 aligned residues in the LgtA amino acid sequence. Using PyMOL, these 37 residues were then visualized in the LgtA homology model to identify 47 residues that structurally localized to the substrate binding site. In addition, 32 more surface residues that were near the substrate binding site were chosen for further analysis. In total, 95 unique residues were chosen to build a site saturation mutagenesis library for substrate specificity improvement.

Substrate Docking Model

Lacto-n-neotetraose (LNnT) was docked into the modeled LgtA structure to illustrate the beneficial mutation position relative to the product LNnT. Docking was performed by YASARA AutoDock based tool for molecular docking, whereas docking complexes were visualized by PyMOL. The PDB files of ligand and target enzymes were uploaded to YASARA, an AutoDock-based tool for molecular docking and virtual screening. This approach was used for analyzing dissociation constant (Kd) and binding energy of the docked complexes (Trott and Olson 2010; Krieger and Vriend 2014).

Screening Strain Background Design

Figure 13:
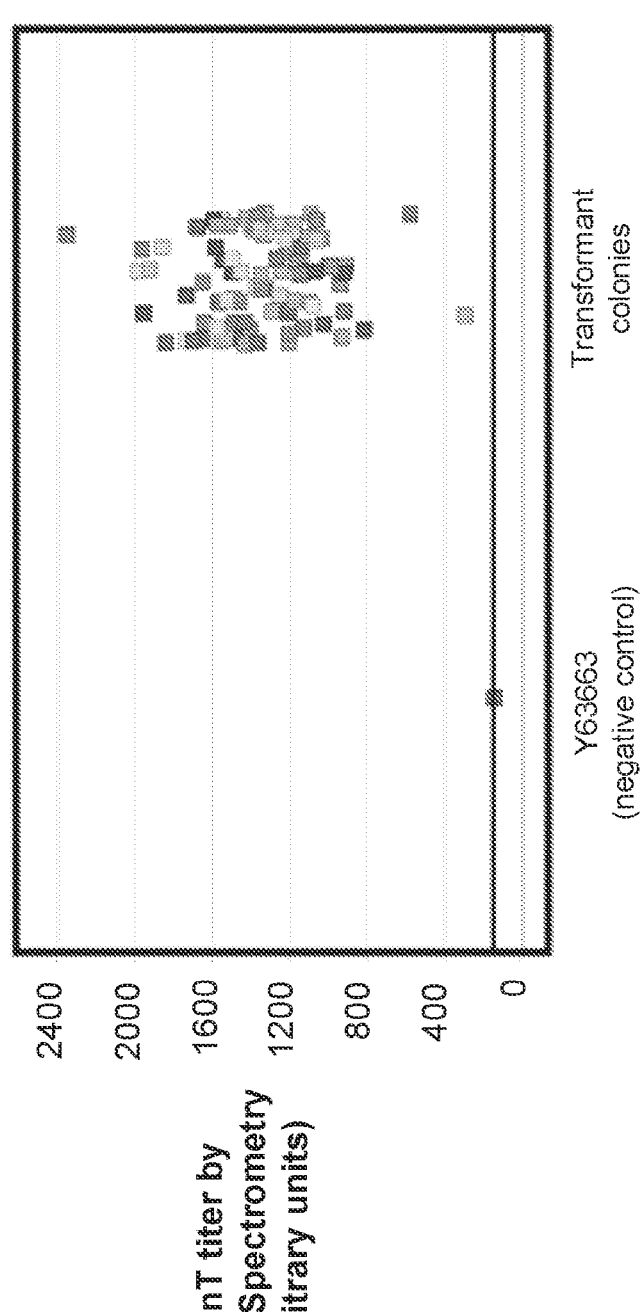
FIG. 13 is a graph showing LNnT titer, as measured using mass spectrometry, for the Y63663 strain described in Example 1, below, and the 95 colonies resulting from transformation using the landing pad described in FIG. 1.

The enzyme library was screened in Y63663, an *S. cerevisiae* strain designed to generate high titers of the unwanted byproduct para-LNnH if LgtA is expressed. Y63663 was derived from Y17025. Y63663 expresses β-1, 4-galactosyltransferase (LgtB) from *Pasteurella multocida* (SEQ ID NO: 24). Y63663 also over-expresses four native yeast genes (GFA1, GNA1, PCM1, and QRI1) for biosynthesis of UDP-GlcNAc, the co-substrate of LgtA. Finally, Y63663 does not express LgtA, and instead features a "landing pad" having pGAL1 and tSDH3 homology to facilitate library transformation. Prior to transformation of the enzyme library, this landing pad was validated for near 100%-integration efficiency (see FIG. 13), eliminating the need for a quality control step of colony PCR before screening for analyte titers. Strain Y64772 was a child of Y63663 with wild-type LgtA and was used as a control for the parent enzyme strain in all assays.

Library Construction

A site saturation mutagenesis (SSM) library was performed on a wild-type LgtA sequence from *Neisseria meningitidis* (SEQ ID NO: 1). The SSM library was constructed through PCR, using primers with NNT degenerate codon and the wild-type Neisseria meningitidis LgtA amino acid sequence as a template (see FIG. 1). NNT degenerate codon, which represents 15 of the 20 natural amino acids, was chosen for its coverage of amino acids with diverse physiochemical properties. Primers targeting the 95 residues identified for mutagenesis were designed and were ordered through Integrated DNA Technologies, Inc (IDT). For each residue targeted, two pieces of DNA were generated and co-transformed into a landing pad in the screening strain Y63663. This was done for each of the 95 residues targeted, leading to a total of 95 wells/transformations. The first DNA fragment was amplified by a universal FWD (forward) primer at pGAL1 and a reverse primer binding immediately upstream of the mutated codon. The second DNA fragment was amplified by a forward primer with a degenerate codon at the desired residue, with ~40 bp homology to the first DNA fragment to facilitate library transformation, and a universal REV (reverse) primer at tSDH3. The template DNA was a wild-type LgtA sequence flanked by pGAL1 and tSDH3. Upon co-transformation of both DNA fragments, an LgtA variant was integrated into the host strain genome, allowing for screening of enzyme variants. Resulting strains each carried a single variant of LgtA with a single amino acid change from the wild type. These strains were screened in tiered assays to gauge performance compared to the wild-type LgtA enzyme.

Microtiter Plate Growth Conditions

Pre-culture growth: Strains were incubated in an aerobic, pre-culture, 96-well, 1.1-ml microtiter shakeplate at 28° C., shaking at 1,000 RPM for 48 h to reach carbon exhaustion. Pre-culture media conditions were 360 μl/well of minimal complete media with 2% carbon (1.9% maltose+0.1% glucose) with 1 g/L Lysine.

Production growth: After pre-culture, strains were diluted ~10× (14.4 μl) into a 130 μl/well, 96-well, 1.6-ml microtiter shakeplate containing 4% sucrose+0.1% or 0.5% lactose. Production plates were incubated at 33.5° C. shaking at 1,000 RPM for 96 h.

Extraction and Analysis Conditions for Mass Spectrometry

After 4 days in production conditions, the carbon-exhausted whole cell broth was extracted in mass spectroscopy-grade methanol and $H_2O$. First, 225 μl/well of methanol (5× dilution) was added, with 15 minutes of shaking at 1500 RPM. Next, 900 μl/well of $H_2O$ (21X) was added, followed by shaking for an additional 5 minutes at 1200 RPM. Plates were centrifuged for 5 minutes at 2000 rpm, and 6 μl/well of the top layer were added to a new 1.1-ml plate containing 294 μl/well of 30% MeOH containing xylotriose ISTD (50×). The total dilution from whole cell broth is 880×.

Extraction and Analysis Conditions for Ion Chromatography

After 4 days in production conditions, the carbon-exhausted whole cell broth was extracted using a hot water method. Following the addition of 300 μl/well of sterile $H_2O$ (5×), plates were heated to 70° C. and mixed at 1000 RPM for 30 minutes. Plates were then centrifuged for 5 minutes at 2000 RPM. Finally, 25 μl/well of the supernatant is added to 175 μl/well of sterile $H_2O$ into a 1.6 ml plate (8×). Total dilution from whole cell broth was 40×.

This method was intended for quantitation of lacto-N-tetraose (LNT), lacto-N-neotetraose (LNnT), lactose, lactitol, lacto-N-neohexaose (LNnH), and lacto-N-triose II (LN-Triose II) titer, in g/kg, in samples of fermentation broth by ion chromatography. LNT, LNnT, LNTriose II, and lactose were quantitated by using external calibration and ion chromatography pulse amperometric detection with a Dionex CarboPac PA1 column.

Library Screening Using Tiered Assay

Tier 1 Library Screening

Figure 14:
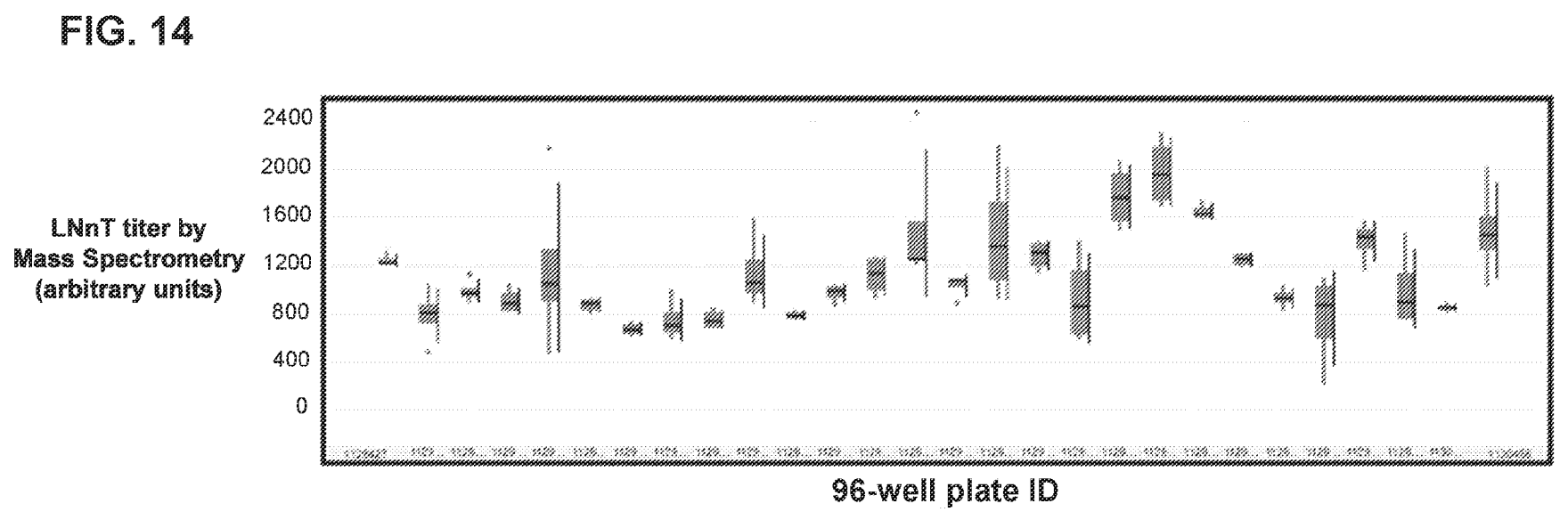

Following LgtA SSM library transformation and antibiotic selection on agar plates, the resulting colonies were submitted to a plate-based Tier 1 assay. For each well/transformation, 26 colonies were screened at n=1, equivalent to an SSM library coverage of 1.6×. This resulted in 28×96-well plates, each plate containing 4 replicates of the wild-type enzyme strain Y64772 as a control. Plates were incubated in the pre-culture and production conditions as described above, with 0.1% lactose in the production media. Following production, the resulting plates were measured for SSOD, an optical-based cell density assay, then extracted and submitted to analysis by mass spectrometry for relative quantification of analytes LNTrII and LNnT. Due to plate-to-plate variation in analyte quantification through the mass spectrometry method (see FIG. 14), all measurements on each plate were normalized to that plate's median titer values of the control, wild-type enzyme-expressing strain Y64772. Such manipulation allowed more confident comparison of variants on different 96-well plates.

Tier 2 Library Screening

Following Tier 1 assay results, a total of 184 variants were promoted and submitted to a plate-based Tier 2 assay. Each variant was replicated at n=4, resulting in eight 96-well plates, each having 4 replicates of the wild-type enzyme strain Y64772 as control. Plates were incubated in pre-culture and production conditions as described above, with 0.1% lactose in the production media. The resulting plates were measured for SSOD and were subsequently extracted and submitted to analysis by ion chromatography for quantification of analytes lactose, LNTrII, LNnT, and para-LNnH. Upon analyzing the results, most of the variants were categorized into two categories: potential false negatives and potential false positives. 48 variants in each category (96 total) were promoted to sequencing.

The 96 variants were sequenced as follows: The variable loci were amplified by PCR using the corresponding strains' genomic DNA with pGAL1-fwd and tSDH3-rev primers (FIG. 1). The presence of DNA fragments of expected lengths was verified by gel electrophoresis. These PCR products were cleaned and purified for sequencing. The resulting cleaned PCR products were submitted for sequencing. Following the analysis of sequencing data, variants with redundant mutations were removed to promote only unique variants to a Tier 3 screen.

Tier 3 Library Screening

Following the Tier 2 assay, a total of 30 unique variants of each category (60 total) were promoted for further testing. Prior to Tier 3, the top 60 variants were re-transformed into the mutagenesis screening strain, Y63663, using PCR products from prior sequencing processes. This was done to ensure that improvements observed in these enzyme variants are due to the mutations in the enzyme and not spontaneous mutations in the genome. These re-transformed strains were submitted to a plate-based Tier 3 assay. Each variant was tested in n=3 replicates, with 3 technical replicates of the wild-type enzyme strain Y64772 as control in each plate. The plates were incubated in pre-culture and production conditions as described above. The plate containing the 30 potential false negatives was diluted into two different production plates: one with 0.1% lactose and another with 0.5% lactose, but otherwise containing the standard production medium ingredients. The plate containing the 30 potential false positives were diluted into two production plates: one having 0.05% lactose and another having 0.1% lactose. These plates were incubated at 33.5° C. at 1,000 RPM for 96 hours. The resulting plates were measured for SSOD, an optical-based cell density assay, then extracted and submitted to quantification of analytes lactose, LNTrII, LNnT, and para-LNnH using ion chromatography.

Tier 4 Library Screening

Figure 2:
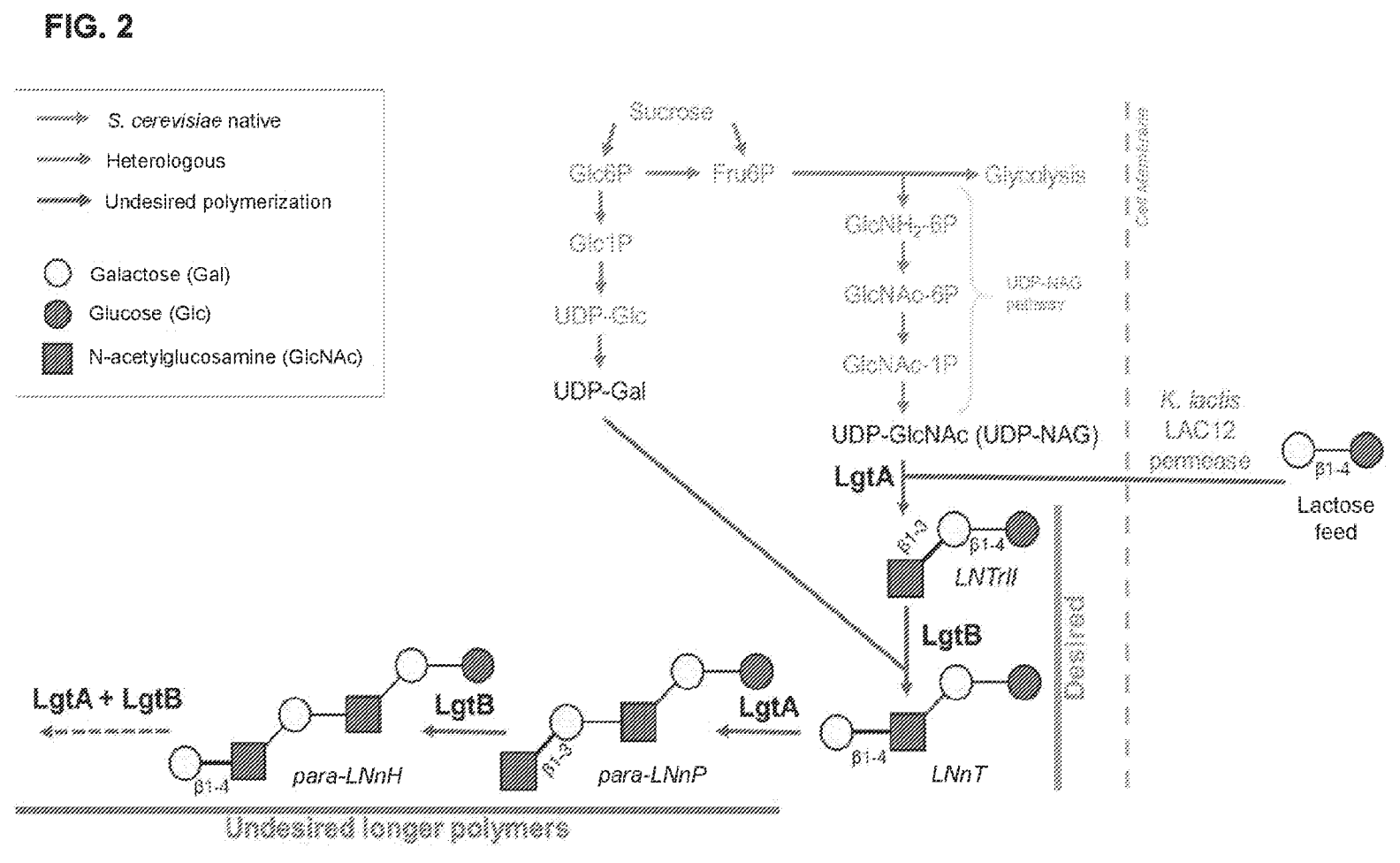

In this work, the biosynthesis pathway for LNnT was implemented in *S. cerevisiae* by co-expression of three heterologous enzymes: lactose permease (LAC12) (SEQ ID NO: 23), LgtA, and LgtB (SEQ ID NO: 24) (see Table 3 and FIG. 2). Native *S. cerevisiae* metabolism provides two of the three essential precursors UDP-Galactose (UDP-Gal) and UDP-N-acetylglucosamine (UDP-GlcNAc) to form the desired product LNnT (FIG. 2). Lactose was fed in the media and transported by Lac12 permease into the cytosol for conversion to LNnT. LgtA catalyzes the β-1,3 addition of GlcNAc onto lactose to produce Lacto-N-triose II (LNTrII), followed by the β-1,4 addition of Gal by LgtB to create LNnT.

TABLE 3

| Heterologous genes used in this study | | | |
|---|---|---|---|
| Gene | Species | Uniprot ID | Enzyme |
| LAC12 | *Kluyveromyces lactis* NRRL Y-1140 | P07921 | Lactose permease |
| LgtA | *Neisseria meningitidis* serogroup B (strain MC58) | Q8KI61 | β-1,3-N-acetyl-glucosaminyl-transferase |
| LgtB | *Pasteurella multocida* | F4ZLW1 | β-1,4-galactosyl-transferase |

It has been shown that the recombinant LgtA and LgtB glycosyltransferases are quite flexible with both the activated sugar donor and acceptor substrate (see, Blixt et al. 1999, Glycobiology. 9(10):1061-71; Li et al. 2016, Bioorganic & medicinal chemistry 24(8):1696-1705, Fischöder et al. 2019, Biotechnol. J., 14. ). Previous studies found that while the type of glycosidic linkage created by LgtA (β1,3) and LgtB (β1,4) is conserved, both enzymes are promiscuous in their donor and acceptor substrates. While LgtA predominantly transfers GlcNAc onto the lactose acceptor substrate, it can also transfer UDP-GalNAc to a variety of acceptor structures at moderate rates.

Figures 3A, 3B, 3C, 3D, 3E, 3F:
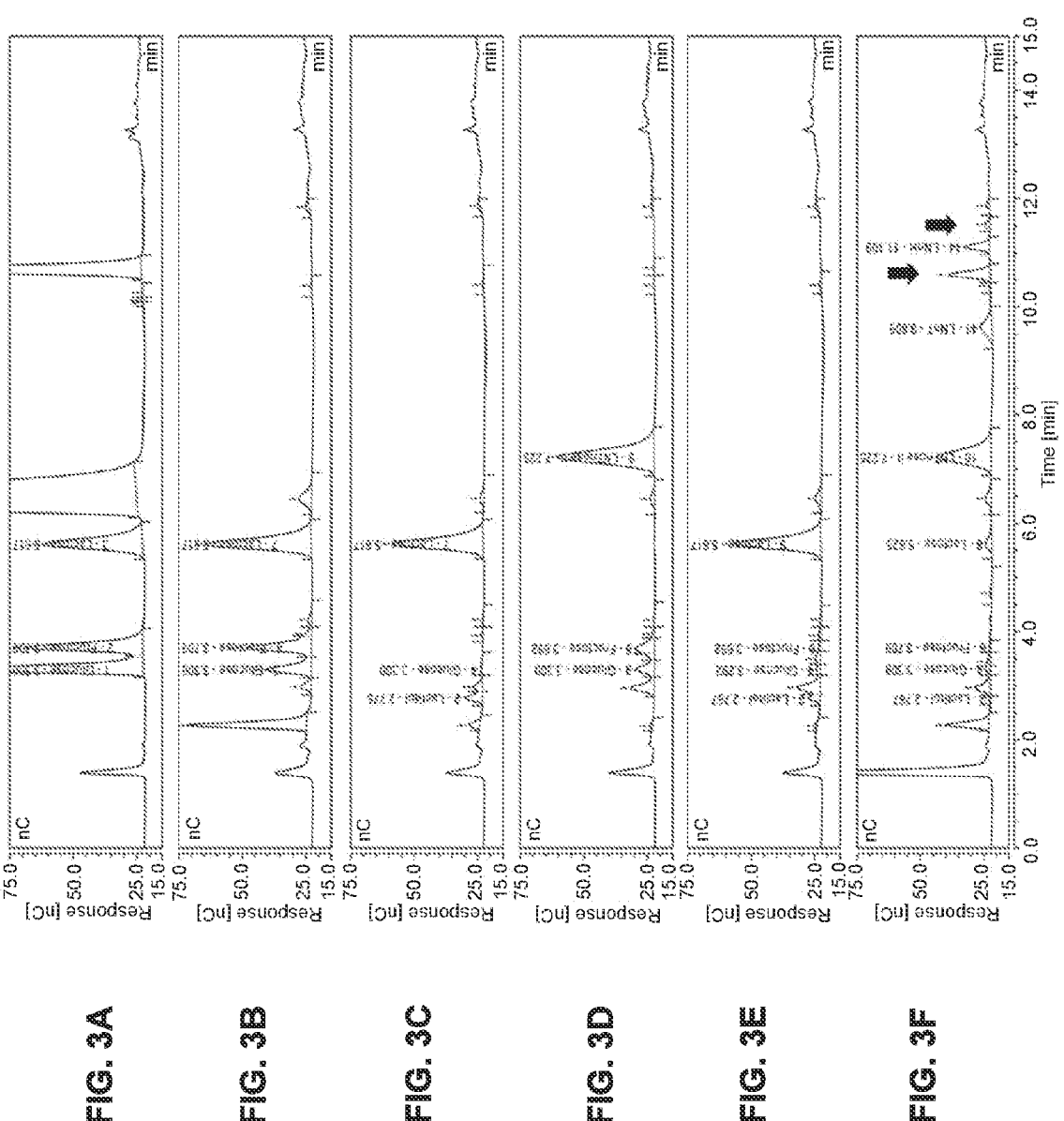
FIGS. 3A-3F show the ion chromatogram response traces for various samples described in Example 1, below, including: a media-only sample containing 4% sucrose and 0.1% lactose (FIG. 3A), a sample obtained from an S. cerevisiae Cen.PK113-7d strain without pathway engineering (FIG. 3B), a strain modified only to express the LAC12 lactose permease from K. lactis (SEQ ID NO: 23) (FIG. 3C), a strain modified to express KI LAC12 (SEQ ID NO: 23) and wild-type LgtA from N. meningitidis (SEQ ID NO: 1) (FIG. 3D), a strain modified to express KI LAC12 (SEQ ID NO: 23) and wild-type LgtB from P. multocida (SEQ ID NO: 24) (FIG. 3E), and a strain modified to express KI LAC12 (SEQ ID NO: 23), Nme LgtA (SEQ ID NO: 1), and Pmu LgtB (SEQ ID NO: 24) (FIG. 3F). The black arrows indicate two unknown products from the co-expression of wild-type LgtA and LgtB.

Strains were engineered with 1, 2, or all 3 of the heterologous pathway enzymes to determine byproduct generation profiles after growth in microtiter plates containing 0.1% lactose. Since standards for many of the possible impurities are difficult to obtain, visual analysis of ion chromatography traces was one of the methods used to evaluate product purity (FIG. 3). FIGS. 3A and 3B show the peaks present in media or wild-type yeast culture. The addition of lactose permease (FIG. 3C) to a wild-type strain results in the appearance of a lactitol peak, denoting successful lactose import via intracellular reduction, which likely occurs at a basal level in yeast. Expression of both lactose permease and LgtA converts all of the lactose to LNTrII (FIG. 3D). Expression of lactose permease and LgtB without LgtA does not result in any pathway-specific peaks (FIG. 3E). Finally, expression of all three enzymes produces LNnT, p-LNnH, and several additional unknown peaks between 10-12 minutes (FIG. 3F). The appearance of these peaks only in the presence of both LgtA and LgtB indicates that they are the product of promiscuous A/B activity combined. With the right set of screening metrics, it is still possible to select for more selective LgtA variants, even without identification of all unknown peaks.

Figure 4:
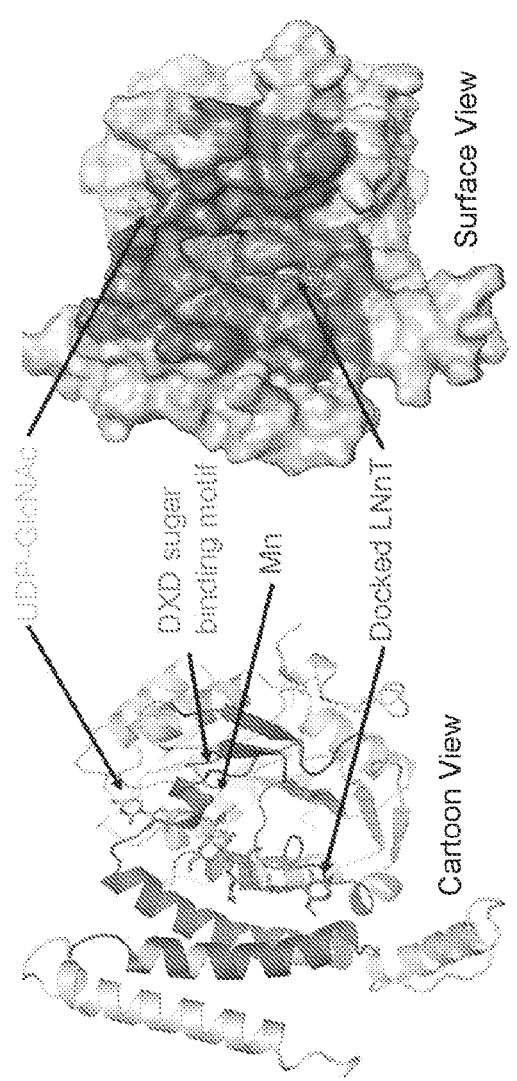
FIG. 4 shows a modeled LgtA structure illustrating residues selected for the mutagenesis experiments described in Example 1, below. The left side of the figure is a cartoon view of the LgtA model, and the right side of the figure is a surface view of the model. The blue region shows the residues selected for directed evolution to improve enzyme specificity. The green stick model represents docked UDP-GlcNAc and the orange stick model represents docked LNnT. The red-colored loop represents the DXD sugar binding motif and the purple sphere represents manganese.

Glycosyltransferase has a conserved structural fold despite its high diversity in sequence and acceptor molecules. Unfortunately, there is no available 3D-crystal structure for LgtA for selecting enzyme engineering residues. Therefore, YASARA software was used to simulate LgtA structure based on primary sequence via homology modeling. The modeled LgtA structure conserves a GT-A fold. There is an eight stranded β-sheet core flanked by α-helices and a small antiparallel β-sheet bridged via a signature metal-coordinating DXD motif-containing loop (FIG. 4). LNnT binds into a very shallow channel formed mostly by solvent accessible residues. There were 95 residues selected within 8 Å of, and on the surface area that is approximate to, the sugar acceptor binding site. A site saturation mutagenesis library with degenerate codon NNT was constructed over the selected region to generate diversity for changing substrate specificity (FIG. 4).

Figures 5A, 5B:
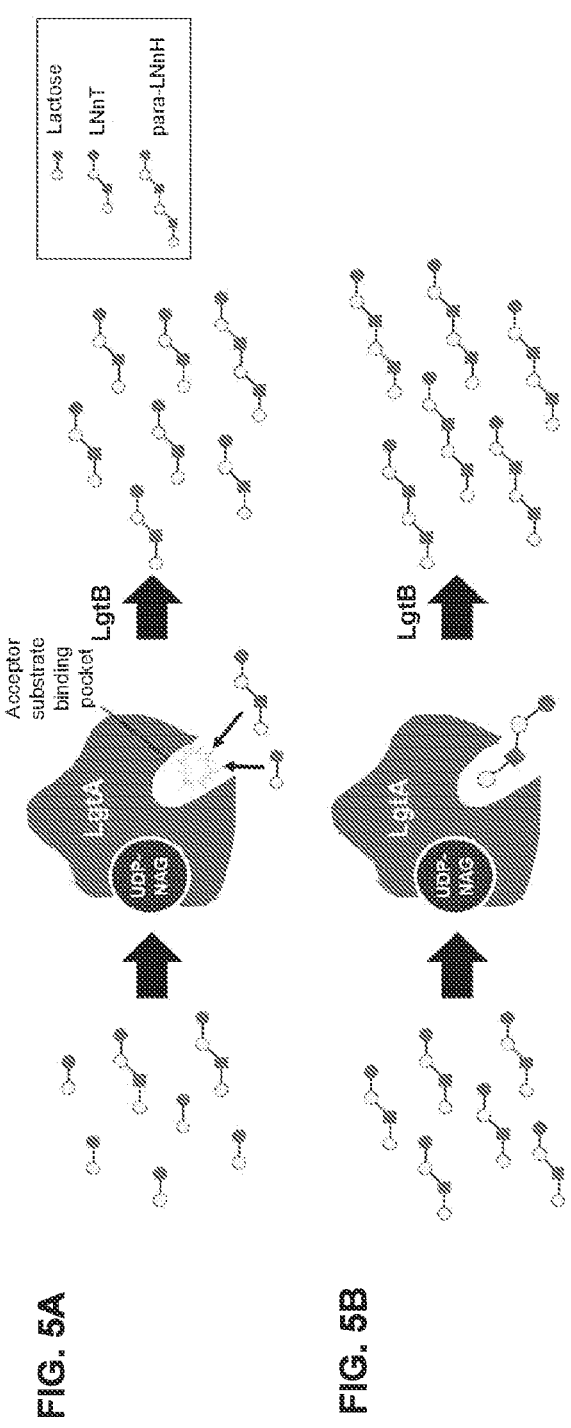
FIGS. 5A and 5B show an illustration of substrate competition for the LgtA binding pocket. As is shown in FIG. 5A, in the presence of lactose, lactose and LNnT compete for the LgtA binding site. Once lactose is depleted, LNnT more easily occupies the binding site, leading to higher production of para-LNnH (FIG. 5B). Accordingly, as is described in Example 1, below, the presence of lactose suppresses production of para-LNnH and longer chain byproducts, but as lactose is glycosylated by LgtA, this inhibition of longer chain HMO production is removed.

Screening LgtA variants for enhanced specificity for lactose poses a unique challenge due to numerous complications. First, only a select number of analytes can be readily quantified, namely lactose, LNTrII, LNnT, and para-LNnH, leading to only a narrow view on product profile. In particular, quantifying para-LNnP (the direct, 5-mer product of LgtA reacting on LNnT) is difficult, which led to the use of para-LNnH as proxy for specificity (FIG. 2). Second, LgtA reacts on the desired product LNnT, making interpretation of variants solely based on LNnT titer potentially misleading, as variants will convert LNnT to longer chain byproducts at varying rates. Third, substrate competition for the LgtA binding site skews the resulting product profile, requiring careful consideration of the surrounding reaction environment such as concentration of other analytes. An example of this phenomenon with lactose and LNnT is illustrated in FIGS. 5A and 5B. In FIG. 5A, presence of lactose leads to competition between lactose and LNnT for the LgtA acceptor substrate binding site, leading to lower production of para-LNnH. Conversely, in FIG. 5B, when lactose is not present (i.e. lactose is depleted), LNnT more easily binds to LgtA, resulting in a para-LNnH-rich product profile. Similarly, such competition likely occurs among other substrates of LgtA as well as substrates of LgtB. With these nuances in mind, a tiered screening scheme was developed in order to delineate the mutations in LgtA that are most likely to positively affect product profile.

Figure 6:
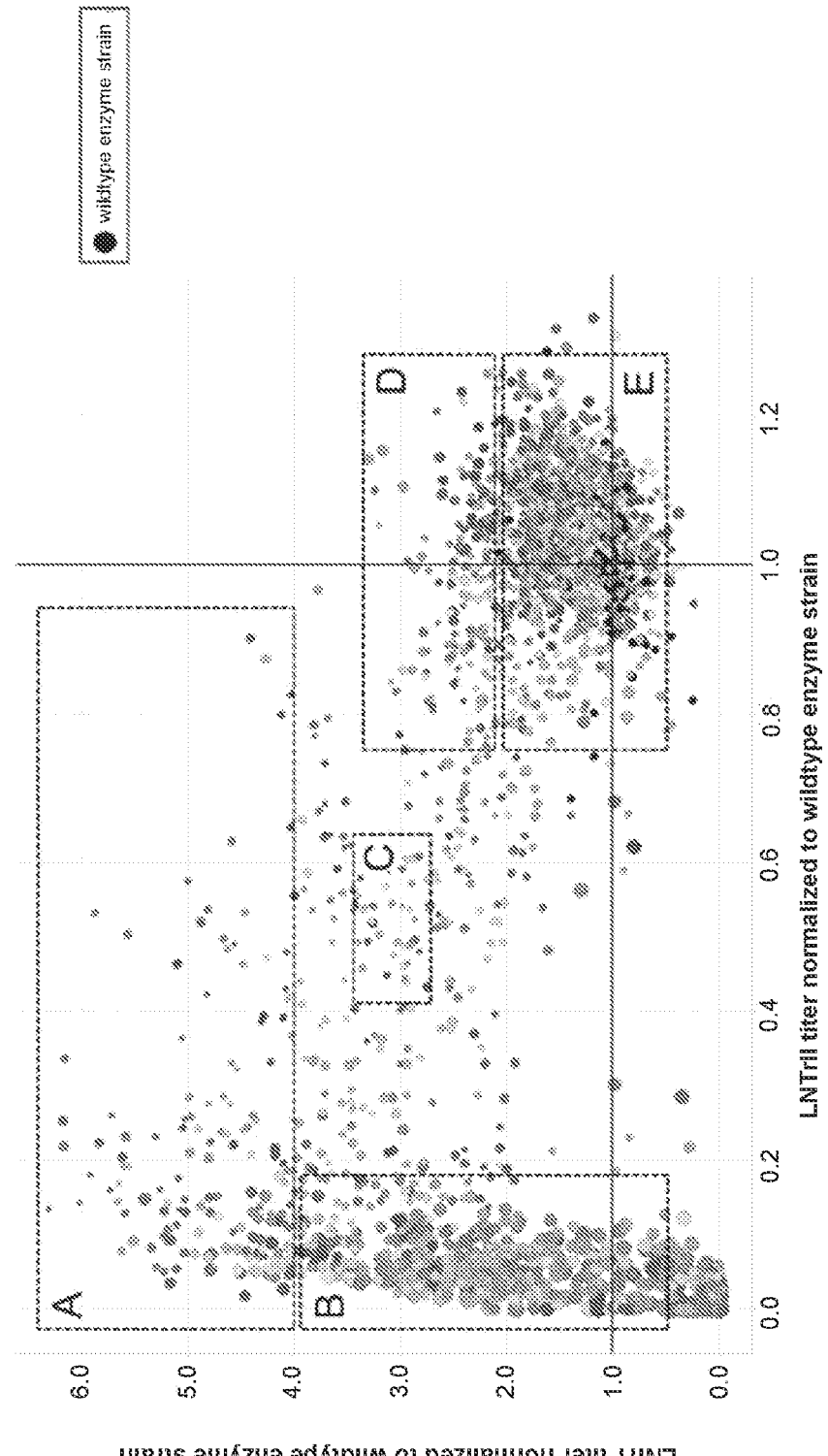
FIG. 6 shows the LNnT titer achieved from each of the 2,470 enzyme variants tested in the Tier 1 assay described in Example 1, below, as assessed using mass spectrometry. The data are based on n=4 replicates on each assay plate over 28 total plates. The size of the circles reflects relative SSOD. The solid black lines at x=1 and y=1 represent the normalized wild-type enzyme strain titers. The five boxes, A-E, outline the categories of the 184 total LgtA variants that were promoted to the Tier 2 assay described in Example 1. Box A: 141 variants with at least 4-fold LNnT titer improvement. Box B: 25 variants with moderate (2-4-fold) LNnT titer improvement and high cell density. Box C: 3 variants with high LNnT titer normalized to cell density. Box D: 7 variants with moderately improved LNnT but comparable LNTrII as wild type. Box E: 8 variants with wild type-like titers.

Following LgtA variant library transformation, resulting colonies were screened in the Tier 1 shakeplate assay. The colonies were grown in microtiter plates with 0.1% lactose and their resulting product profile measured by using mass spectrometry. Here, the analytes LNTrII and LNnT were quantified, and the result is shown in FIG. 6. Many variants show great promise, accumulating up to 6-fold higher LNnT titer compared to the wild-type enzyme-expressing strain.

Different classes of variants, as outlined by boxes A-E in FIG. 6, were promoted to the next tier of screening. All 141 LgtA variant strains in box A were promoted due to high LNnT titer. 25 variants were sampled from box B for their moderate (2~4-fold) improvement in LNnT titer as well as higher cell density compared to the wild-type, denoting more robust culture health. 3 variants were sampled and promoted from box C based on LNnT titer normalized to cell density, which denotes increased per cell productivity. 7 variants were sampled and promoted from box D for moderate improvement in LNnT titer but comparable LNTrII titer as wild type, potentially denoting a decreased specificity for further conversion of LNnT to longer chain oligosaccharides, but no decrease in activity on lactose. Finally, 8 variants were sampled from box E for their wild type-like LNnT and LNTrII titers, as a control denoting no change in LgtA activity or specificity. When sampling variants from boxes B-E, variants were chosen with the mutagenized residue in mind: for example, given two variants at G179 with similar performance, only one was selected. Multiple high performing variants at the same targeted residue were observed, but to maintain diversity of variants, promoting a single variant per targeted residue was prioritized. Ultimately, a total of 184 variants were promoted to Tier 2 analysis.

184 variants were screened at a higher replication of n=4 in a shakeplate Tier 2 assay using the ion chromatography method described above, providing quantification of residual lactose and para-LNnH in addition to LNTrII and LNnT. The strains were grown in microtiter plates with 0.1% lactose. Tier 2 results are plotted in FIG. 7, with residual lactose titer on the x-axis and para-LNnH titer on the y-axis. The x-axis represents an axis for activity: the lower the residual lactose titer, the more active the variant in converting lactose to LNTrII. The y-axis represents an axis for specificity: the lower the para-LNnH titer, the more specific the variant for lactose over LNnT as its substrate. Thus, the ideal variants lie in the bottom left corner of the plot, while accumulating high LNnT titer as shown by the size of data points. The ideal nature was not observed: that is, a variant able to deplete all available lactose and producing very little to non-detectable level of para-LNnH while accumulating high titers of LNnT.

Figure 7:
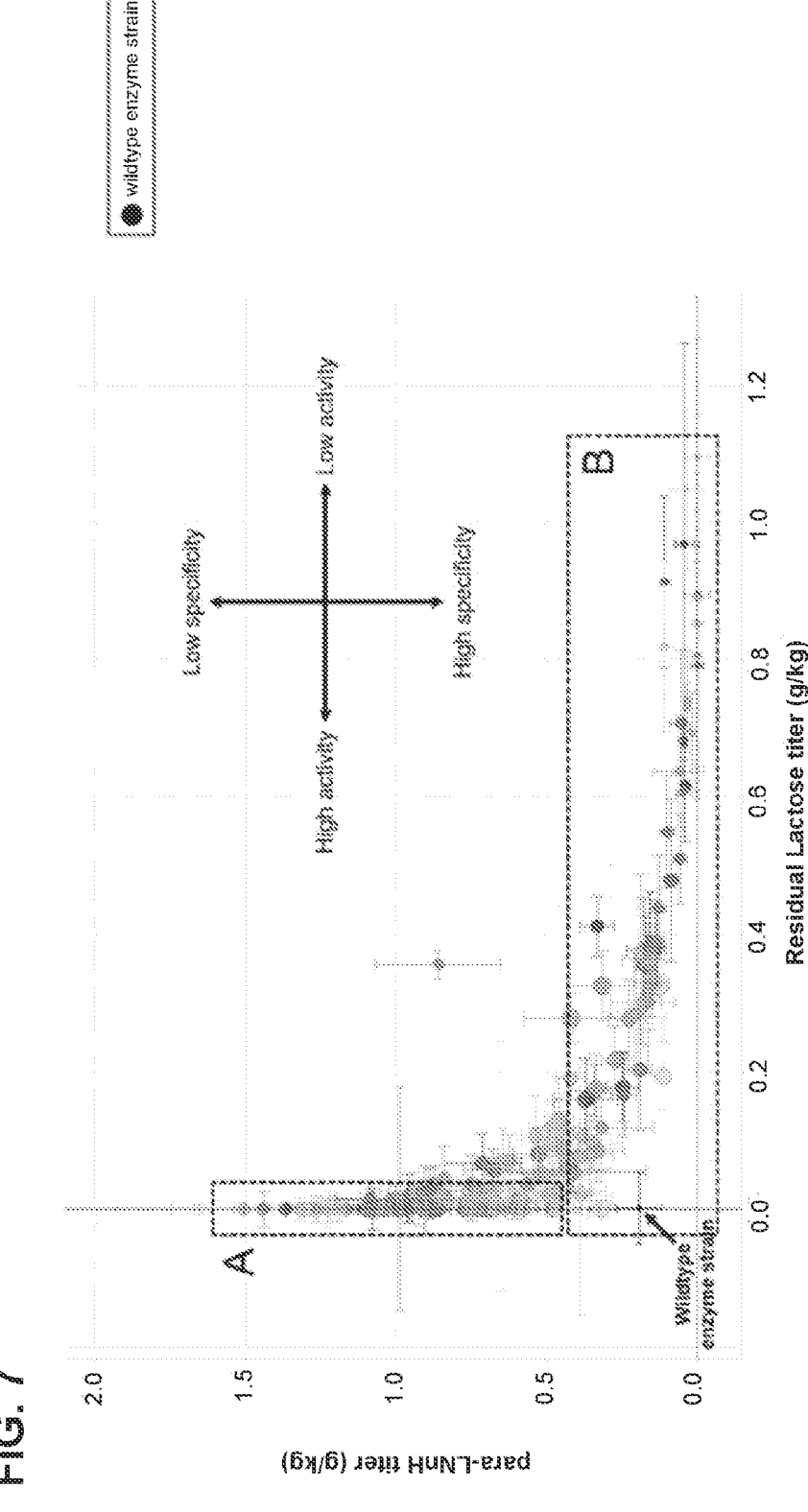
FIG. 7 is a graph showing the top 184 LgtA variants tested in the Tier 2 assay described in Example 1, below. Boxes A and B outline potential false negative and false positive variants from this Tier 2 assay, respectively.

The specific configuration of Tier 2 data visualization in FIG. 7 also highlights potential false negative and false positive variants. Variants in box A are potential false negatives; these variants completely deplete lactose, allowing LNnT to bind to LgtA more easily, thus producing high para-LNnH titers regardless of improved lactose specificity over wild type (see FIG. 5B). Conversely, variants in box B are potential false positives; these variants have residual lactose which competes with LNnT for the LgtA active site, leading to lower para-LNnH titer regardless of specificity improvement (see FIG. 5A). To screen for true false negatives and eliminate true false positives, a total of 95 variants—47 from box A, 48 from box B—were promoted for sequencing to identify LgtA mutant sequences. The variants in each box were selected by highest LNnT-to-para-LNnH titers ratio, to select variants with not only low para-LNnH accumulation but also high LNnT accumulation. Following sequencing, variants with redundant mutations were eliminated.

Figure 15:
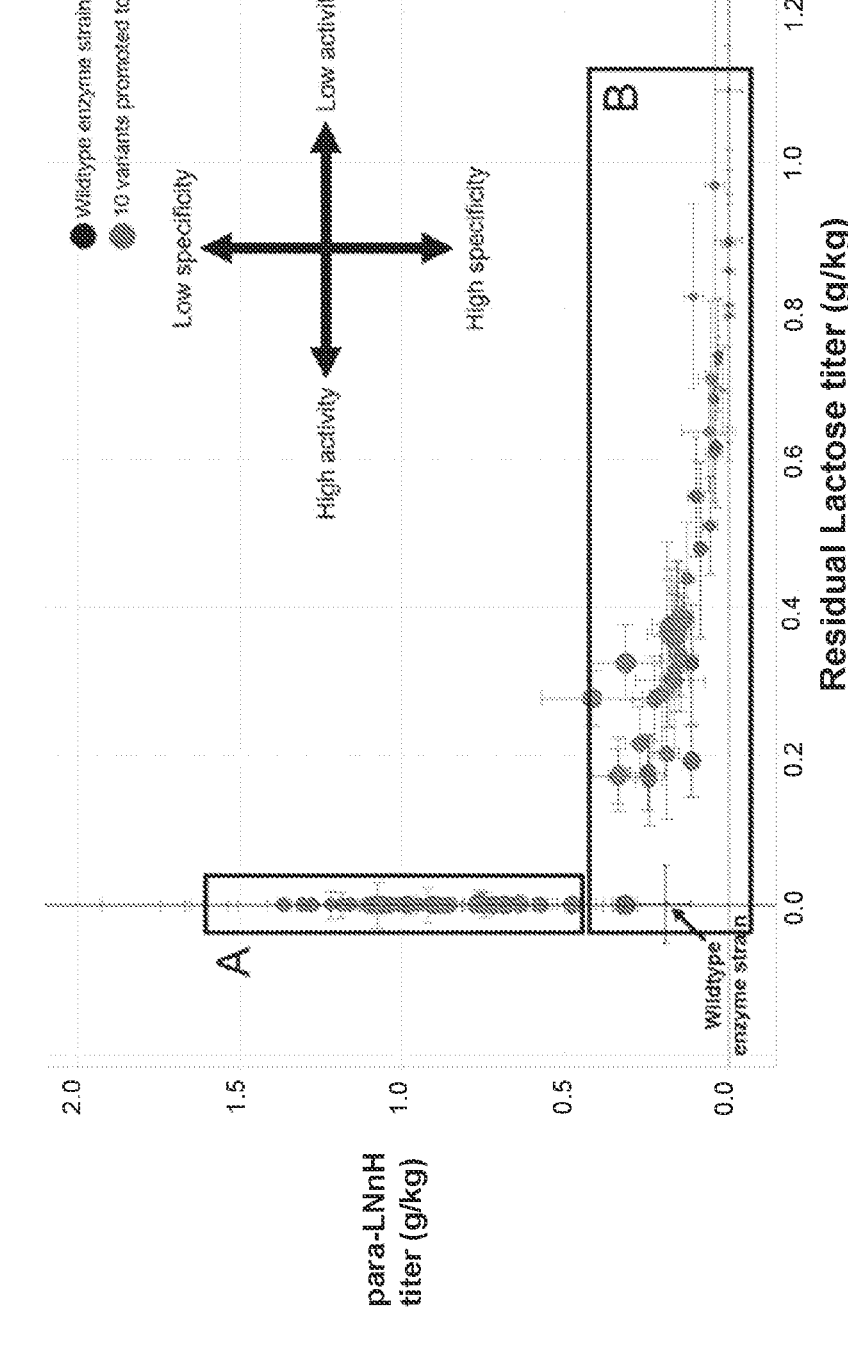
FIG. 15 is a graph showing the para-lacto-n-neohexaose (para-LNnH) titer of Tier 2 LgtA variants described in Example 1, below, including the 10 unique variants promoted directly to Tier 4 screening.

A total of 60 unique variants—30 from box A, 30 from box B, again ranked by highest LNnT-to-para-LNnH ratio—were promoted to Tier 3 for further characterization. In parallel, 10 of the 30 unique variants from box B (potential false positives) were promoted directly to Tier 4 (fermentation tanks) based on Tier 2 results. These 10 variants were selected by highest LNnT-to-para-LNnH ratios at varying titers of residual lactose, from total depletion to a ladder of finite levels (FIG. 15). This is because identifying variants with improvements in specificity regardless of activity changes was prioritized. Indeed, 9 out of the 10 variants have residual lactose while the wild type enzyme does not, suggesting a decreased overall activity in these variants.

Figures 8A, 8B:
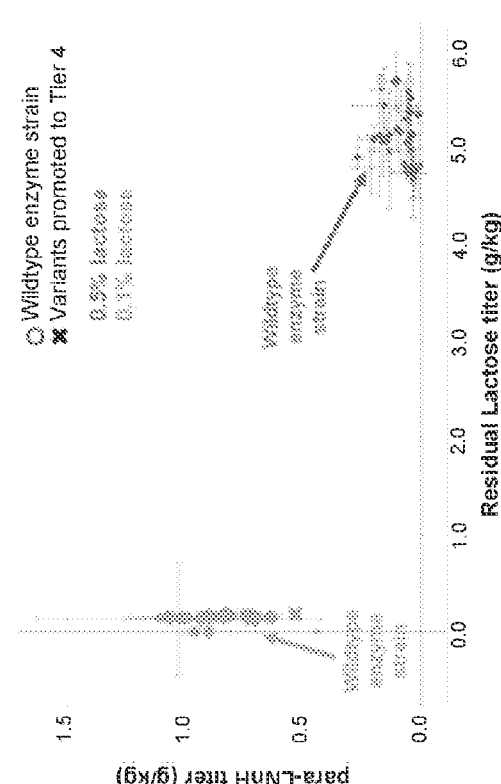
FIGS. 8A and 8B show the top 30 potential false negative variants in the Tier 3 assay described in Example 1, below.

To identify any true false negatives, 30 potential false negative variants (FIG. 7, box A) were promoted to shake-plate Tier 3 assay. Their product profiles were measured by the ion chromatography method in microtiter plates with 0.1% and 0.5% lactose fed. A higher lactose concentration of 0.5% was chosen so that even after microtiter plate incubation, lactose is not completely exhausted. This allows comparison of potential false negative variants and the wild type in a condition where excess lactose skews product profile towards direct lactose derivatives. Indeed, in the presence of residual lactose, all variants as well as the wild type accumulate less para-LNnH (FIG. 8A). This result is likely due to substrate competition between lactose and LNnT, leading to limited conversion of LNnT to downstream products including para-LNnH (see FIG. 5).

Variants with comparable residual lactose to the wild type—suggesting no decrease in activity—while accumulating significantly less para-LNnH than wild type (FIG. 8B) were also observed. These variants are likely true false negative variant: in limiting lactose (0.1% lactose) they deplete lactose and convert LNnT to high para-LNnH titers, while in excess lactose (0.5% lactose) they accumulate less para-LNnH than the wild type. Two variants of this nature, selected again by highest LNnT-to-para-LNnH ratio, were promoted to Tier 4 analysis.

30 potential false positive variants (FIG. 7, box B) were promoted to the Tier 3 shakeplate assay in parallel. Their product profiles were measured by the ion chromatography (IC) method in microtiter plates with 0.05% and 0.1% lactose. A lower lactose concentration of 0.05% was chosen to allow these activity-compromised variants to completely deplete lactose. The amount of resulting para-LNnH created when lactose is not available to compete with LNnT. This set of 30 variants includes the top 10 variants that were promoted directly to Tier 4, based on Tier 2 results. Thus, this assay aimed to serve two purposes: one, to identify and eliminate any true false positives; two, to compare the top 10 Tier 2 variants with the remaining 20 to promote any additional variants to Tier 4.

Figures 16A, 16B:
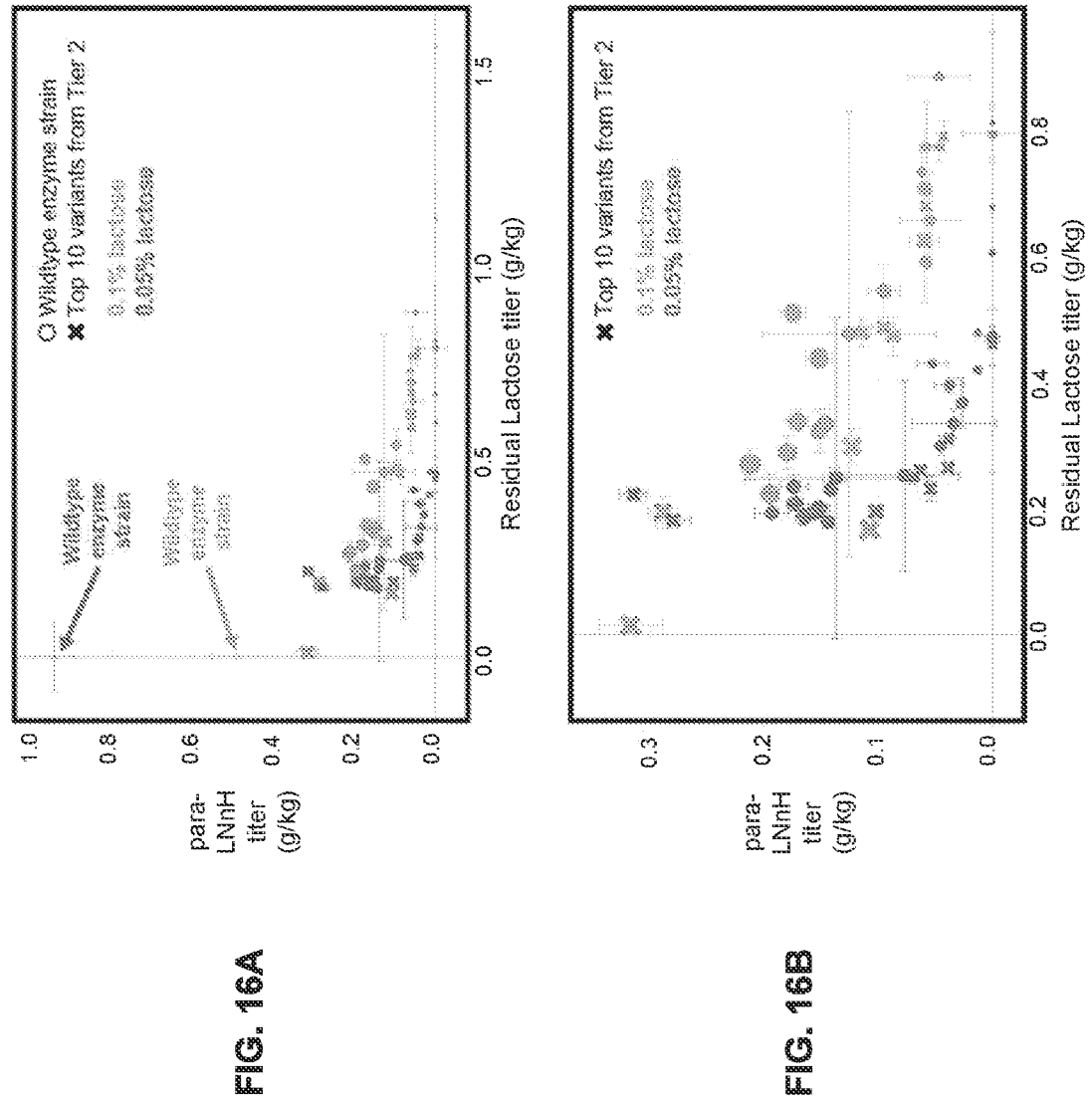
FIGS. 16A and 16B show the para-LNnH titer for the top 30 potential false positive variants from the Tier 2 assay (FIG. 16A) with zoom-in shown in FIG. 16B.

The potential false positive variants did not completely deplete lactose even at the lower lactose level of 0.05%, making identification of true false positives difficult (FIGS. 16A and 16B). The wild type completely depletes lactose in both 0.05% and 0.1% lactose, while accumulating more para-LNnH in the former. Indeed, the lower lactose concentration reaches exhaustion faster, allowing more time during incubation to generate para-LNnH (see FIG. 5). Of the remaining 20 variants, none showed superior product profile over the 10 initially promoted variants; thus, no additional variants were promoted from this set.

Figure 9:
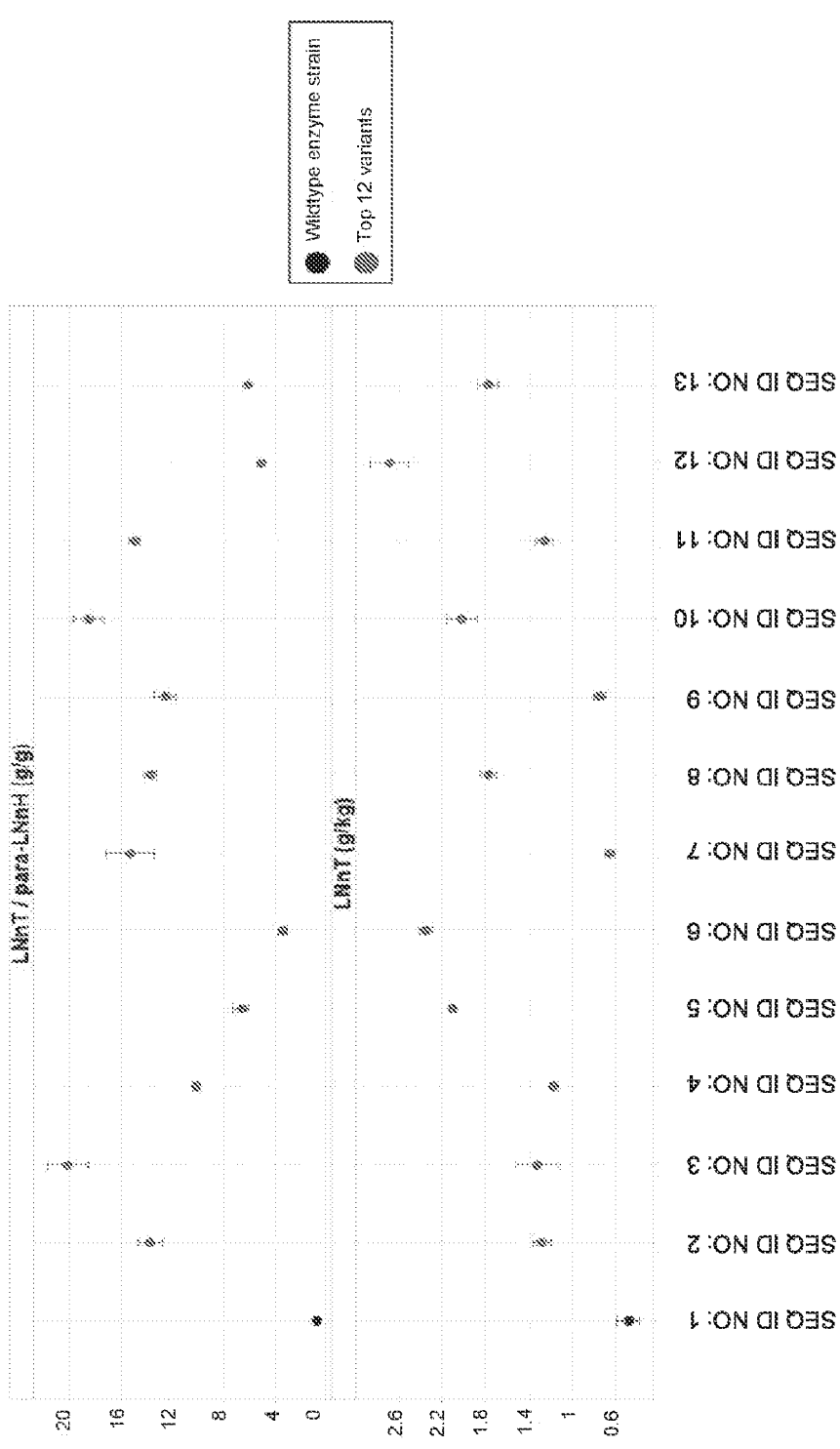
FIG. 9 shows the top 12 variants (SEQ ID NO: 2-13) promoted to Tier 4 assay described in Example 1, below. The top 12 variants effectuate a superior product profile relative to the wild-type LgtA.
Figures 10A, 10B, 10C, 10D:
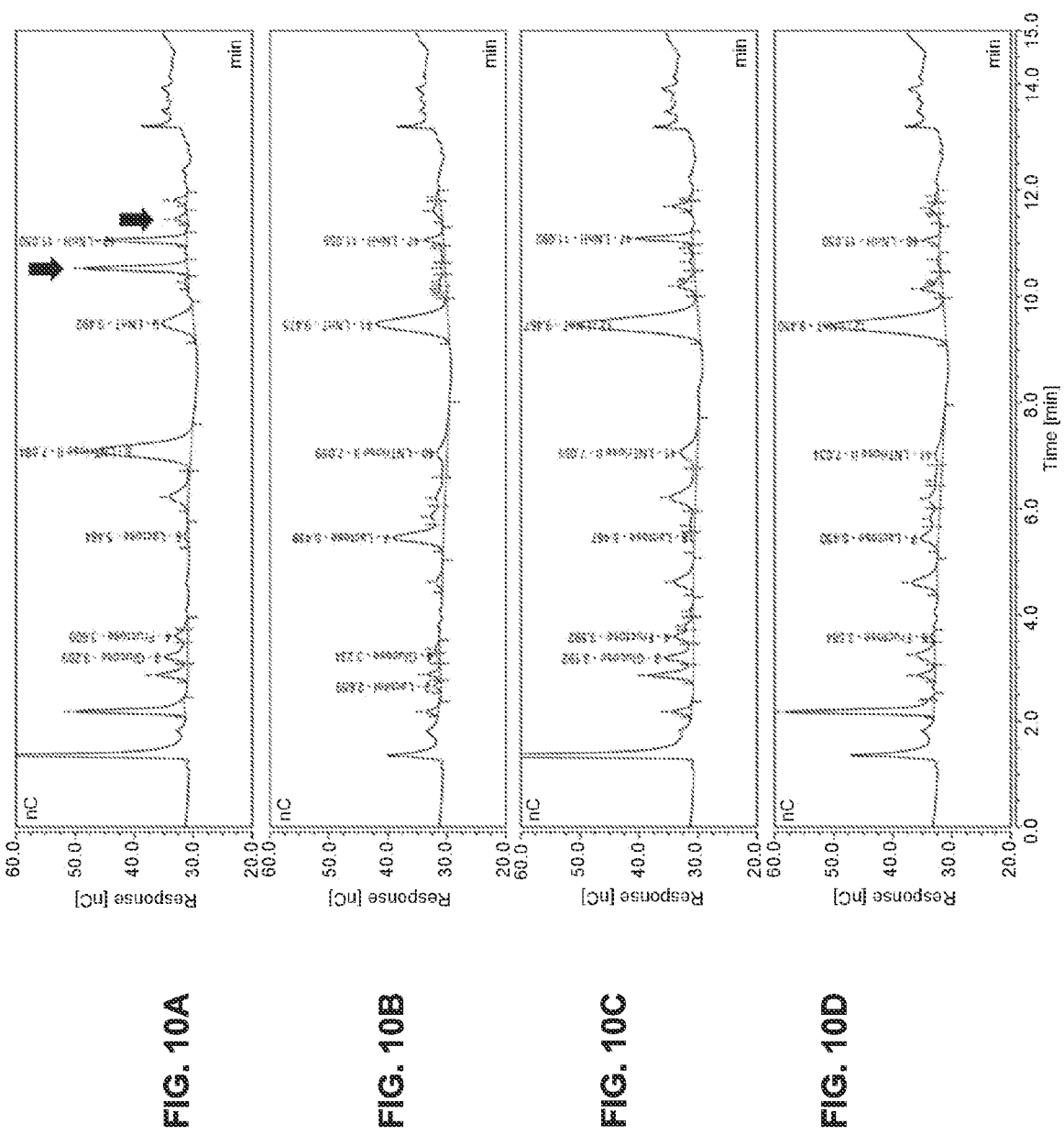
FIGS. 10A-10D show the ion chromatogram response traces for wild-type LgtA (SEQ ID NO: 1) (FIG. 10A) and the variants E294N (FIG. 10B), G179R (FIG. 10C), and G179R, P89T (FIG. 10D) fermented in microtiter plates with 0.1% lactose.

Through tiered plate screening, a list of the top 12 variants was compiled for Tier 4 testing (SEQ ID NO: 2-13): 10 variants initially selected based on Tier 2, and 2 additional variants identified from screening for true false negatives in Tier 3. FIG. 9 summarizes LNnT-to-para-LNnH ratio, absolute LNnT titer, and the genotype of the 12 variants and the wild type in microtiter plates with 0.1% lactose. The wild type reaches 0.48 g/kg LNnT titer, which translates to a ratio of 0.78 g LNnT/g para-LNnH. All variants achieve 1.4 to 5.6-fold higher LNnT titers, while accumulating comparable or far less para-LNnH than the wild type as captured by 4.3 to 26-fold increase in LNnT-to-para-LNnH ratios. Ion chromatograms comparing wild type LgtA with the three of the top 12 variants (FIGS. 10A-10D) show that increase in LNnT titer is accompanied by the reduction of at least two unknown peaks. Such dramatic shifts in product profile support that these variants indeed have altered substrate specificity from mutagenesis; they have improved specificity for lactose relative to LNnT, resulting in a purer LNnT product profile.

In this work, 1425 variants were screened. The top 48 variants were selected based on LNnT/para-LNnH product ratio (top specificity hits) and an additional top 48 LNnT/para-LNnH hits also based on residual lactose titer (activity) lower than wild type. The 96 variants include mutations to 35 unique residues. Among the top specificity hits, one variant, G179R, retains similar residual lactose titer while improving LNnT/LNnH ratio by 8 fold, indicating that most mutations have reduced the catalytic activity of LgtA while increasing specificity towards lactose. Among the selected low residual lactose variants, most of the hits have moderately improved specificity from 1.6 fold to 3.7 fold compared to wild type LgtA, except G179R and S240A mutants, which effectuate more than a 5 fold higher LNnT/LNnH ratio. Due to the complexity of lactose acting as a competitive inhibitor for LNnT production, focus was placed on the top 48 specificity hits that engender a>7 fold improvement in LNnT/LNnH over wild type. In order to decipher the impact of beneficial mutants on LgtA specificity, in silico investigations were undertaken in which the product, LNnT, which is also the undesired potential substrate, was docked into the modeled LgtA structure using the YASARA docking tool (FIGS. 11A and 11B).

Figures 11A, 11B:
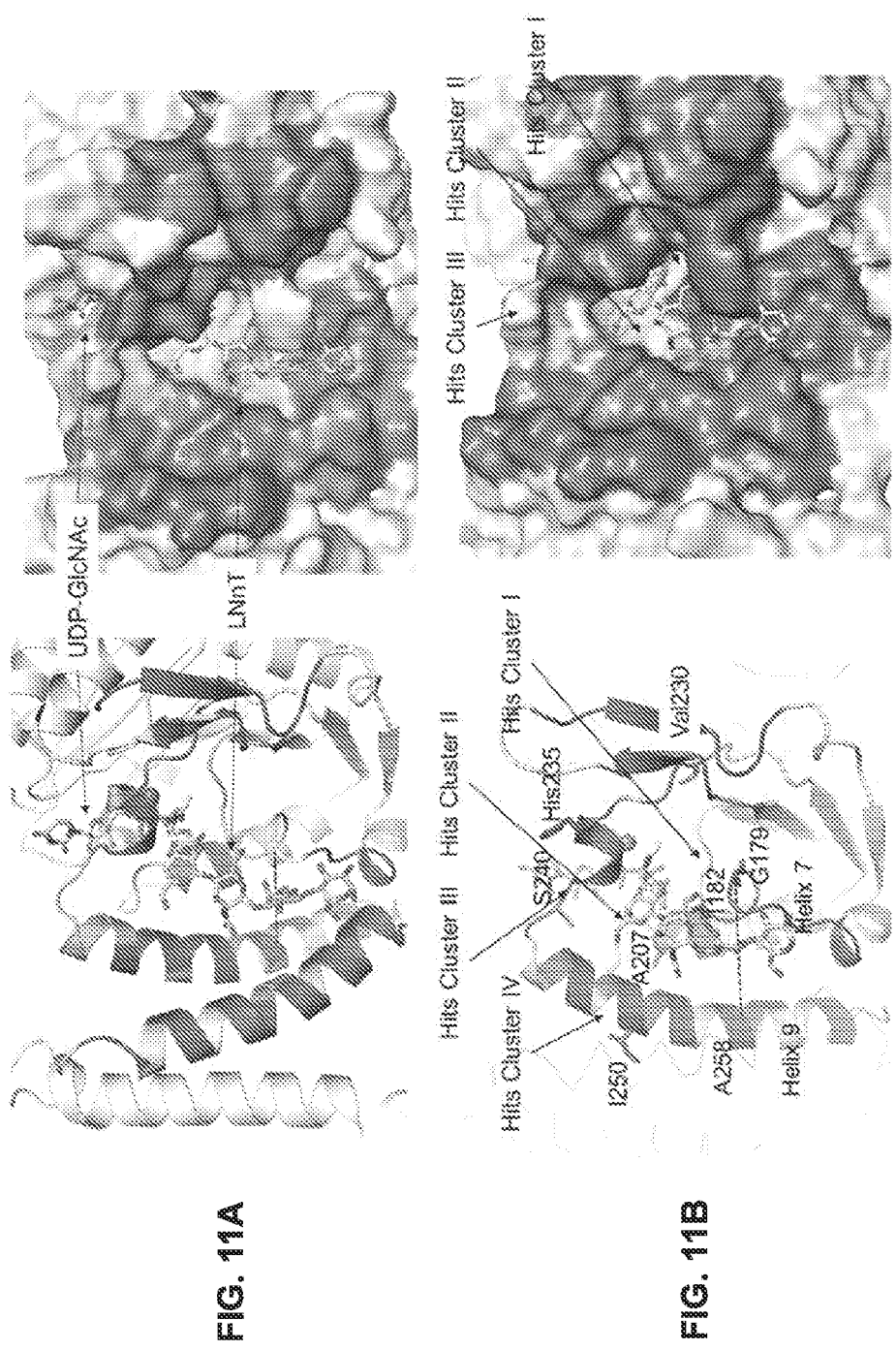
FIGS. 11A and 11B show a cartoon view (left) and surface view (right) of the LgtA mutation hits in the active site (FIG. 11A) and the top 48 specificity hits in the LgtA active site (FIG. 11B). The blue colored regions are the enzyme engineering library residues (excluding hits); the green colored regions are all mutations of interest; the yellow colored regions are the residues imparting substrate specificity; and the pink residues are specificity hits that have mutations with larger amino acid sidechains than wild type. The dashed line between G179 and A258 marks the boundary location of the beneficial mutations discovered, which corresponds to the location of the β1-3 glycosidic bond of LNnT. The specificity hits G179, H183, N185, T186, and M187 cluster on the N-terminal side of the sugar acceptor binding pocket, referred to in Example 1 as "cluster I." W206, A207, Q211, and W213 cluster on the back side of the sugar acceptor binding pocket, referred to in Example 1 as "cluster II." L229, V230, R233, H235, S240, and K242 cluster on the loop over the active site, referred to in Example 1 as "cluster III." Y243, Q247, I250, I254, Q255, and A258 cluster on the C-terminal side of the sugar acceptor binding pocket, referred to in Example 1 as "cluster IV."

All 35 residues that contained the beneficial mutations are plotted on the modeled LgtA structure (FIG. 11A). Interestingly, all of the 35 residues are located proximally to the GlcNAc and galactose units of the LNnT, except for the frameshift-induced truncations at E294 or P315. Even though the library selection was carefully done to cover the entire substrate binding channel and extended surface area, no hits were observed distally to the β1-3 glycosidic bond of LNnT, suggesting the region within a two-sugar radius from the reaction center of the sugar-acceptor binding site is essential for either catalytic activity or substrate specificity.

Figure 12:
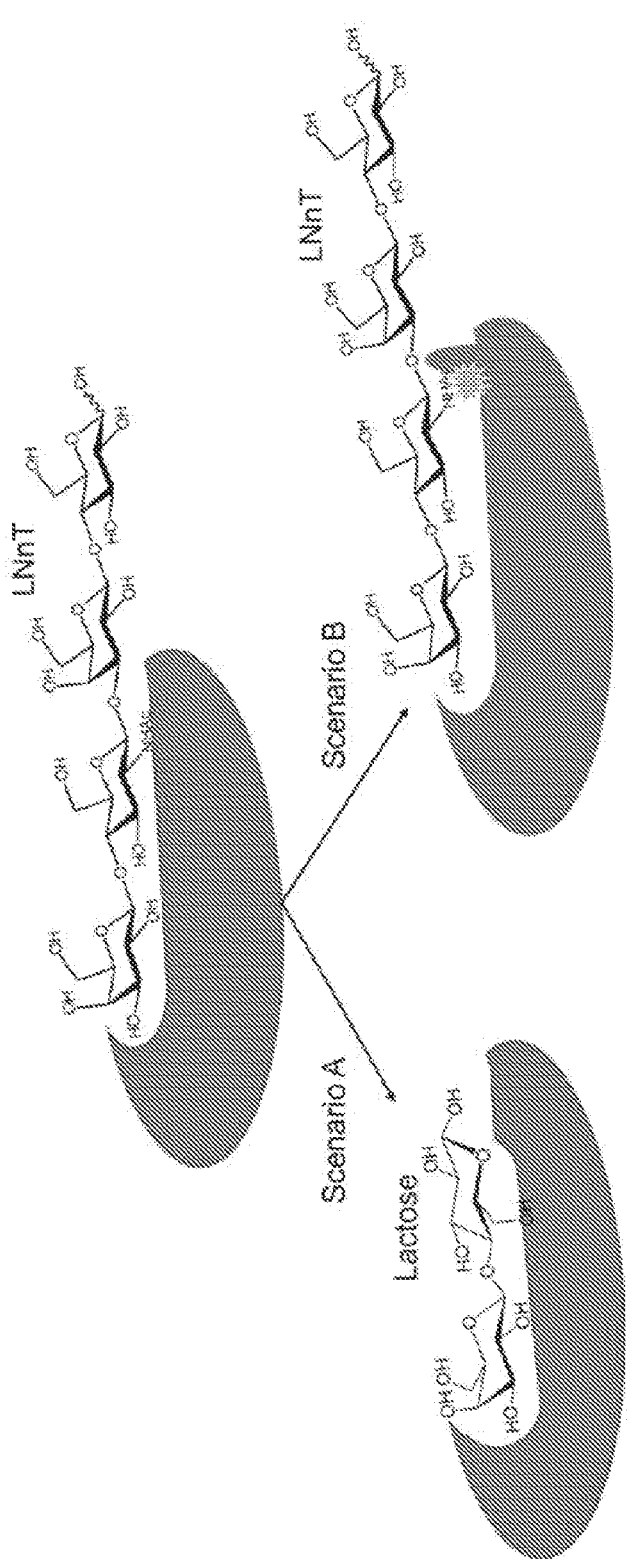
FIG. 12 is a schematic illustration of the mechanism by which the beneficial mutations described herein favor lactose binding. Scenario A represents enzyme variants that have smaller side chains. Scenario B represents enzyme variant that contain larger side chains or side chains of modified electrostatic charge. Amino acid substitutions G179R, N180D, Q255D, A258D, and A258R are located near the acetyl group of LNnT and are represented in scenario B.

Among the Tier 2 confirmed hits, variants from 25 unique residues significantly improved LNnT/LNnH ratio. The hits localize in 4 geological clusters (FIG. 11B). Hits cluster I is located on the N-terminal side of the sugar acceptor binding site, and most of the residues of interest are surface residues that form the right side wall of the binding channel. Cluster II residues are located on helix 7 behind the substrate binding site which forms the back wall of the binding channel. Hits cluster III are on a flexible loop over the reaction center and are likely involved in sugar transfer. The cluster IV residues are located on the helix that includes the left side of the substrate binding site. Comparing amino acid side-chain properties before and after mutation, it was observed that most of the variants (41 unique variants) that improved LNnT/LNnH ratio had mutations generating smaller side chains except G179, I182, A207, V230, R233, S240, I250 and A258 (FIG. 11B and Table 4). Residues V230, R233, S240 are near the reaction center, which likely impacts GlcNAc binding or catalytic activity; these mutations appear to generate more enzyme specificity. The mutations at these residues lead to residual lactose over 2 mmol/kg, suggesting a significant impact on catalytic activity. Interestingly, residues G179, I182 and A258 are located in close proximity to the β1-3 glycoside bond of LNnT. Both the G179 and A258 beneficial mutations confer an electrostatic change to the amino acid side chain as well. These mutations alter the geometry and electrostatic nature of the substrate binding channel in favor of lactose binding over longer polymer binding (FIG. 12). The sugar acceptor binding site of LgtA is a shallow channel that is includes solvent-exposed residues. The geometry of this binding site makes it flexible to accommodate substrates of differing lengths. Most of the beneficial mutations that have smaller side chains, likely open up the substrate binding pocket within the lactose binding region (two sugar radius lengths from the reaction center) to be more selective for lactose (FIG. 12 Scenario A). G179 and A258 mutations, in contrast, result in larger amino acid side chains that incur more steric interference in binding the longer polymers (FIG. 12 Scenario B). Besides oligosaccharide length, the only other difference between lactose and the undesired longer chain length substrate LNnT is the acetyl group of the added GlcNAc molecule. The electrostatic interference imparted by the G179 and A258 residues facilitate selection against the acetyl group on the undesired substrates.

TABLE 4

Beneficial mutations involved in specificity improvement of LgtA

| Cluster | Residues | Mutants | Amino acid side chain size change | Property of the mutants |
|---|---|---|---|---|
| Cluster I | G179 | G179R, P89T | big | Positive |
| Cluster I | G179 | G179R | big | Positive |
| Cluster I | N180 | N180D | moderate | Negative |
| Cluster I | N180 | N180A | small | Hydrophobic |
| Cluster I | I182 | I182Y | big | Hydrophobic |
| Cluster I | H183 | H183P | small | Special case |
| Cluster I | H183 | H183S | small | Polar Uncharged |
| Cluster I | N185 | N185G | small | Special case |
| Cluster I | T186 | T186D | moderate | Negative |
| Cluster I | T186 | T186G | small | Special case |
| Cluster I | M187 | M187P | small | Special case |
| Cluster II | W206 | W206N | small | Polar Uncharged |
| Cluster II | A207 | A207V | moderate | Hydrophobic |
| Cluster II | Q211 | Q211V | small | Hydrophobic |
| Cluster II | Q211 | Q211I | small | Hydrophobic |
| Cluster II | Q211 | Q211C | small | Special case |
| Cluster II | Q211 | Q211L | small | Hydrophobic |
| Cluster II | W213 | W213S | small | Polar Uncharged |
| Cluster II | W213 | W213N | small | Polar Uncharged |

TABLE 4-continued

Beneficial mutations involved in specificity improvement of LgtA

| Cluster | Residues | Mutants | Amino acid side chain size change | Property of the mutants |
|---|---|---|---|---|
| Cluster III | L229 | L229P | small | Special case |
| Cluster III | L229 | L229A | small | Hydrophobic |
| Cluster III | V230 | V230D | big | Negative |
| Cluster III | R233 | R233I | small | Hydrophobic |
| Cluster III | H235 | H235R | big | Positive |
| Cluster III | S240 | S240N | big | Polar Uncharged |
| Cluster III | S240 | S240Y | big | Hydrophobic |
| Cluster III | K242 | K242D | small | Negative |
| Cluster IV | Y243 | Y243A | small | Hydrophobic |
| Cluster IV | Y243 | Y243S | small | Polar Uncharged |
| Cluster IV | Y243 | Y243S | small | Polar Uncharged |
| Cluster IV | Y243 | Y243L | small | Hydrophobic |
| Cluster IV | Y243 | Y243R | small | Positive |
| Cluster IV | Q247 | Q247C, L288S | small | Special case |
| Cluster IV | I250 | I250F | big | Hydrophobic |
| Cluster IV | I254 | I254A | small | Hydrophobic |
| Cluster IV | Q255 | Q255D | small | Negative |
| Cluster IV | A258 | A258D | big | Negative |
| Cluster IV | A258 | A258R | big | Positive |
| Helix 11 | E294 | c.ins890T | Truncation | |
| Helix 11 | P315 | c.del945A | Truncation | |

Example 2. Development of Variant β-1,3-N-acetylglucosaminyltransferases Having a G179R Amino Acid Substitution This example describes a series of experiments conducted to evaluate the effects of various amino acid substitutions and deletions on the substrate specificity of β-1,3-N-acetylglucosaminyltransferase (LgtA) that all include the G179R amino acid substitution. The sections that follow describe the types of amino acid modifications that were assessed and how variant LgtA polypeptides containing the G179R substitution and at least one additional amino acid substitution can be used to improve the production and purity of a desired human milk oligosaccharide (HMO).

Initially, a first screening was performed using 4,627 mutant variants targeting 95 amino acid residues of a Neisseria meningitidis LgtA enzyme already having the G179R substitution (SEQ ID NO: 5) (Uniprot ID=Q8KI61) (Nm. LgtA (G179R)). Of the 95 amino acids targeted, 63 residues had not previously been tested in an initial screening. The variants were generated by PCR amplification using degenerate codon (NNK) primers. 96-well plates were inoculated with individual colonies from library transformation of Nm. LgtA (G179R) variants into S. cerevisiae, followed by a two-day incubation in pre-culture media, then dilution, and a three-day incubation in production media containing sucrose and limiting lactose (0.1% w/w) as a substrate for LNnT production.

Figure 17:
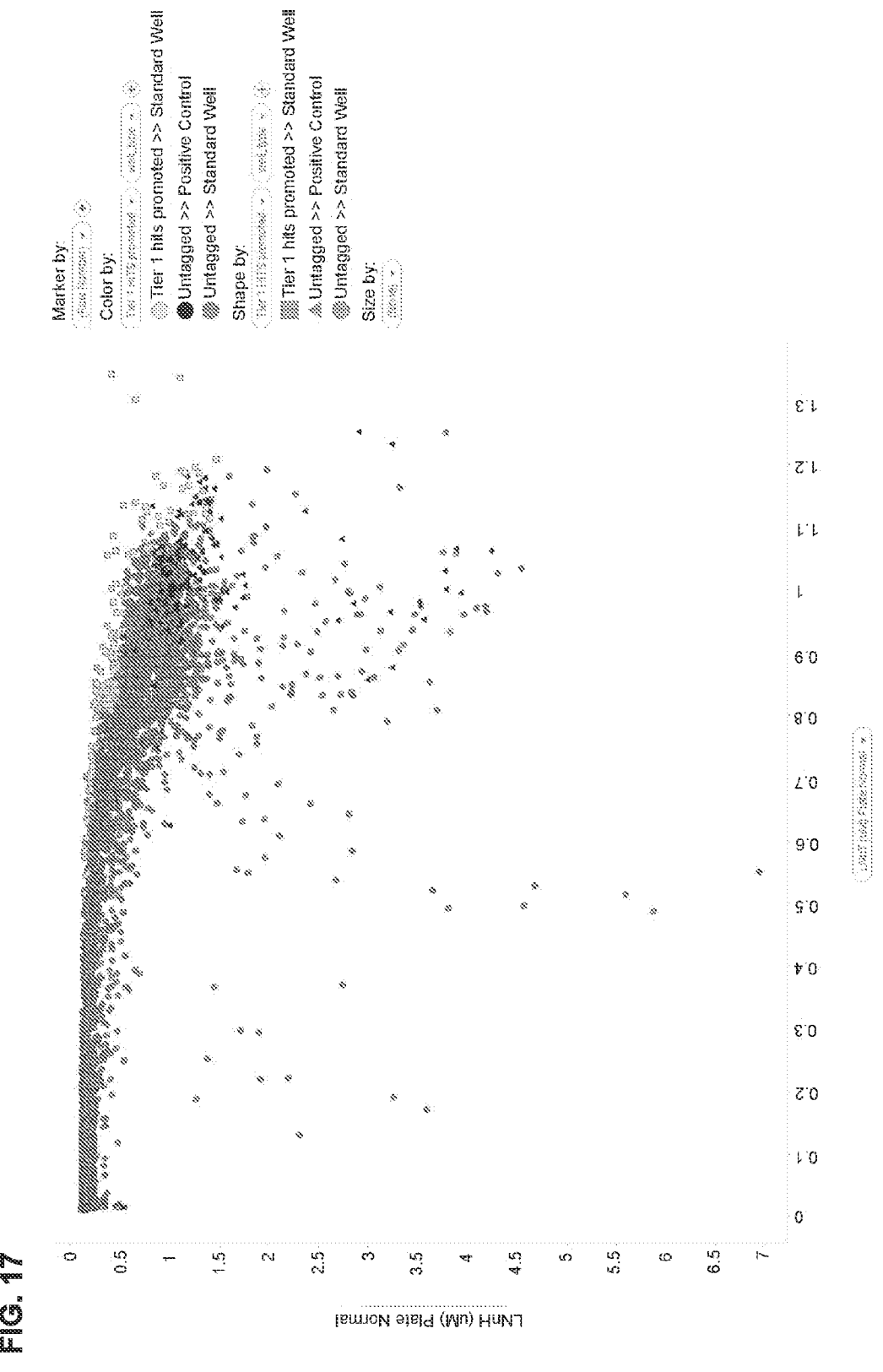
FIG. 17 is a graph showing the LNnH titer of Tier 1 LgtA G179R variants characterized in Example 2, below. Squares indicate strains promoted to Tier 2 screening, as is described in Example 2. Triangles indicate the parent enzyme, and circles indicate those variants that were not promoted to Tier 2 screening.

In limiting lactose media, LNnT production strains expressing Nm. LgtA (G179R) (SEQ ID NO: 5) made significant quantities of the hexameric oligosaccharide impurity lacto-N-neo-hexaose (LNnH). Mass spectrometry was used to detect three key analytes: on-pathway products, including LNTriose II and LNnT, and the impurity, LNnH. Top Nm. LgtA (G179R) enzyme variants were identified as those effectuating the lowest ratio of LNnH impurity to LNnT product at n=1 replication (FIG. 17, upper right quadrant of graph). Titer values for each analyte were normalized to the median value of 4 control replicates of <image name="header">US 12,680,086 B2</image>

73 parent enzyme on each plate (i.e., "plate normal"). 183 top mutants were promoted for additional screening in higher replication.

Figure 18:
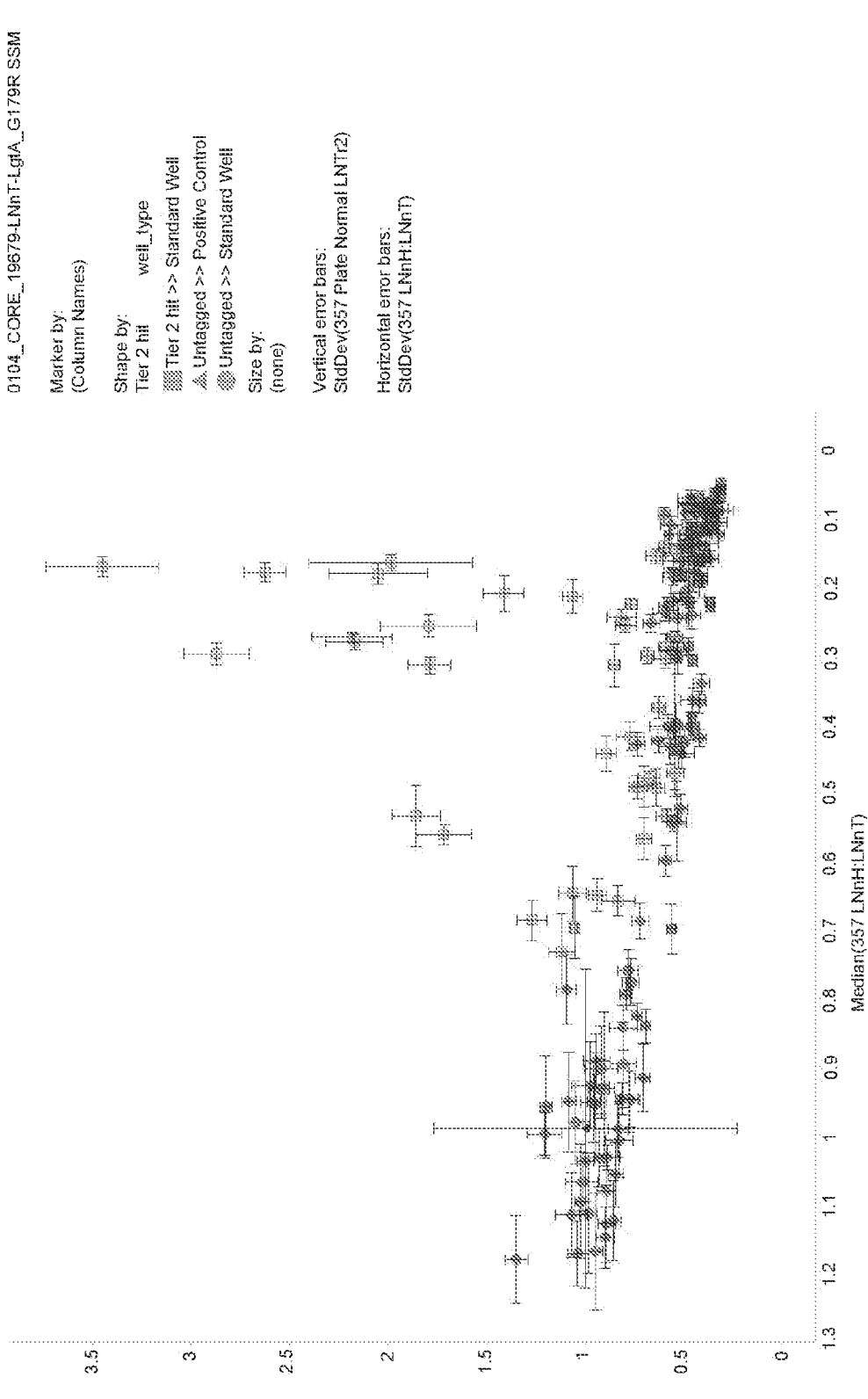
FIG. 18 is a graph showing the LNTriose II titer of Tier 2 LgtA variants characterized in Example 2, below. Squares indicate strains promoted to Tier 3 screening, triangles indicate the parent enzyme, and circles indicate the variants that were not promoted to Tier 3 screening.
Figure 19A:
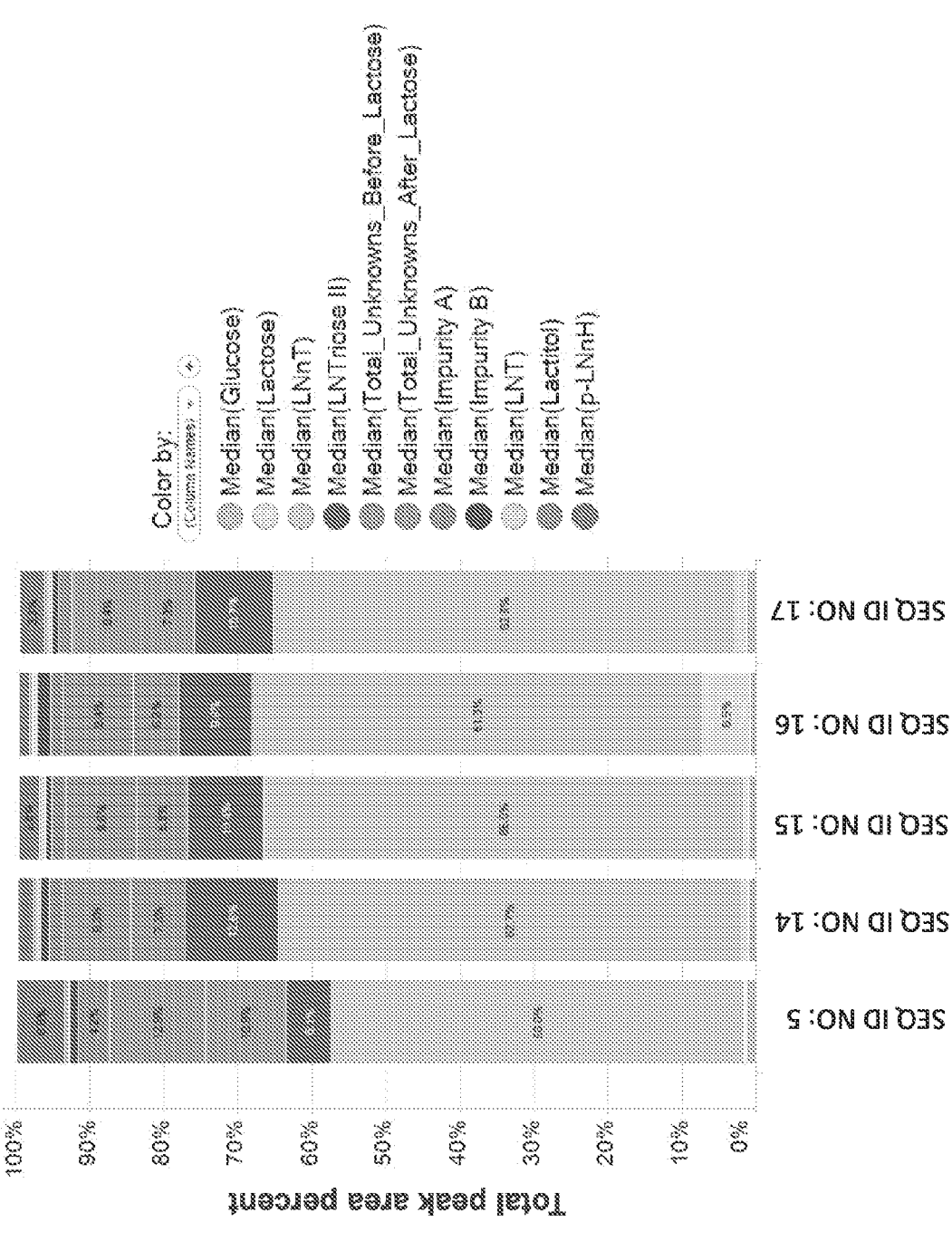
FIG. 19A is a graph showing the relative percentage of glucose, lactose, LNnT, LNTriose II, LNT, lactitol, p-LNnH, and other impurities produced by yeast strains expressing an LgtA enzyme having one of the following amino acid sequences: SEQ ID NO: 5, SEQ ID NO: 14, SEQ ID NO: 15, SEQ ID NO: 16, or SEQ ID NO: 17.
Figure 19B:
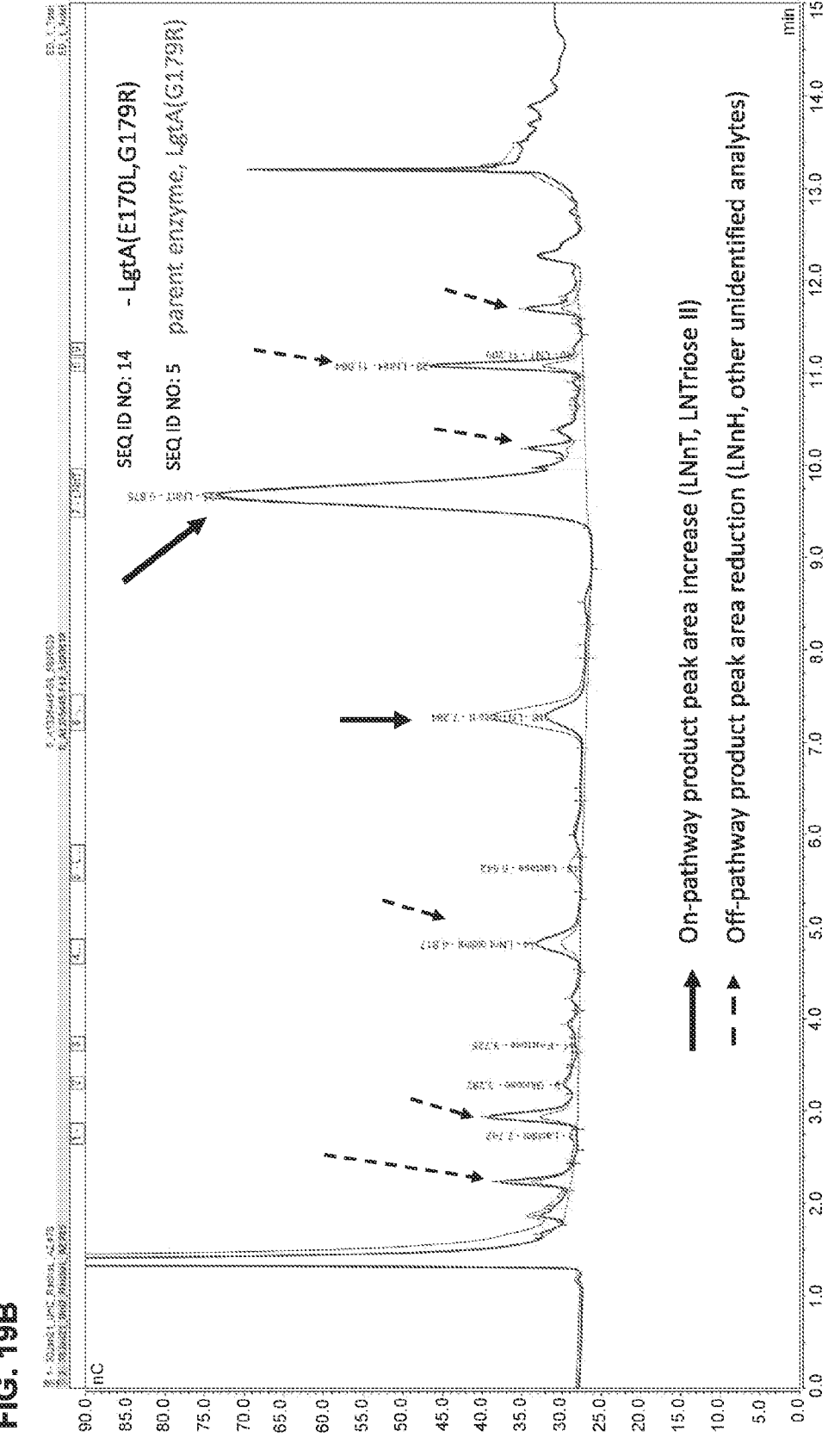
FIGS. 19B-19E are chromatograms showing the amount of LNnT, LNTriose II, LNnH, and other unidentified analytes produced by yeast expressing an LgtA enzyme having the amino acid sequence of SEQ ID NO: 14 (FIG. 19B), SEQ ID NO: 15 (FIG. 19C), SEQ ID NO: 16 (FIG. 19D), or SEQ ID NO: 17 (FIG. 19E) in comparison to the LgtA G179R enzyme. In the chromatograms, black solid arrows indicate on-pathway analytes, LNTriose II and LNnT, which increase in peak area as desired products are produced, and black dashed arrows indicate off-pathway intermediates that decrease in peak area.
Figure 19C:
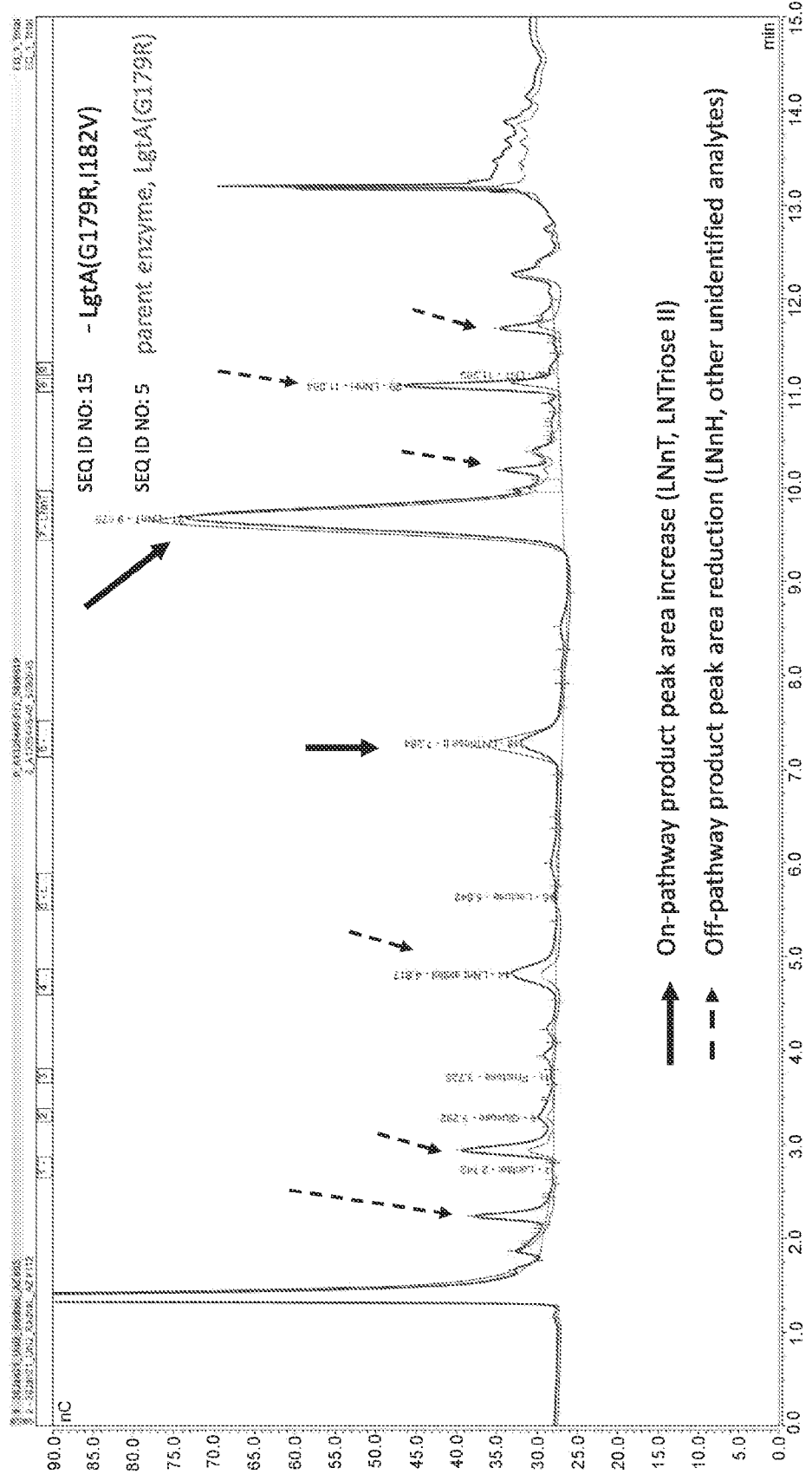
Figure 19D:
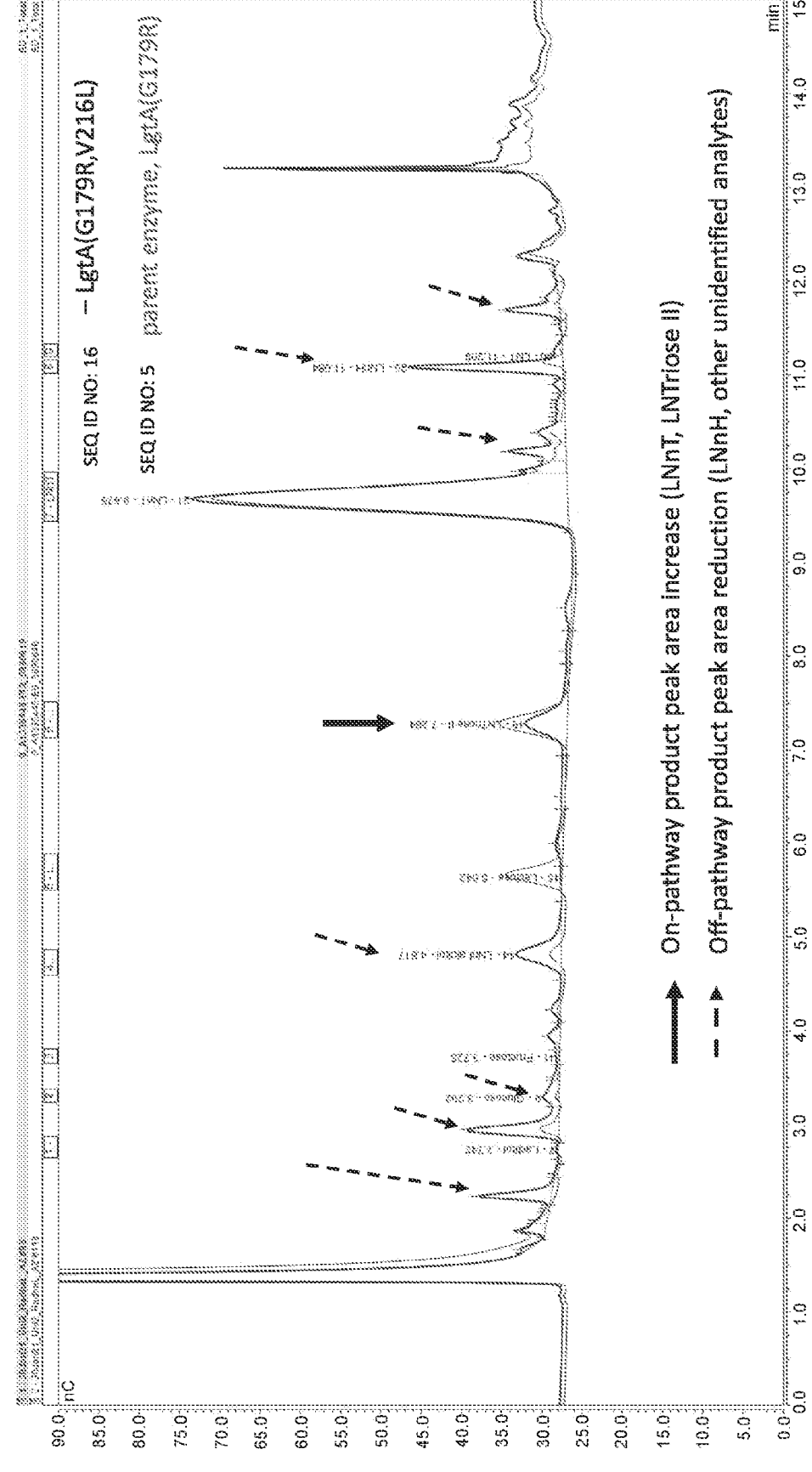
Figure 19E:
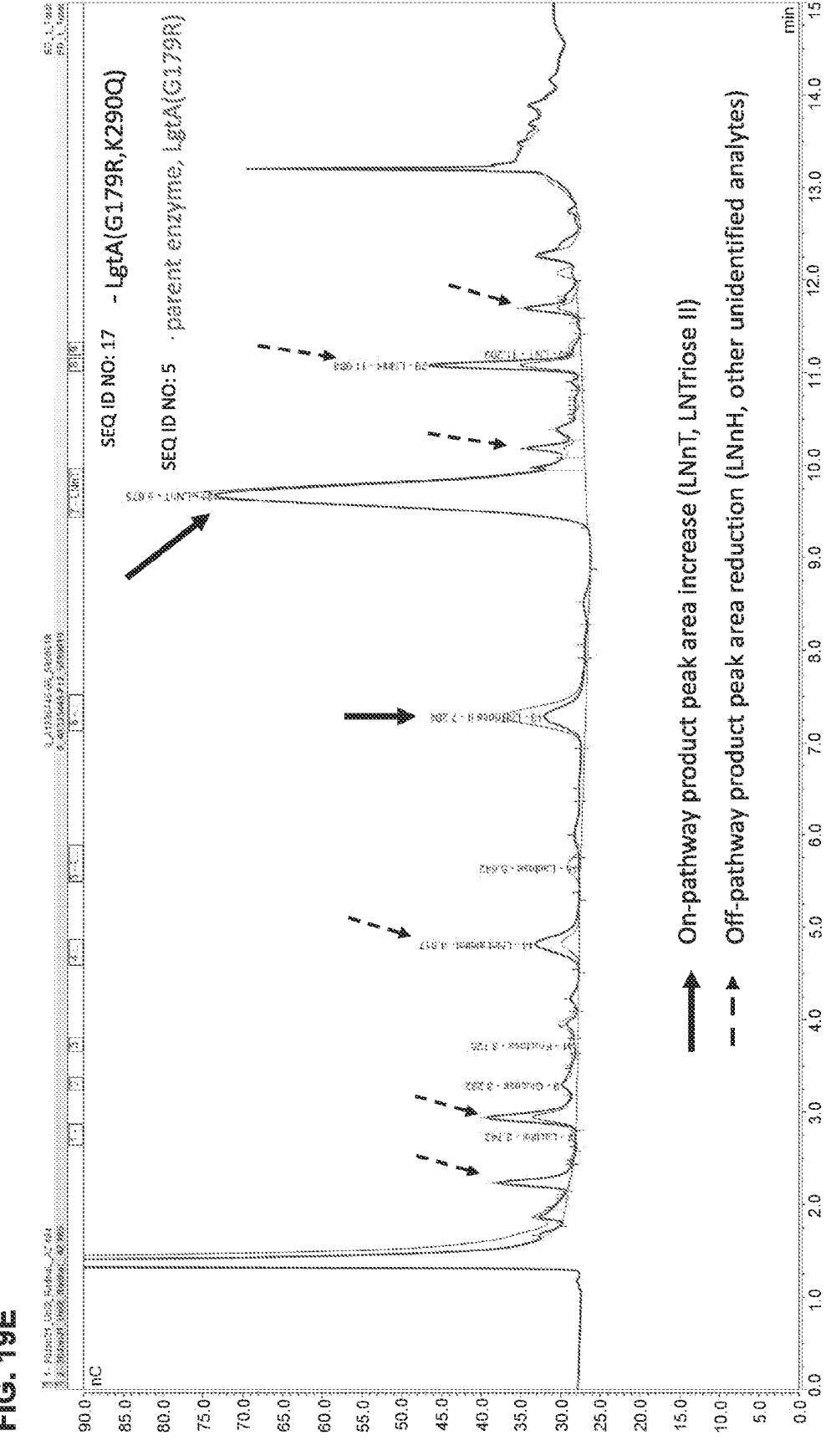

The 183 mutants identified in n=1 Tier 1 enzyme screening were then screened in the same mass spectrometry assay in higher replication (n=4) in a standard shake plate experiment (i.e., two-day incubation in pre-culture media, followed by a three-day incubation in production media containing 0.1% lactose). The top Nm. LgtA (G179R) enzyme variants were identified as those effectuating the lowest ratio of LNnH impurity to LNnT product and highest LNTriose II titer, the direct product of Nm. LgtA (G179R) (FIG. 18, upper right quadrant of graph). Titer values for each analyte were normalized to the median value of 4 control replicates of parent enzyme on each plate (i.e., "plate normal"). 46 top mutants from the Tier 2 screening were promoted for additional screening in higher replication.

The 46 high-performing LgtA (G179R) variants from Tier 2 screening were promoted for Tier 3 screening by ion chromatography to capture additional improvements in product profile beyond reductions in LNnH formation, which is the only impurity detected by the mass spectrometry assay. Each variant was screened in a standard 96-well shake plate experiment (i.e., two-day incubation in pre-culture media, followed by a three-day incubation in production media containing 0.1% lactose), followed by ion chromatography. Nine mutants were determined to be high-performing, of which four (SEQ ID NO: 14-17) showed a reduction in LNnH and an increase in LNnT or LNTriose II, and the remaining 5 (SEQ ID NO: 18-22) showed only a reduction in LNnH (FIGS. 19A-19E). The peak area of each analyte was measured and reported as a percentage of total peak area.

Example 3. Producing LNnT Using a Variant LgtA Polypeptide

Using the compositions and methods of the disclosure, a nucleic acid encoding a variant LgtA polypeptide may be introduced into an *S. cerevisiae* yeast strain, along with nucleic acids encoding the LgtB enzyme from *Pasteurella multocida* and a lactose permease. The yeast strain may be one that already overexpresses four native yeast genes (GFA1, GNA1, PCM1, and QRI1) involved in the biosynthesis of UDP-GlcNAc, the co-substrate of LgtA.

The yeast strain may then be subjected to fermentation, for example, in a fed-batch process. Prior to inoculation, the culture medium may be brought to (and maintained at) a temperature in the range of from about 28° C. to about 32° C. (e.g., a temperature of about 28° C., 29° C., 30° C., 31° C., or 32° C.). Additionally, the pH may be maintained at from about 4.0 to about 6.5 (e.g., a pH of about 4.0, 4.5, 5.0, 5.5, 6.0, or 6.5).

The fermentation may be carried out for 5 days. During the initial phase (0-20 h, 28° C.), the strains may be fed only sucrose and maltose (~44 g/L total sugars fed) with constant airflow. During the growth phase, six pulse doses of 10 g/L sucrose+0.6-0.8 g/L lactose may be fed to the yeast strain in roughly 30-minute intervals. Additionally, a temperature pulse from 28 to 33.5° C. may be started at 24 h (0.67° C./hour). During the production phase, strains may be fed sucrose and lactose at a ratio of 1:16 or 1:12.5 to maintain a dissolved oxygen ratio of 30%. Once the temperature reaches 33.5° C., the temperature may be held for 12 hours, after which the temperature may be dropped to 30° C. for the remainder of the fermentation. The whole cell broth and supernatant may then be harvested from the bioreactors at 120 h.

After the culturing is complete, LNnT product may be recovered by contacting the separated yeast cells with a heated wash liquid. The heated wash liquid may be, for example, a heated aqueous wash liquid that consists of water or another liquid with optionally dissolved solid components. The heated aqueous wash liquid used to recover the product may have a temperature of between 30° C. and 66° C.

The ratio of the yield of LNnT produced to the quantity of sucrose in the culture medium may range, for example, from between 0.01 g/g and 0.4 g/g. Furthermore, the mass of LNnH produced by the yeast cells per gram of LNnT produced by the yeast cells may be between 0.1 g and 1 g.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

SEQUENCE APPENDIX

SEQ ID NO: 1 Wildtype *Neisseria meningitidis* LgtA ß-1,3-N-acetylglucosaminyltransferase
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR*

SEQ ID NO: 2 Nme.LgtA_A258D
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYQFW
YDVSKLGRLAYYPEALVKYRLHANQVSSKYSIRQHEIAQGIQKTDRNDFLQSMGFKTRFDSLEYRQIKAV
AYELLEKHLPEEDFERARRFLYQCFKRTDTPPAGAWLDFAADGRMRRLFTLRQYFGILRRLLKNR*

-continued

---

SEQUENCE APPENDIX

---

SEQ ID NO: 3 Nme.LgtA_c.945delA
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPMPVPG*

SEQ ID NO: 4 Nme.LgtA_ E294N.c890addT
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPNEDFRKS*

SEQ ID NO: 5 Nme.LgtA_G179R
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR*

SEQ ID NO: 6 Nme.LgtA_K242H
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYQFW
YDVSKLGRLAYYPEALVKYRLHANQVSSHYSIRQHEIAQGIQKTARNDFLQSMGFKTRFDSLEYRQIKAV
AYELLEKHLPEEDFERARRFLYQCFKRTDTPPAGAWLDFAADGRMRRLFTLRQYFGILRRLLKNR*

SEQ ID NO: 7 Nme.LgtA_L229P
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYQFW
YDVSKLGRLAYYPEAPVKYRLHANQVSSKYSIRQHEIAQGIQKTARNDFLQSMGFKTRFDSLEYRQIKAV
AYELLEKHLPEEDFERARRFLYQCFKRTDTPPAGAWLDFAADGRMRRLFTLRQYFGILRRLLKNR*

SEQ ID NO: 8 Nme.LgtA_M187P
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTPIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR*

SEQ ID NO: 9 Nme.LgtA_N185G
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNGTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR*

SEQ ID NO: 10 Nme.LgtA_P89T and G179R
MPSEAFRRHRAYRENKLQSLVSVLICAYNVEKYFAQSLAAVVNQTWRNLEILIVDDGSTDGTLAIAKDFQK
RDSRIKILAQAQNSGLITSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR*

SEQ ID NO: 11 Nme.LgtA_Q211V
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYVFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR*

SEQ ID NO: 12 Nme.LgtA_S240V
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYQFW
YDVSKLGRLAYYPEALVKYRLHANQVVSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR*

SEQ ID NO: 13 Nme.LgtA_W213N
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFGNPIHNNTMIMRRSVIDGGLRYNTERDWAEDYQFN
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR*

-continued

---

SEQUENCE APPENDIX

---

SEQ ID NO: 14 Nme.LgtA_G179R_E170L
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHLDIADFFPFRNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR

SEQ ID NO: 15 Nme.LgtA_G179R_I182V
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPVHNNTMIMRRSVIDGGLRYNTERDWAEDYQF
WYDVSKLGRLAYYPEALVKYRLHANQVSSKYSIRQHEIAQGIQKTARNDFLQSMGFKTRFDSLEYRQIKA
VAYELLEKHLPEEDFERARRFLYQCFKRTDTPPAGAWLDFAADGRMRRLFTLRQYFGILRRLLKNR

SEQ ID NO: 16 Nme.LgtA_G179R_V216L
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDLSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR

SEQ ID NO: 17 Nme.LgtA_G179R_K290Q
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEQHLPEEDFERARRFLYQCFKRTDTPPAGAWLDFAADGRMRRLFTLRQYFGILRRLLKNR

SEQ ID NO: 18 Nme.LgtA_G179R_V230A
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDVSKLGRLAYYPEALAKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR

SEQ ID NO: 19 Nme.LgtA_G179R_S244T
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDVSKLGRLAYYPEALVKYRLHANQVSSKYTIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR

SEQ ID NO: 20 Nme.LgtA_G179R_S265H
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDVSKLGRLAYYPEALVKYRLHANQVSSKYSIRQHEIAQGIQKTARNDFLQHIRQHEIAQGIQKTARNDFL
QSMGFKTRFDSLEYRQIKAVAYELLEKHLPEEDFERARRFLYQCFKRTDTPPAGAWLDFAADGRMRRLF
TLRQYFGILRRLLKNR

SEQ ID NO: 21 Nme.LgtA_G179R_S284Y
MPSEAFRRHRAYRENKLQSLVSVLICAYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVY
YELLEKHLPEEDFERARRFLYQCFKRTDTPPAGAWLDFAADGRMRRLFTLRQYFGILRRLLKNR

SEQ ID NO: 22 Nme.LgtA_G179R_A27G
MPSEAFRRHRAYRENKLQSLVSVLICGYNVEKYFAQSLAAVVNQTWRNLEILIVDDGSTDGTLAIAKDFQK
RDSRIKILAQAQNSGLIPSLNIGLDELAKSGMGEYIARTDADDIAAPDWIEKIVGEMEKDRSIIAMGAWLEVL
SEEKDGNRLARHHRHGKIWKKPTRHEDIADFFPFRNPIHNNTMIMRRSVIDGGLRYNTERDWAEDYQFW
YDVSKLGRLAYYPEALVKYRLHANQVSSKYSIRQHEIAQGIQKTARNDFLQSMGFKTRFDSLEYRQIKAVA
YELLEKHLPEEDFERARRFLYQCFKRTDTPPAGAWLDFAADGRMRRLFTLRQYFGILRRLLKNR

SEQ ID NO: 23 LAC12 lactose permease from *K. lactis*
MADHSSSSSSLQKKPINTIEHKDTLGNDRDHKEALNSDNDNTSGLKINGVPIEDAREEVLLPGYLSKQYYK
LYGLCFITYLCATMQGYDGALMGSIYTEDAYLKYYHLDINSSSGTGLVFSIFNVGQICGAFFVPLMDWKGR
KPAILIGCLGVVIGAIISSLTTTKSALIGGRWFVAFFATIANAAAPTYCAEVAPAHLRGKVAGLYNTLWSVGS
IVAAFSTYGTNKNFPNSSKAFKIPLYLQMMFPGLVCIFGWLIPESPRWLVGVGREEEAREFIIKYHLNGDR
THPLLDMEMAEIIESFHGTDLSNPLEMLDVRSLFRTRSDRYAMLVILMAWFGQFSGNNVCSYYLPTMLR
NVGMKSVSLNVLMNGVYSIVTWISSICGAFFIDKIGRREGFLGSISGAALALTGLSICTARYEKTKKKSASN
GALVFIYLFGGIFSFAFTPMQSMYSTEVSTNLTRSKAQLLNFVVSGVAQFVNQFATPKAMKNIKYWFYVFY
VFFDIFEFIVIYFFFVETKGRSLEELEVVFEAPNPRKASVDQAFLAQVRATLVQRNDVRVANAQNLKEQEP
LKSDADHVEKLSEAESV -continued

---

SEQUENCE APPENDIX

---

SEQ ID NO: 24 LgtB from *Pasteurella multocida*
MSGEHYVISLSSAVERRQHIRNQFSQKNIPFQFFDAISPSPLLDQLVLQFFPRLADSSLTGGEKACFMSHL
SLWHKCVEENLPYIVVFEDDIVLGKDADKFLIGDEWLFSRFDPEEIFIIRLETFLQKVVCESTHIAPYTHRDF
LSLKSAHFGTAGYVISQGAAKFLLDIFKNISNEHIAPIDELIFNQFLVKNSFNVYQLSPAICVQELQLNNESS
ALQSQLELERNKFRNKKSEELKRNRKNFIEKFIYILKKPKRMLDNNKRKREESKIENDKMIIEFK SEQ ID NO: 25 LgtB from *Neisseria gonorrhoeae*
MQNHVISLASAAERRAHIAATFGSRGIPFQFFDALMPSERLERAMAELVPGLSAHPYLSGVEKACFMSHA
VLWEQALDEGVPYIAVFEDDVLLGEGAEQFLAEDTWLQERFDPDSAFVVRLETMFMHVLTSPSGVADYG
GRAFPLLESEHCGTAGYIISRKAMRFFLDRFAVLPPERLHPVDLMMFGNPDDREGMPVCQLNPALCAQE
LHYAKFHDQNSALGSLIEHDRRLNRKQQWRDSPANTFKHRLIRALTKIGREREKRRQRREQLIGKIIVPFQ

---

The invention claimed is:

1. A variant β-1,3-N-acetylglucosaminyltransferase (LgtA) polypeptide comprising a G179R or G179K amino acid substitution relative to the amino acid sequence of SEQ ID NO: 1, wherein the polypeptide has an amino acid sequence that is from 90% to 99.7% identical to the amino acid sequence of SEQ ID NO: 1.

2. The variant polypeptide of claim 1, wherein the polypeptide further comprises one or more amino acid substitutions relative to SEQ ID NO: 1 selected from A27G, P89T, E170L, N180D, N180A, I182V, I182Y, H183P, H183S, N185G, T186G, T186D, M187P, W206N, A207V, Q211V, Q211C, Q211I, Q211L, W213S, W213N, V216L, L229A, L229P, V230A, V230D, R2331, H235R, S240N, S240Y, K242D, Y243S, Y243A, Y243L, Y243R, S244T, Q247C, I250F, I254A, Q255D, A258D, A258R, S265H, S284Y, L288S, K290Q, and/or E294N.

3. The variant polypeptide of claim 1, wherein the polypeptide further comprises a E170L, I182V, V216L, or K290Q amino acid substitution relative to SEQ ID NO: 1.

4. The variant polypeptide of claim 1, wherein the polypeptide has an amino acid sequence that is from 95% to 99.7% identical to the amino acid sequence of SEQ ID NO: 1.

5. The variant polypeptide of claim 1, wherein the polypeptide has an amino acid sequence that is at least 90% identical to the amino acid sequence of any one of SEQ ID NO: 5, 10, or 14-22.

6. The variant polypeptide of claim 5, wherein the polypeptide has an amino acid sequence of any one of SEQ ID NO: 5, 10, or 14-22.

7. The variant polypeptide of claim 1, wherein the polypeptide exhibits increased substrate specificity for lactose over a longer chain oligosaccharide as compared to a polypeptide having the amino acid sequence of SEQ ID NO: 1.

8. A nucleic acid encoding the variant polypeptide of claim 1.

9. A isolated recombinant host cell comprising the variant polypeptide of claim 1.

10. The isolated recombinant host cell of claim 9, wherein the cell is capable of producing a human milk oligosaccharide, wherein the cell comprises one or more heterologous nucleic acids that each, independently, encode one or more additional enzymes of the biosynthetic pathway of the human milk oligosaccharide.

11. The isolated recombinant host cell of claim 10, wherein the one or more additional enzymes comprise one or both of a β-1,4-galactosyltransferase (LgtB) and a UDP-N-acetylglucosamine diphosphorylase.

12. The isolated recombinant host cell of cell of claim 10 wherein the one or more heterologous nucleic acids encode a protein that transports lactose into the cell, wherein the protein that transports lactose into the cell is a lactose permease or a lactose transporter.

13. A method of producing a human milk oligosaccharide, the method comprising culturing a population of host cells of claim 9 in a culture medium under conditions suitable for the host cells to produce the human milk oligosaccharide.

14. A fermentation composition comprising (i) a population of host cells comprising the host cell of claim 9 and (ii) a culture medium comprising a human milk oligosaccharide produced from the host cells.

15. A method of recovering a human milk oligosaccharide from the fermentation composition of claim 14, the method comprising:
   a. separating at least a portion of the population of host cells from the culture medium;
   b. contacting the separated host cells with a heated aqueous wash liquid; and
   C. removing the wash liquid from the separated host cells.

16. A method of genetically modifying a yeast cell to produce a human milk oligosaccharide, the method comprising:
   a. (i) introducing a heterologous nucleic acid encoding the variant polypeptide of claim 1 into the yeast cell and (ii) introducing one or more heterologous nucleic acids that each, independently, encode one or more additional enzymes of the biosynthetic pathway of the human milk oligosaccharide into the yeast cell; or b. introducing a heterologous nucleic acid encoding the variant polypeptide of claim 1 into the yeast cell, wherein the yeast cell comprises one or more heterologous nucleic acids that each, independently, encode one or more additional enzymes of the biosynthetic pathway of the human milk oligosaccharide.

17. The method of claim 16, wherein the one or more additional enzymes comprise one or both of an LgtB and a UDP-N-acetylglucosamine diphosphorylase, optionally wherein the LgtB has an amino acid sequence that is at least 85% identical to the amino acid sequence of SEQ ID NO: 24 or SEQ ID NO: 25.

18. The method of claim 16, wherein the one or more heterologous nucleic acids encode a protein that transports lactose into the cell, wherein the protein that transports lactose into the cell is a lactose permease or a lactose transporter.

19. The method of claim 16, wherein the human milk oligosaccharide is LNnT, and wherein the method results in:

(i) from about a 2-fold increase to about a 6-fold increase in LNnT titer relative to a corresponding method in which a polypeptide having the amino acid sequence of SEQ ID NO: 1 is used in place of the variant polypeptide, or (ii) an increase in the ratio of LNnT produced to para-lacto-N-neopentaose (p-LNnP) or para-lacto-N-neohexaose (p-LNnH) produced, by mass, relative to a corresponding method in which a polypeptide having the amino acid sequence of SEQ ID NO: 1 is used in place of the variant polypeptide.

20. The host cell of claim 11, wherein the LgtB has an amino acid sequence that is at least 85% identical to the amino acid sequence of SEQ ID NO: 24 or SEQ ID NO: 25.

* * * * *

SEQUENCE LISTING

<160> NUMBER OF SEQ ID NOS: 25

<210> SEQ ID NO 1
<211> LENGTH: 348
<212> TYPE: PRT
<213> ORGANISM: Neisseria meningitidis

<400> SEQUENCE: 1

Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
            195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe

```
              260              265              270

Asp Ser Leu Glu Tyr Arg Gln Ile Lys Ala Val Ala Tyr Glu Leu Leu
              275              280              285

Glu Lys His Leu Pro Glu Glu Asp Phe Glu Arg Ala Arg Arg Phe Leu
              290              295              300

Tyr Gln Cys Phe Lys Arg Thr Asp Thr Pro Ala Gly Ala Trp Leu
305              310              315              320

Asp Phe Ala Ala Asp Gly Arg Met Arg Arg Leu Phe Thr Leu Arg Gln
              325              330              335

Tyr Phe Gly Ile Leu Arg Arg Leu Leu Lys Asn Arg
              340              345

<210> SEQ ID NO 2
<211> LENGTH: 348
<212> TYPE: PRT
<213> ORGANISM: Artificial Sequence
<220> FEATURE:
<223> OTHER INFORMATION: Synthetic Construct

<400> SEQUENCE: 2

Met Pro Ser Glu Ala Phe Arg Arg His Arg Ala Tyr Arg Glu Asn Lys
1                5               10               15

Leu Gln Ser Leu Val Ser Val Leu Ile Cys Ala Tyr Asn Val Glu Lys
              20               25               30

Tyr Phe Ala Gln Ser Leu Ala Ala Val Val Asn Gln Thr Trp Arg Asn
              35               40               45

Leu Glu Ile Leu Ile Val Asp Asp Gly Ser Thr Asp Gly Thr Leu Ala
              50               55               60

Ile Ala Lys Asp Phe Gln Lys Arg Asp Ser Arg Ile Lys Ile Leu Ala
65               70               75               80

Gln Ala Gln Asn Ser Gly Leu Ile Pro Ser Leu Asn Ile Gly Leu Asp
              85               90               95

Glu Leu Ala Lys Ser Gly Met Gly Glu Tyr Ile Ala Arg Thr Asp Ala
              100              105              110

Asp Asp Ile Ala Ala Pro Asp Trp Ile Glu Lys Ile Val Gly Glu Met
              115              120              125

Glu Lys Asp Arg Ser Ile Ile Ala Met Gly Ala Trp Leu Glu Val Leu
              130              135              140

Ser Glu Glu Lys Asp Gly Asn Arg Leu Ala Arg His His Arg His Gly
145              150              155              160

Lys Ile Trp Lys Lys Pro Thr Arg His Glu Asp Ile Ala Asp Phe Phe
              165              170              175

Pro Phe Gly Asn Pro Ile His Asn Asn Thr Met Ile Met Arg Arg Ser
              180              185              190

Val Ile Asp Gly Gly Leu Arg Tyr Asn Thr Glu Arg Asp Trp Ala Glu
              195              200              205

Asp Tyr Gln Phe Trp Tyr Asp Val Ser Lys Leu Gly Arg Leu Ala Tyr
              210              215              220

Tyr Pro Glu Ala Leu Val Lys Tyr Arg Leu His Ala Asn Gln Val Ser
225              230              235              240

Ser Lys Tyr Ser Ile Arg Gln His Glu Ile Ala Gln Gly Ile Gln Lys
              245              250              255

Thr Asp Arg Asn Asp Phe Leu Gln Ser Met Gly Phe Lys Thr Arg Phe
              260              265              270

Asp Ser Leu Glu Tyr Arg Gln Ile Lys Ala Val Ala Tyr Glu Leu Leu
```

-continued

```
        275                 280                 285

Glu Lys His Leu Pro Glu Glu Asp Phe Glu Arg Ala Arg Arg Phe Leu
    290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
                340                 345

<210> SEQ ID NO 3
<211> LENGTH: 319
<212> TYPE: PRT
<213> ORGANISM: Artificial Sequence
<220> FEATURE:
<223> OTHER INFORMATION: Synthetic Construct

<400> SEQUENCE: 3

Met Pro Ser Glu Ala Phe Arg Arg His Arg Ala Tyr Arg Glu Asn Lys
1                   5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
                35                  40                  45

Leu Glu Ile Leu Ile Val Asp Asp Gly Ser Thr Asp Gly Thr Leu Ala
                50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
                100                 105                 110

Asp Asp Ile Ala Ala Pro Asp Trp Ile Glu Lys Ile Val Gly Glu Met
                115                 120                 125

Glu Lys Asp Arg Ser Ile Ile Ala Met Gly Ala Trp Leu Glu Val Leu
                130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Asn Thr Met Ile Met Arg Arg Ser
                180                 185                 190

Val Ile Asp Gly Gly Leu Arg Tyr Asn Thr Glu Arg Asp Trp Ala Glu
                195                 200                 205

Asp Tyr Gln Phe Trp Tyr Asp Val Ser Lys Leu Gly Arg Leu Ala Tyr
                210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
                260                 265                 270

Asp Ser Leu Glu Tyr Arg Gln Ile Lys Ala Val Ala Tyr Glu Leu Leu
                275                 280                 285

Glu Lys His Leu Pro Glu Glu Asp Phe Glu Arg Ala Arg Arg Phe Leu
```

-continued

```
          290              295              300

Tyr Gln Cys Phe Lys Arg Thr Asp Thr Pro Met Pro Val Pro Gly
305                 310              315

<210> SEQ ID NO 4
<211> LENGTH: 300
<212> TYPE: PRT
<213> ORGANISM: Artificial Sequence
<220> FEATURE:
<223> OTHER INFORMATION: Synthetic Construct

<400> SEQUENCE: 4

Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
            35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
        115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
        195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
        275                 280                 285

Glu Lys His Leu Pro Asn Glu Asp Phe Arg Lys Ser
        290                 295                 300

<210> SEQ ID NO 5
<211> LENGTH: 348
<212> TYPE: PRT
<213> ORGANISM: Artificial Sequence
<220> FEATURE:
<223> OTHER INFORMATION: Synthetic Construct
```

-continued

<400> SEQUENCE: 5

Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Arg Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
        195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
        275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
            340                 345

<210> SEQ ID NO 6
<211> LENGTH: 348
<212> TYPE: PRT
<213> ORGANISM: Artificial Sequence
<220> FEATURE:
<223> OTHER INFORMATION: Synthetic Construct

<400> SEQUENCE: 6

-continued

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
            35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
            195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser His Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
            275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
            325                 330                 335

Tyr Phe Gly Ile Leu Arg Arg Leu Leu Lys Asn Arg
            340                 345
```

```
<210> SEQ ID NO 7
<211> LENGTH: 348
<212> TYPE: PRT
<213> ORGANISM: Artificial Sequence
<220> FEATURE:
<223> OTHER INFORMATION: Synthetic Construct

<400> SEQUENCE: 7
```

```
Met Pro Ser Glu Ala Phe Arg Arg His Arg Ala Tyr Arg Glu Asn Lys
1               5                   10                  15
```

-continued

```
Leu Gln Ser Leu Val Ser Val Leu Ile Cys Ala Tyr Asn Val Glu Lys
        20                  25                  30

Tyr Phe Ala Gln Ser Leu Ala Ala Val Val Asn Gln Thr Trp Arg Asn
        35              40                  45

Leu Glu Ile Leu Ile Val Asp Asp Gly Ser Thr Asp Gly Thr Leu Ala
    50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
            165                 170                 175

Pro Phe Gly Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
        195                 200                 205

Asp Tyr Gln Phe Trp Tyr Asp Val Ser Lys Leu Gly Arg Leu Ala Tyr
    210                 215                 220

Tyr Pro Glu Ala Pro Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
            245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
        275                 280                 285

Glu Lys His Leu Pro Glu Glu Asp Phe Glu Arg Ala Arg Arg Phe Leu
    290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
            325                 330                 335

Tyr Phe Gly Ile Leu Arg Arg Leu Leu Lys Asn Arg
            340                 345
```

<210> SEQ ID NO 8
<211> LENGTH: 348
<212> TYPE: PRT
<213> ORGANISM: Artificial Sequence
<220> FEATURE:
<223> OTHER INFORMATION: Synthetic Construct

<400> SEQUENCE: 8

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
        20                  25                  30
```

```
Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
    50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
                100                 105                 110

Asp Asp Ile Ala Ala Pro Asp Trp Ile Glu Lys Ile Val Gly Glu Met
        115                 120                 125

Glu Lys Asp Arg Ser Ile Ile Ala Met Gly Ala Trp Leu Glu Val Leu
    130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Asn Thr Pro Ile Met Arg Arg Ser
                180                 185                 190

Val Ile Asp Gly Gly Leu Arg Tyr Asn Thr Glu Arg Asp Trp Ala Glu
                195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
                260                 265                 270

Asp Ser Leu Glu Tyr Arg Gln Ile Lys Ala Val Ala Tyr Glu Leu Leu
        275                 280                 285

Glu Lys His Leu Pro Glu Glu Asp Phe Glu Arg Ala Arg Arg Phe Leu
    290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
        340                 345
```

```
<210> SEQ ID NO 9
<211> LENGTH: 348
<212> TYPE: PRT
<213> ORGANISM: Artificial Sequence
<220> FEATURE:
<223> OTHER INFORMATION: Synthetic Construct

<400> SEQUENCE: 9
```

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
        35                  40                  45
```

-continued

```
Leu Glu Ile Leu Ile Val Asp Asp Gly Ser Thr Asp Gly Thr Leu Ala
    50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
                100                 105                 110

Asp Asp Ile Ala Ala Pro Asp Trp Ile Glu Lys Ile Val Gly Glu Met
                115                 120                 125

Glu Lys Asp Arg Ser Ile Ile Ala Met Gly Ala Trp Leu Glu Val Leu
    130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Gly Thr Met Ile Met Arg Arg Ser
                180                 185                 190

Val Ile Asp Gly Gly Leu Arg Tyr Asn Thr Glu Arg Asp Trp Ala Glu
                195                 200                 205

Asp Tyr Gln Phe Trp Tyr Asp Val Ser Lys Leu Gly Arg Leu Ala Tyr
    210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
                260                 265                 270

Asp Ser Leu Glu Tyr Arg Gln Ile Lys Ala Val Ala Tyr Glu Leu Leu
    275                 280                 285

Glu Lys His Leu Pro Glu Glu Asp Phe Glu Arg Ala Arg Arg Phe Leu
    290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
                340                 345
```

```
<210> SEQ ID NO 10
<211> LENGTH: 348
<212> TYPE: PRT
<213> ORGANISM: Artificial Sequence
<220> FEATURE:
<223> OTHER INFORMATION: Synthetic Construct

<400> SEQUENCE: 10
```

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
                35                  40                  45

Leu Glu Ile Leu Ile Val Asp Asp Gly Ser Thr Asp Gly Thr Leu Ala
    50                  55                  60
```

-continued

```
Ile Ala Lys Asp Phe Gln Lys Arg Asp Ser Arg Ile Lys Ile Leu Ala
65                  70                  75                  80

Gln Ala Gln Asn Ser Gly Leu Ile Thr Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Arg Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
            195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
        275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
            340                 345
```

```
<210> SEQ ID NO 11
<211> LENGTH: 348
<212> TYPE: PRT
<213> ORGANISM: Artificial Sequence
<220> FEATURE:
<223> OTHER INFORMATION: Synthetic Construct

<400> SEQUENCE: 11
```

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
            35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80
```

-continued

```
Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
            195                 200                 205

Asp Tyr Val Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
        275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
                340                 345
```

```
<210> SEQ ID NO 12
<211> LENGTH: 348
<212> TYPE: PRT
<213> ORGANISM: Artificial Sequence
<220> FEATURE:
<223> OTHER INFORMATION: Synthetic Construct

<400> SEQUENCE: 12
```

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
            35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95
```

```
Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
        195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Val
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
        275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
            340                 345
```

<210> SEQ ID NO 13
<211> LENGTH: 348
<212> TYPE: PRT
<213> ORGANISM: Artificial Sequence
<220> FEATURE:
<223> OTHER INFORMATION: Synthetic Construct

<400> SEQUENCE: 13

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110
```

-continued

```
Asp Asp Ile Ala Ala Pro Asp Trp Ile Glu Lys Ile Val Gly Glu Met
        115                 120                 125

Glu Lys Asp Arg Ser Ile Ile Ala Met Gly Ala Trp Leu Glu Val Leu
    130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Gly Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
            195                 200                 205

Asp Tyr Gln Phe Asn Tyr Asp Val Ser Lys Leu Gly Arg Leu Ala Tyr
    210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
        275                 280                 285

Glu Lys His Leu Pro Glu Glu Asp Phe Glu Arg Ala Arg Arg Phe Leu
    290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
                340                 345

<210> SEQ ID NO 14
<211> LENGTH: 348
<212> TYPE: PRT
<213> ORGANISM: Artificial Sequence
<220> FEATURE:
<223> OTHER INFORMATION: Synthetic Construct

<400> SEQUENCE: 14

Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
            35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
        115                 120                 125
```

-continued

```
Glu Lys Asp Arg Ser Ile Ile Ala Met Gly Ala Trp Leu Glu Val Leu
    130                 135                 140

Ser Glu Glu Lys Asp Gly Asn Arg Leu Ala Arg His His Arg His Gly
145                 150                 155                 160

Lys Ile Trp Lys Lys Pro Thr Arg His Leu Asp Ile Ala Asp Phe Phe
                165                 170                 175

Pro Phe Arg Asn Pro Ile His Asn Asn Thr Met Ile Met Arg Arg Ser
                180                 185                 190

Val Ile Asp Gly Gly Leu Arg Tyr Asn Thr Glu Arg Asp Trp Ala Glu
                195                 200                 205

Asp Tyr Gln Phe Trp Tyr Asp Val Ser Lys Leu Gly Arg Leu Ala Tyr
    210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
                260                 265                 270

Asp Ser Leu Glu Tyr Arg Gln Ile Lys Ala Val Ala Tyr Glu Leu Leu
    275                 280                 285

Glu Lys His Leu Pro Glu Glu Asp Phe Glu Arg Ala Arg Arg Phe Leu
    290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
                340                 345

<210> SEQ ID NO 15
<211> LENGTH: 348
<212> TYPE: PRT
<213> ORGANISM: Artificial Sequence
<220> FEATURE:
<223> OTHER INFORMATION: Synthetic Construct

<400> SEQUENCE: 15

Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
            35                  40                  45

Leu Glu Ile Leu Ile Val Asp Asp Gly Ser Thr Asp Gly Thr Leu Ala
    50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
        115                 120                 125

Glu Lys Asp Arg Ser Ile Ile Ala Met Gly Ala Trp Leu Glu Val Leu
    130                 135                 140
```

```
Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Arg Asn Pro Val His Asn Asn Thr Met Ile Met Arg Arg Ser
            180                 185                 190

Val Ile Asp Gly Gly Leu Arg Tyr Asn Thr Glu Arg Asp Trp Ala Glu
            195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
            275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
            340                 345
```

```
<210> SEQ ID NO 16
<211> LENGTH: 348
<212> TYPE: PRT
<213> ORGANISM: Artificial Sequence
<220> FEATURE:
<223> OTHER INFORMATION: Synthetic Construct

<400> SEQUENCE: 16
```

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
    50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160
```

-continued

```
Lys Ile Trp Lys Lys Pro Thr Arg His Glu Asp Ile Ala Asp Phe Phe
                165                 170                 175

Pro Phe Arg Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
            195                 200                 205

Asp Tyr Gln Phe Trp Tyr Asp Leu Ser Lys Leu Gly Arg Leu Ala Tyr
        210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
        275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
            325                 330                 335

Tyr Phe Gly Ile Leu Arg Arg Leu Leu Lys Asn Arg
            340                 345
```

```
<210> SEQ ID NO 17
<211> LENGTH: 348
<212> TYPE: PRT
<213> ORGANISM: Artificial Sequence
<220> FEATURE:
<223> OTHER INFORMATION: Synthetic Construct

<400> SEQUENCE: 17
```

```
Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175
```

```
Pro Phe Arg Asn Pro Ile His Asn Asn Thr Met Ile Met Arg Arg Ser
            180             185             190

Val Ile Asp Gly Gly Leu Arg Tyr Asn Thr Glu Arg Asp Trp Ala Glu
            195             200             205

Asp Tyr Gln Phe Trp Tyr Asp Val Ser Lys Leu Gly Arg Leu Ala Tyr
            210             215             220

Tyr Pro Glu Ala Leu Val Lys Tyr Arg Leu His Ala Asn Gln Val Ser
225                 230             235                 240

Ser Lys Tyr Ser Ile Arg Gln His Glu Ile Ala Gln Gly Ile Gln Lys
                245             250             255

Thr Ala Arg Asn Asp Phe Leu Gln Ser Met Gly Phe Lys Thr Arg Phe
            260             265             270

Asp Ser Leu Glu Tyr Arg Gln Ile Lys Ala Val Ala Tyr Glu Leu Leu
            275             280             285

Glu Gln His Leu Pro Glu Glu Asp Phe Glu Arg Ala Arg Arg Phe Leu
            290             295             300

Tyr Gln Cys Phe Lys Arg Thr Asp Thr Pro Pro Ala Gly Ala Trp Leu
305                 310             315                 320

Asp Phe Ala Ala Asp Gly Arg Met Arg Arg Leu Phe Thr Leu Arg Gln
                325             330             335

Tyr Phe Gly Ile Leu Arg Arg Leu Leu Lys Asn Arg
            340             345
```

```
<210> SEQ ID NO 18
<211> LENGTH: 348
<212> TYPE: PRT
<213> ORGANISM: Artificial Sequence
<220> FEATURE:
<223> OTHER INFORMATION: Synthetic Construct

<400> SEQUENCE: 18
```

```
Met Pro Ser Glu Ala Phe Arg Arg His Arg Ala Tyr Arg Glu Asn Lys
1               5               10              15

Leu Gln Ser Leu Val Ser Val Leu Ile Cys Ala Tyr Asn Val Glu Lys
            20              25              30

Tyr Phe Ala Gln Ser Leu Ala Ala Val Val Asn Gln Thr Trp Arg Asn
            35              40              45

Leu Glu Ile Leu Ile Val Asp Asp Gly Ser Thr Asp Gly Thr Leu Ala
            50              55              60

Ile Ala Lys Asp Phe Gln Lys Arg Asp Ser Arg Ile Lys Ile Leu Ala
65                  70              75                  80

Gln Ala Gln Asn Ser Gly Leu Ile Pro Ser Leu Asn Ile Gly Leu Asp
                85              90              95

Glu Leu Ala Lys Ser Gly Met Gly Glu Tyr Ile Ala Arg Thr Asp Ala
            100             105             110

Asp Asp Ile Ala Ala Pro Asp Trp Ile Glu Lys Ile Val Gly Glu Met
            115             120             125

Glu Lys Asp Arg Ser Ile Ile Ala Met Gly Ala Trp Leu Glu Val Leu
            130             135             140

Ser Glu Glu Lys Asp Gly Asn Arg Leu Ala Arg His His Arg His Gly
145                 150             155                 160

Lys Ile Trp Lys Lys Pro Thr Arg His Glu Asp Ile Ala Asp Phe Phe
                165             170             175

Pro Phe Arg Asn Pro Ile His Asn Asn Thr Met Ile Met Arg Arg Ser
            180             185             190
```

Val Ile Asp Gly Gly Leu Arg Tyr Asn Thr Glu Arg Asp Trp Ala Glu
        195                     200                 205

Asp Tyr Gln Phe Trp Tyr Asp Val Ser Lys Leu Gly Arg Leu Ala Tyr
        210                     215                 220

Tyr Pro Glu Ala Leu Ala Lys Tyr Arg Leu His Ala Asn Gln Val Ser
225                     230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
            260                 265                 270

Asp Ser Leu Glu Tyr Arg Gln Ile Lys Ala Val Ala Tyr Glu Leu Leu
            275                 280                 285

Glu Lys His Leu Pro Glu Glu Asp Phe Glu Arg Ala Arg Arg Phe Leu
        290                     295                 300

Tyr Gln Cys Phe Lys Arg Thr Asp Thr Pro Pro Ala Gly Ala Trp Leu
305                     310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
            340                 345

<210> SEQ ID NO 19
<211> LENGTH: 348
<212> TYPE: PRT
<213> ORGANISM: Artificial Sequence
<220> FEATURE:
<223> OTHER INFORMATION: Synthetic Construct

<400> SEQUENCE: 19

Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
    50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                     135                 140

Ser Glu Glu Lys Asp Gly Asn Arg Leu Ala Arg His His Arg His Gly
145                     150                 155                 160

Lys Ile Trp Lys Lys Pro Thr Arg His Glu Asp Ile Ala Asp Phe Phe
                165                 170                 175

Pro Phe Arg Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
        195                     200                 205

-continued

Asp Tyr Gln Phe Trp Tyr Asp Val Ser Lys Leu Gly Arg Leu Ala Tyr
    210                 215                 220

Tyr Pro Glu Ala Leu Val Lys Tyr Arg Leu His Ala Asn Gln Val Ser
225                 230                 235                 240

Ser Lys Tyr Thr Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
                260                 265                 270

Asp Ser Leu Glu Tyr Arg Gln Ile Lys Ala Val Ala Tyr Glu Leu Leu
            275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
            340                 345

<210> SEQ ID NO 20
<211> LENGTH: 369
<212> TYPE: PRT
<213> ORGANISM: Artificial Sequence
<220> FEATURE:
<223> OTHER INFORMATION: Synthetic Construct

<400> SEQUENCE: 20

Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
            20                  25                  30

Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
    50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Arg Asn Pro Ile His Asn Asn Thr Met Ile Met Arg Arg Ser
            180                 185                 190

Val Ile Asp Gly Gly Leu Arg Tyr Asn Thr Glu Arg Asp Trp Ala Glu
            195                 200                 205

Asp Tyr Gln Phe Trp Tyr Asp Val Ser Lys Leu Gly Arg Leu Ala Tyr
    210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln His Ile Arg Gln His Glu Ile Ala
                260                 265                 270

Gln Gly Ile Gln Lys Thr Ala Arg Asn Asp Phe Leu Gln Ser Met Gly
            275                 280                 285

Phe Lys Thr Arg Phe Asp Ser Leu Glu Tyr Arg Gln Ile Lys Ala Val
        290                 295                 300

Ala Tyr Glu Leu Leu Glu Lys His Leu Pro Glu Glu Asp Phe Glu Arg
305                 310                 315                 320

Ala Arg Arg Phe Leu Tyr Gln Cys Phe Lys Arg Thr Asp Thr Pro Pro
                325                 330                 335

Ala Gly Ala Trp Leu Asp Phe Ala Ala Asp Gly Arg Met Arg Arg Leu
                340                 345                 350

Phe Thr Leu Arg Gln Tyr Phe Gly Ile Leu Arg Arg Leu Leu Lys Asn
        355                 360                 365

Arg

<210> SEQ ID NO 21
<211> LENGTH: 348
<212> TYPE: PRT
<213> ORGANISM: Artificial Sequence
<220> FEATURE:
<223> OTHER INFORMATION: Synthetic Construct

<400> SEQUENCE: 21

Met Pro Ser Glu Ala Phe Arg Arg His Arg Ala Tyr Arg Glu Asn Lys
1               5                   10                  15

Leu Gln Ser Leu Val Ser Val Leu Ile Cys Ala Tyr Asn Val Glu Lys
                20                  25                  30

Tyr Phe Ala Gln Ser Leu Ala Ala Val Val Asn Gln Thr Trp Arg Asn
        35                  40                  45

Leu Glu Ile Leu Ile Val Asp Asp Gly Ser Thr Asp Gly Thr Leu Ala
    50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
            100                 105                 110

Asp Asp Ile Ala Ala Pro Asp Trp Ile Glu Lys Ile Val Gly Glu Met
        115                 120                 125

Glu Lys Asp Arg Ser Ile Ile Ala Met Gly Ala Trp Leu Glu Val Leu
    130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Arg Asn Pro Ile His Asn Asn Thr Met Ile Met Arg Arg Ser
        180                 185                 190

Val Ile Asp Gly Gly Leu Arg Tyr Asn Thr Glu Arg Asp Trp Ala Glu
        195                 200                 205

Asp Tyr Gln Phe Trp Tyr Asp Val Ser Lys Leu Gly Arg Leu Ala Tyr

```
          210                 215                 220

Tyr Pro Glu Ala Leu Val Lys Tyr Arg Leu His Ala Asn Gln Val Ser
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
                260                 265                 270

Asp Ser Leu Glu Tyr Arg Gln Ile Lys Ala Val Tyr Tyr Glu Leu Leu
            275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
                340                 345

<210> SEQ ID NO 22
<211> LENGTH: 348
<212> TYPE: PRT
<213> ORGANISM: Artificial Sequence
<220> FEATURE:
<223> OTHER INFORMATION: Synthetic Construct

<400> SEQUENCE: 22

Met Pro Ser Glu Ala Phe Arg Arg His Arg Ala Tyr Arg Glu Asn Lys
1               5                   10                  15

Leu Gln Ser Leu Val Ser Val Leu Ile Cys Gly Tyr Asn Val Glu Lys
                20                  25                  30

Tyr Phe Ala Gln Ser Leu Ala Ala Val Val Asn Gln Thr Trp Arg Asn
            35                  40                  45

Leu Glu Ile Leu Ile Val Asp Asp Gly Ser Thr Asp Gly Thr Leu Ala
        50                  55                  60

Ile Ala Lys Asp Phe Gln Lys Arg Asp Ser Arg Ile Lys Ile Leu Ala
65                  70                  75                  80

Gln Ala Gln Asn Ser Gly Leu Ile Pro Ser Leu Asn Ile Gly Leu Asp
                85                  90                  95

Glu Leu Ala Lys Ser Gly Met Gly Glu Tyr Ile Ala Arg Thr Asp Ala
                100                 105                 110

Asp Asp Ile Ala Ala Pro Asp Trp Ile Glu Lys Ile Val Gly Glu Met
            115                 120                 125

Glu Lys Asp Arg Ser Ile Ile Ala Met Gly Ala Trp Leu Glu Val Leu
        130                 135                 140

Ser Glu Glu Lys Asp Gly Asn Arg Leu Ala Arg His His Arg His Gly
145                 150                 155                 160

Lys Ile Trp Lys Lys Pro Thr Arg His Glu Asp Ile Ala Asp Phe Phe
                165                 170                 175

Pro Phe Arg Asn Pro Ile His Asn Asn Thr Met Ile Met Arg Arg Ser
                180                 185                 190

Val Ile Asp Gly Gly Leu Arg Tyr Asn Thr Glu Arg Asp Trp Ala Glu
            195                 200                 205

Asp Tyr Gln Phe Trp Tyr Asp Val Ser Lys Leu Gly Arg Leu Ala Tyr
        210                 215                 220

Tyr Pro Glu Ala Leu Val Lys Tyr Arg Leu His Ala Asn Gln Val Ser
```

-continued

```
225                 230                 235                 240

Ser Lys Tyr Ser Ile Arg Gln His Glu Ile Ala Gln Gly Ile Gln Lys
                245                 250                 255

Thr Ala Arg Asn Asp Phe Leu Gln Ser Met Gly Phe Lys Thr Arg Phe
                260                 265                 270

Asp Ser Leu Glu Tyr Arg Gln Ile Lys Ala Val Ala Tyr Glu Leu Leu
                275                 280                 285

Glu Lys His Leu Pro Glu Glu Asp Phe Glu Arg Ala Arg Arg Phe Leu
        290                 295                 300

Tyr Gln Cys Phe Lys Arg Thr Asp Thr Pro Pro Ala Gly Ala Trp Leu
305                 310                 315                 320

Asp Phe Ala Ala Asp Gly Arg Met Arg Arg Leu Phe Thr Leu Arg Gln
                325                 330                 335

Tyr Phe Gly Ile Leu Arg Arg Leu Leu Lys Asn Arg
                340                 345
```

<210> SEQ ID NO 23
<211> LENGTH: 587
<212> TYPE: PRT
<213> ORGANISM: Kluyveromyces lactis

<400> SEQUENCE: 23

```
Met Ala Asp His Ser Ser Ser Ser Ser Leu Gln Lys Lys Pro Ile
1               5                   10                  15

Asn Thr Ile Glu His Lys Asp Thr Leu Gly Asn Asp Arg Asp His Lys
                20                  25                  30

Glu Ala Leu Asn Ser Asp Asn Asp Asn Thr Ser Gly Leu Lys Ile Asn
        35                  40                  45

Gly Val Pro Ile Glu Asp Ala Arg Glu Glu Val Leu Leu Pro Gly Tyr
        50                  55                  60

Leu Ser Lys Gln Tyr Tyr Lys Leu Tyr Gly Leu Cys Phe Ile Thr Tyr
65                  70                  75                  80

Leu Cys Ala Thr Met Gln Gly Tyr Asp Gly Ala Leu Met Gly Ser Ile
                85                  90                  95

Tyr Thr Glu Asp Ala Tyr Leu Lys Tyr Tyr His Leu Asp Ile Asn Ser
                100                 105                 110

Ser Ser Gly Thr Gly Leu Val Phe Ser Ile Phe Asn Val Gly Gln Ile
        115                 120                 125

Cys Gly Ala Phe Phe Val Pro Leu Met Asp Trp Lys Gly Arg Lys Pro
        130                 135                 140

Ala Ile Leu Ile Gly Cys Leu Gly Val Val Ile Gly Ala Ile Ile Ser
145                 150                 155                 160

Ser Leu Thr Thr Thr Lys Ser Ala Leu Ile Gly Gly Arg Trp Phe Val
                165                 170                 175

Ala Phe Phe Ala Thr Ile Ala Asn Ala Ala Ala Pro Thr Tyr Cys Ala
                180                 185                 190

Glu Val Ala Pro Ala His Leu Arg Gly Lys Val Ala Gly Leu Tyr Asn
                195                 200                 205

Thr Leu Trp Ser Val Gly Ser Ile Val Ala Ala Phe Ser Thr Tyr Gly
        210                 215                 220

Thr Asn Lys Asn Phe Pro Asn Ser Ser Lys Ala Phe Lys Ile Pro Leu
225                 230                 235                 240

Tyr Leu Gln Met Met Phe Pro Gly Leu Val Cys Ile Phe Gly Trp Leu
                245                 250                 255
```

-continued

```
Ile Pro Glu Ser Pro Arg Trp Leu Val Gly Val Gly Arg Glu Glu Glu
            260             265             270

Ala Arg Glu Phe Ile Ile Lys Tyr His Leu Asn Gly Asp Arg Thr His
            275             280             285

Pro Leu Leu Asp Met Glu Met Ala Glu Ile Ile Glu Ser Phe His Gly
            290             295             300

Thr Asp Leu Ser Asn Pro Leu Glu Met Leu Asp Val Arg Ser Leu Phe
305             310             315             320

Arg Thr Arg Ser Asp Arg Tyr Arg Ala Met Leu Val Ile Leu Met Ala
            325             330             335

Trp Phe Gly Gln Phe Ser Gly Asn Asn Val Cys Ser Tyr Tyr Leu Pro
            340             345             350

Thr Met Leu Arg Asn Val Gly Met Lys Ser Val Ser Leu Asn Val Leu
            355             360             365

Met Asn Gly Val Tyr Ser Ile Val Thr Trp Ile Ser Ser Ile Cys Gly
            370             375             380

Ala Phe Phe Ile Asp Lys Ile Gly Arg Arg Glu Gly Phe Leu Gly Ser
385             390             395             400

Ile Ser Gly Ala Ala Leu Ala Leu Thr Gly Leu Ser Ile Cys Thr Ala
            405             410             415

Arg Tyr Glu Lys Thr Lys Lys Lys Ser Ala Ser Asn Gly Ala Leu Val
            420             425             430

Phe Ile Tyr Leu Phe Gly Gly Ile Phe Ser Phe Ala Phe Thr Pro Met
            435             440             445

Gln Ser Met Tyr Ser Thr Glu Val Ser Thr Asn Leu Thr Arg Ser Lys
            450             455             460

Ala Gln Leu Leu Asn Phe Val Val Ser Gly Val Ala Gln Phe Val Asn
465             470             475             480

Gln Phe Ala Thr Pro Lys Ala Met Lys Asn Ile Lys Tyr Trp Phe Tyr
            485             490             495

Val Phe Tyr Val Phe Phe Asp Ile Phe Glu Phe Ile Val Ile Tyr Phe
            500             505             510

Phe Phe Val Glu Thr Lys Gly Arg Ser Leu Glu Glu Leu Glu Val Val
            515             520             525

Phe Glu Ala Pro Asn Pro Arg Lys Ala Ser Val Asp Gln Ala Phe Leu
            530             535             540

Ala Gln Val Arg Ala Thr Leu Val Gln Arg Asn Asp Val Arg Val Ala
545             550             555             560

Asn Ala Gln Asn Leu Lys Glu Gln Glu Pro Leu Lys Ser Asp Ala Asp
            565             570             575

His Val Glu Lys Leu Ser Glu Ala Glu Ser Val
            580             585
```

```
<210> SEQ ID NO 24
<211> LENGTH: 282
<212> TYPE: PRT
<213> ORGANISM: Pasteurella multocida

<400> SEQUENCE: 24
```

```
Met Ser Gly Glu His Tyr Val Ile Ser Leu Ser Ser Ala Val Glu Arg
1               5               10              15

Arg Gln His Ile Arg Asn Gln Phe Ser Gln Lys Asn Ile Pro Phe Gln
            20              25              30

Phe Phe Asp Ala Ile Ser Pro Ser Pro Leu Leu Asp Gln Leu Val Leu
            35              40              45
```

-continued

```
Gln Phe Phe Pro Arg Leu Ala Asp Ser Ser Leu Thr Gly Gly Glu Lys
    50                  55                  60

Ala Cys Phe Met Ser His Leu Ser Leu Trp His Lys Cys Val Glu Glu
65                  70                  75                  80

Asn Leu Pro Tyr Ile Val Val Phe Glu Asp Asp Ile Val Leu Gly Lys
                85                  90                  95

Asp Ala Asp Lys Phe Leu Ile Gly Asp Glu Trp Leu Phe Ser Arg Phe
            100                 105                 110

Asp Pro Glu Glu Ile Phe Ile Ile Arg Leu Glu Thr Phe Leu Gln Lys
            115                 120                 125

Val Val Cys Glu Ser Thr His Ile Ala Pro Tyr Thr His Arg Asp Phe
    130                 135                 140

Leu Ser Leu Lys Ser Ala His Phe Gly Thr Ala Gly Tyr Val Ile Ser
145                 150                 155                 160

Gln Gly Ala Ala Lys Phe Leu Leu Asp Ile Phe Lys Asn Ile Ser Asn
                165                 170                 175

Glu His Ile Ala Pro Ile Asp Glu Leu Ile Phe Asn Gln Phe Leu Val
            180                 185                 190

Lys Asn Ser Phe Asn Val Tyr Gln Leu Ser Pro Ala Ile Cys Val Gln
            195                 200                 205

Glu Leu Gln Leu Asn Asn Glu Ser Ser Ala Leu Gln Ser Gln Leu Glu
    210                 215                 220

Leu Glu Arg Asn Lys Phe Arg Asn Lys Lys Ser Glu Glu Leu Lys Arg
225                 230                 235                 240

Asn Arg Lys Asn Phe Ile Glu Lys Phe Ile Tyr Ile Leu Lys Lys Pro
                245                 250                 255

Lys Arg Met Leu Asp Asn Asn Lys Arg Lys Arg Glu Glu Ser Lys Ile
            260                 265                 270

Glu Asn Asp Lys Met Ile Ile Glu Phe Lys
            275                 280
```

<210> SEQ ID NO 25
<211> LENGTH: 279
<212> TYPE: PRT
<213> ORGANISM: Neisseria gonorrhoeae

<400> SEQUENCE: 25

```
Met Gln Asn His Val Ile Ser Leu Ala Ser Ala Ala Glu Arg Arg Ala
1               5                   10                  15

His Ile Ala Ala Thr Phe Gly Ser Arg Gly Ile Pro Phe Gln Phe Phe
                20                  25                  30

Asp Ala Leu Met Pro Ser Glu Arg Leu Glu Arg Ala Met Ala Glu Leu
            35                  40                  45

Val Pro Gly Leu Ser Ala His Pro Tyr Leu Ser Gly Val Glu Lys Ala
    50                  55                  60

Cys Phe Met Ser His Ala Val Leu Trp Glu Gln Ala Leu Asp Glu Gly
65                  70                  75                  80

Val Pro Tyr Ile Ala Val Phe Glu Asp Asp Val Leu Leu Gly Glu Gly
                85                  90                  95

Ala Glu Gln Phe Leu Ala Glu Asp Thr Trp Leu Gln Glu Arg Phe Asp
            100                 105                 110

Pro Asp Ser Ala Phe Val Val Arg Leu Glu Thr Met Phe Met His Val
            115                 120                 125

Leu Thr Ser Pro Ser Gly Val Ala Asp Tyr Gly Gly Arg Ala Phe Pro
```

-continued

```
        130               135               140

Leu Leu Glu Ser Glu His Cys Gly Thr Ala Gly Tyr Ile Ile Ser Arg
145               150               155               160

Lys Ala Met Arg Phe Phe Leu Asp Arg Phe Ala Val Leu Pro Pro Glu
                165               170               175

Arg Leu His Pro Val Asp Leu Met Met Phe Gly Asn Pro Asp Asp Arg
            180               185               190

Glu Gly Met Pro Val Cys Gln Leu Asn Pro Ala Leu Cys Ala Gln Glu
        195               200               205

Leu His Tyr Ala Lys Phe His Asp Gln Asn Ser Ala Leu Gly Ser Leu
    210               215               220

Ile Glu His Asp Arg Arg Leu Asn Arg Lys Gln Gln Trp Arg Asp Ser
225               230               235               240

Pro Ala Asn Thr Phe Lys His Arg Leu Ile Arg Ala Leu Thr Lys Ile
            245               250               255

Gly Arg Glu Arg Glu Lys Arg Arg Gln Arg Arg Glu Gln Leu Ile Gly
            260               265               270

Lys Ile Ile Val Pro Phe Gln
        275
```